(12) United States Patent
Gutman et al.

(10) Patent No.: US 7,977,324 B2
(45) Date of Patent: *Jul. 12, 2011

(54) PROCESS FOR PREPARING MALATHION FOR PHARMACEUTICAL USE

(75) Inventors: Daniella Gutman, Rishon Lezion (IL); Wael Baidussi, Hamisholash (IL)

(73) Assignee: Taro Pharmaceuticals North America, Inc., Cayman (KY)

( * ) Notice: Subject to any disclaimer, the term of this patent is extended or adjusted under 35 U.S.C. 154(b) by 45 days.

This patent is subject to a terminal disclaimer.

(21) Appl. No.: 12/353,691

(22) Filed: Jan. 14, 2009

(65) Prior Publication Data

US 2009/0124823 A1    May 14, 2009

Related U.S. Application Data

(63) Continuation of application No. 11/427,863, filed on Jun. 30, 2006, now Pat. No. 7,560,445.

(60) Provisional application No. 60/697,010, filed on Jul. 6, 2005, provisional application No. 60/741,360, filed on Dec. 1, 2005, provisional application No. 60/743,741, filed on Mar. 24, 2006.

(51) Int. Cl.
*A61K 31/66* (2006.01)
(52) U.S. Cl. ........................................ 514/127
(58) Field of Classification Search .................. 514/127
See application file for complete search history.

(56) References Cited

U.S. PATENT DOCUMENTS

| | | | |
|---|---|---|---|
| 2,578,652 A | 12/1951 | Cassaday |
| 2,863,902 A | 12/1958 | Santay |
| 2,879,284 A | 3/1959 | Divine et al. |
| 2,931,825 A | 4/1960 | Lutz |
| 2,962,521 A | 11/1960 | Usui |
| 2,980,723 A | 4/1961 | Frank et al. |
| 3,309,432 A | 3/1967 | English |
| 3,352,664 A | 11/1967 | Nolan et al. |
| 3,396,223 A | 8/1968 | Stark, Jr. |
| 3,403,201 A | 9/1968 | Adrian et al. |
| 3,440,305 A | 4/1969 | Divine |
| 3,463,841 A | 8/1969 | Backlund et al. |
| 3,470,272 A | 9/1969 | Melton |
| 3,515,782 A | 6/1970 | Nolan |
| 3,714,301 A | 1/1973 | Thomsen |
| 4,049,755 A | 9/1977 | Bianchi et al. |
| 4,367,180 A | 1/1983 | Rouy et al. |
| 4,520,013 A | 5/1985 | Nezat |
| 4,681,964 A | 7/1987 | Annarelli et al. |
| 5,783,202 A | 7/1998 | Tomlinson et al. |
| 6,103,248 A | 8/2000 | Burkhart et al. |
| 6,121,478 A | 9/2000 | Pedersen |
| 6,280,729 B1 | 8/2001 | Huang et al. |
| 6,500,994 B1 | 12/2002 | Brosch et al. |
| 6,521,762 B2 | 2/2003 | Keri et al. |
| 6,524,602 B1 | 2/2003 | Burkhart et al. |
| 6,562,363 B1 | 5/2003 | Mantelle et al. |
| 6,596,291 B2 | 7/2003 | Bell |
| 6,607,716 B1 | 8/2003 | Smith et al. |
| 6,689,394 B2 | 2/2004 | Van Scoik et al. |
| 6,806,292 B2 | 10/2004 | Riebel et al. |
| 6,939,715 B2 | 9/2005 | Beck et al. |
| 2002/0009486 A1 | 1/2002 | Godbey |
| 2002/0048558 A1 | 4/2002 | Niemiec et al. |
| 2003/0036530 A1 | 2/2003 | Bessette |
| 2004/0024052 A1 | 2/2004 | Gyuricza et al. |
| 2005/0031547 A1 | 2/2005 | Tamarkin et al. |
| 2006/0121073 A1 | 6/2006 | Goyal et al. |

FOREIGN PATENT DOCUMENTS

| | | |
|---|---|---|
| FR | 1541883 | 10/1968 |
| GB | 834814 | 5/1960 |
| GB | 2204243 | 11/1988 |
| GB | 2222949 | 3/1990 |
| RO | 86214 | 2/1985 |
| RO | 87602 | 12/1985 |
| WO | WO-03/066009 A1 | 8/2003 |
| WO | WO/2006/017232 | 2/2006 |
| WO | WO/2006/017263 | 2/2006 |

OTHER PUBLICATIONS

Meinking et al., Pediatric Dermatology, vol. 21, No. 6, pp. 670-674, 2004.
Nature's Mist, Skin Functioning and Dehydration, www.naturesmist.com, p. 1-4, 2003.
"A modern scourge parent scratch their heads over lice," Consumer Reports, Feb. 1998.
Office Action issued by the USPTO on Feb. 18, 2009 for U.S. Appl. No. 11/179,719.
Office Action issued by the USPTO on Sep. 16, 2009 for U.S. Appl. No. 11/179,719.
Office Action issued by the USPTO on May 27, 2010 for U.S. Appl. No. 11/179,719.
Office Action Issued by the USPTO on Feb. 19, 2009 for U.S. Appl. No. 11/351,188.
Office Action issued by the USPTO on Sep. 21, 2009 for U.S. Appl. No. 11/351,188.

(Continued)

*Primary Examiner* — Rei-tsang Shiao
(74) *Attorney, Agent, or Firm* — Venable LLP; Michael A. Gollin; Zayd Alathari

(57) ABSTRACT

The present invention provides a process for preparing a highly pure form of malathion having a reduced level of toxic impurities. In addition, the malathion prepared by the process of this invention is storage stable. The level of toxic impurities in the malathion, e.g., isomalathion, O,O,S-trimethyl phosphorodithioate (MeOOSPS), O,O,S-trimethyl phosphorothioate (MeOOSPO), O,S,S-trimethyl phosphorodithioate (MeOSSPO), malaoxon, isomalathion, diethyl fumarate, methyl malathion, dimethyl malathion, O,O-methyl,ethyl-S-(1,2-dicarboethoxy)ethyl-phosphorodithioate are lower than that of any other commercial preparation of malathion that may be used for pharmaceutical purposes.

55 Claims, No Drawings

OTHER PUBLICATIONS

Office Action issued by the USPTO on May 27, 2010 for U.S. Appl. No. 11/351,188.
Al-Wakil et al., "Separation and Preconcentration of Malathion and Azamethiphos by Unloaded Polyurethane Foams," Qatar University Science Journal, vol. 14(spec. issue), 1994. (Abstract Only).
Baker, Jr. et al., Epidemic Malathion Poisoning in Pakistan Malaria Workers, The Lancet, vol. 1, No. 8054, 1978.
Blasiak et al., "In Vitro Studies on the Genotoxicity of the Organophosphorus Insecticide Malathion and Its Two Analogues," Mutat. Res., vol. 445, No. 2, pp. 275-283, 2003. (Abstract Only).
Imamura et al., "Pulmonary Toxicity of Phosphorothioate Impurities Found in Organophosphate Insecticides," Pharmacology and Therapeutics, vol. 38, No. 3, pp. 419-427, 1988. (Abstract Only).
Liu et al., "Rapid Isolation with Sep-Pak C18 Cartridges and Wide Bore Capillary Gas Chromatography of Organophosphate Pesticides," Forensic Science International, vol. 41, No. 1-2, pp. 67-72, 1989. (Abstract Only).
Lupea et al., "Addition of Dimethyl Dithiophosphate to Ethyl Maleate and Ethyl Fumarate," Buletinul Stiintific si Tehnic al Institutului Politechnic Traian Vuia Timisoara, Seria Chimie, vol. 26, No. 1, pp. 51-60, 1981. (English Abstract Only).
Makarova et al., "Photometric Determination of Organophosphorus Pesticides After Separation By Thin Layer Chromatography," Industr. Lab., vol. 40, No. 7, pp. 961-964, 1974. (Abstract Only).
Malathion, 1GM, Neat—Product No. PS86; Sigma-Aldrich Catalog, 2003; with Certificate of Analysis.
Malathion, Pestanal®, analytical standard, Sigma-Aldrich Catalog, 2006, with Certificate of Analysis.
Ovide (Malathion) Lotion, 0.5%, NDC 51672-5276-4, Jul. 2005.
Patel et al., "Manufacture of Malathion," Pestic., Symp. (1968), Meeting Date 1964, pp. 69-72. (Abstract Only).
Polec et al., "Simple Syntheses of Malathion and Malaoxon Enantiomers, and Isomalathion Diastereoisomers: Toxicity-Configuration Relationship," Pesticide Science, vol. 53, No. 2, pp. 165-171, 1998. (Abstract Only).
Polec et al., "Synthesis of Malathion Enantiomers," Organika, vol. date 1995, pp. 7-15, 1996. (English Abstract Only).
Reimschussel et al., "Radioisotopic Studies On the Content and Conversion Rates of Toxic Impurities in Malathion," Pesticides: food and environmental implications, Proceedings of a symposium held in Neuherberg, Nov. 24-27, 1987, pp. 301-303, Published 1988. (Abstract Only).
Shvetsova-Shilovskaya et al., "Purification of Technical Carbophos," Khimicheskaya Promyshlennost, vol. 47, No. 11, p. 869, 1971. (English Abstract Only).
Supplementary European Search Report issued in EP Application No. 06774561 on Jun. 4, 2010.
Talcott et al., "Inactivation of Esterases by Impurities Isolated from Technical Malathion," Toxicology and Applied Pharmacology, vol. 49, No. 1, pp. 107-112, 1979. (Abstract Only).
Toia et al., "Identification and Toxicological Evaluation of Impurities in Technical Malathion and Fenthion," J. Agric. Food Chem., vol. 28, No. 3, pp. 599-604, 1980. (Abstract A Only).
Toia et al., "Identification and Toxicological Evaluation of Impurities in Technical Malathion and Fenthion," J. Agric. Food Chem., vol. 28, No. 3, pp. 599-604, 1980. (Abstract B Only).
Umezu, "Toxicity of Malathion to Mammals Potentiation of Toxicity by Impurities," Kagaku To Seibutsu (Chem. Biol.) vol. 16, No. 5, pp. 302-304, 1978. (English Abstract Only).
USP Monographs: Malathion Lotion, 2008.
USP Monographs: Malathion, 2008.
Wilkins et al., "A Study of the Trans-Esterification Products of Malathion by Capillary Gas Chromatography-Mass Spectrometry," Pesticide Science, vol. 20, No. 4, pp. 259-270, 1987. (Abstract Only).
Retro Search, Malathion Impurities, Sep. 13, 2005. (Collection of Abstracts).
Retro Search, Malathion Impurity, Sep. 13, 2005. (Collection of Abstracts).
Stability Results for Malathion Lotion, Aug.-Nov. 2004.
Certificates of Analysis, malathion USP, Cheminova, Jun. 1999-Oct. 2002.
"Impurities of maldison," Review Scope Document Maldison, p. 6-11, Feb. 2003.
EPA 1600 Methods, p. 213, 2003.
EPA 8000 Methods, pp. 238-239, 2003.
"Occupational Exposure to Organophosphate and Carbamate Insecticides." Department of Health and Human Services, p. 1-5, 2003.
Subpart II. B. Pharmacology and Toxicology, p. 62-123, 2003.
"Malathion Reregistration Eligibility Document: Environmental Fate and Effects Chapter," United States Environmental Protection Agency, p. 1-52, 2004.
Ovide (Malathion) Lotion, 0.5%, NDA 18-613, vol. 1 of 21, 1980.
Prioderm Lotion NDA 18-613, Replacement Pages, Book 1 of 3, 1980.
Ovide (Malathion) Lotion, 0.5%, NDC 99207-650-2, p. 3-8, 2004.
Memorandum: EFED's Response to Docket Comment, United States Environmental Protection Agency, p. 1-26, 2000.
Picchioni et al., "Activated Charcoal vs. "Universal Antidote" as an Antidote for Poisons," Toxicology and Applied Pharmacology, vol. 8, pp. 447-454, 1966.
Imamura et al., "Malathion and Phenthoate Carboxylesterase Activities in Pulmonary Alveolar Macrophages as Indicators of Lung Injury," Toxicology and Applied Pharmacology, vol. 70, pp. 140-147, 1983.
Rodgers et al., "Effect of administration of malathion for 90 days on macrophage function and mast cell degranulation," Toxicology Letters, vol. 93, pp. 73-82, 1997.
R. Baselt et al.,"Malathion", Disposition of Toxic Drugs and Chemicals in Man, p. 475-478, 1989.
Office Action issued by the USPTO on Oct. 21, 2008 for U.S. Appl. No. 11/427,863.
Certificate of Analysis for Batch No. S040110, dated Jan. 24, 2005 (redacted).
Certificate of Analysis for Batch No. S050133, dated Jan. 26, 2005 (redacted).
Certificate of Analysis for Batch No. S050151, dated Jan. 26, 2005 (redacted).
Certificate of Analysis for Batch No. S040109, dated Jan. 24, 2005 (redacted).
Certificate of Analysis for Batch No. S050134, dated Feb. 8, 2005 (redacted).
Certificate of Analysis for Batch No. S050135, dated Feb. 10, 2005 (redacted).
Certificate of Analysis for Batch No. S050136, dated Feb. 17, 2005 (redacted).
Certificate of Analysis for Batch No. S050137, dated Feb. 27, 2005 (redacted).
Certificate of Analysis for Batch No. S050155, dated Mar. 22, 2005 (redacted).
Certificate of Analysis for Batch No. S050169, dated Feb. 27, 2005 (redacted).
Certificate of Analysis for Batch No. S050170, dated Mar. 14, 2005 (redacted).
Certificate of Analysis for Batch No. S050171, dated Mar. 14, 2005 (redacted).
Certificate of Analysis for Batch No. S050172, dated Mar. 15, 2005 (redacted).
Certificate of Analysis for Batch No. S050173, dated Apr. 4, 2005 (redacted).
Certificate of Analysis for Batch No. S050174, dated Apr. 4, 2005 (redacted).
Certificate of Analysis for Batch No. S050190, dated Apr. 10, 2005 (redacted).
Certificate of Analysis for Batch No. S050200, dated Apr. 19, 2005 (redacted).
Certificate of Analysis for Batch No. S050201, dated Apr. 19, 2005 (redacted).
WHO Specifications and Evaluations for Public Health Pesticides: Malathion, World Health Organization, 2003.
Health Risk Assessment of Malathion Coproducts in Malathion-Bait Used for Agricultural Pest Eradication in Urban Areas, Report of the California Environmental Protection Agency, 1997.
Umetsu et al., *J. Agric. Food Chem.*, 25: 946-953 (1977).
Keadtisuke et al., *Toxicology Letters*, 52: 35-46 (1990).

Rodgers et al., *Immunopharmacology*, 17: 131-140 (1989).
Aldridge et al., *Archives Toxicology*, 42: 95-106 (1979).
Berkman et al., "Synthesis of Chrial Malathion and Isomalathion", *Terahedron Letters*, 33(11): 1415-1418 (1992).
Imamura et al., *Pharmacology and Therapeutics*, 38(3): 419-427 (1988).
Lahti et al., *Contact Dermatitis*, 12(3): 139-140 (1985).
Cotham WE Jr., et al., *Food Chem*, 37: 824-828 (1989).
N. Lee Wolfe et al., *J. Agric. Food Chem.*, 23(6): 1212-1215 (1976).
P. Boutsiouki et al., "Effects of local blood flow on the percutaneous absorption of the organophosphorus compound malathion: a microdialysis study in man.", *Arch. Toxicology*, 75(6): 321-8 (2001). PubMed Abstract, http://eresources.library.mssm.edu:2115/entrez/query.fcgi?CMD=Text&DM=pubmed, 1 page.
F. Musshoff et al., "Simple determination of 22 organophosphorous pesticides in human blood using headspace solid-phase microextraction and gas chromatorgrphy with mass spectrometric detection", *Chromatogr. Sci.*, 40(1): 29-34 (2002). PubMed Abstract, http://eresources.library.mssm.edu:2115/entrez/query.fcgi?CMD=Text&DB=pubmed, 1 page.
S. Bradu et al., "Flammability of Topical Agents to Common Environmental Fire Hazards", Ab#155-04, Mar. 2005.
M. Bouchard et al., *Toxicological Sciences*, 73: 182-194 (2003).
S. Padilla et al., *Journal of Toxicology and Environmental Health*, Part A, 67: 1477-1489 (2004).
P. Lee et al., *Intensive Care Med.*, 27: 694-699 (2001).
R. Zweiner et al., *Pediatrics*, 81(1): 121-126 (1988).
C. Vidair, Toxicology and Applied Pharmacology, 196: 287-302 (2004).
D. Hamilton, "JMPS Evaluation of Data Supporting Specification—the Practicalities", CIPAC Symposium, Utrecht, 8 pages (Jun. 6, 2005).
M. Fuller, "Jun. 28, 1998—Bradenton Mediterranean Fruit Fly Update DACS", http://pestalert.ifas.ufl.edu/Medfly/dacs06228.htm (accessed Nov. 13, 2005).
W. Boyes et al., *Journal of Applied Toxicology*, 19: 473-483 (1999).
J. Cocker et al., *Toxicology Letters*, 134: 97-103 (2002).
M. Maroni et al., *Toxicology*, 143: 5-37 (2000).
M. Brown et al., *Environ. Sci. Technol.*, 27(2): 388-397 (1993).
R. Krieger et al., *Arch. Environ. Contam. Toxicol.*, 38: 546-553 (2000).
J. Storm et al., *Toxicology*, 150: 1-29 (2000).
J. Cocker et al., *Toxicology*, 134: 97-103 (2002).
B. Nutley et al., *Pestic. Sci.*, 38: 315-322 (1993).
R. Fenske et al., *J. Agric. Food Chem.*, 37: 995-998 (1989).
K. Rodgers et al., *Pesticide Biochemistry and Physiology*, 25: 358-365 (1986).
J. Herath et al., *Cytologia*, 54: 191-195 (1989).
A. Nishio et al., *Journal of Toxicology and Environmental Health*, 8: 939-946 (1981).
Z. Walter et al., *Human Genetics*, 53: 375-381 (1980).
P. Flessel et al., *Environmental and Molecular Mutagenesis*, 22: 7-17 (1993).
S. Amer et al., *Journal of Applied Toxicology*, 16(1): 1-3 (1996).
V. Garry et al., *Teratogenesis, Carcinogenesis, and Mutagenesis*, 10: 21-29 (1990).
A. Nicholas et al., *Mutation Research*, 67: 167-172 (1979).
International Search Report issued for PCT Applciation PCT/US06/26251, mailed on Nov. 21, 2007.
Written Opinion issued for PCT Application PCT/US06/26251, mailed on Nov. 21, 2007.
FAO Specifications and Evaluations for Agricultural Pesticides, Malathion, Food and Agricultural Organization of the United States, Dec. 2004.
Talley, Todd T. "My Research", http://www2.umt.edu/medchem/ttt/research%20page.html, printed on Nov. 13, 2005.
"Determination of minor components in technical Malathion", Cheminova Analyical Methods, edition 1, Jul. 1, 2003.
Malathion, monograph numbe 5470, copyright 1999 by Merck & Co., Inc., Whitehouse Stations, NJ, USA.
Cheminova, "Formulations and Brands", <http://www.cheminova.com/en/insectices/fyfanon/formulations and brands.htm>, 1 page, printed Aug. 26, 2005.
Cheminova, "Background—Fyfanon®", <http://www.cheminova.com/en/insectices/fyfanon/background.htm>, 1 page, printed Aug. 26, 2005.
Attorney for Medicis manufacturer, of Malathion based Ovide—who writes below that "USP grade Malathion is safe, effective and non-toxic", http://ww.safe2use.com/ca-ipm/00-11-28-ltr.htm, printed Oct. 6, 2005.
"Malathion vs. Mosquitoes", CBC Manitoba, http://winnipeg.cbc.ca/indepth/malathion/, 3 pages, Jul. 7, 2004, printed Dec. 14, 2004.
"Pesticides: Topical & Chemical Fact Sheet; Malathion for Mosquito Control", U.S. Environmental Protection Agency, http://www.epa.gov/pesticides/factsheets/malathion4mosquitos.htm, 5 pages, updated Apr. 17, 2002, printed Dec. 14, 2004.
"Malathion—toxicity, ecological toxicity and regulatory information", PAN Pesticides Database—Chemicals, http://www.pesticidenfo.org/Detail_Chemical.jsp?Rec_Id=PC32924, 9 pages, printed Aug. 31, 2005.
"4.20 Malathion (T)**", http://www.fao.org/docrep/W8141E/w8141e0x.htm, 4 pages, printed May 7, 2004.
"Insecticides Used as Ectoparasiticides", Goodman & Gilman's "The Pharmacological Bases of Therapeutics", 9_th Ed., Copyright 1996 McGraw-Hill Companies, Inc., printed May 2, 2003.
"I.A. Reference Dose for Chronic Oral Exposure (RfD): Substance Name—Malathion", 1 page, Last Revised Jan. 1, 1992.
Sigma-Aldrich, "Product Name: Malathion", http://www.sigmaaldrich.com/cgi-bin/hsrun/Distributed/HahtShop/HahtShop.htx;start=frmCa...., 1 page, printed Oct. 9, 2003.
Chemservice, "Detailed Database Results, Description: Malathion", http://www.chemservice.com/result_detail.asp?CATNUM=F2118, 2 pages, printed Oct. 7, 2003.
"Malathion", IARC Summaries & Evaluations, vol. 30, 1983, http://www.inchem.org/documents/iarc/vol30/malathion.html, 4 pages, printed Jul. 11, 2005.
"Maldison (Malathion) Review Scope Document", National Registration Authority For Agricultural and Veterinary Chemicals, Feb. 2003.
"Joint Statement on Review of Malathion", Department of Health, http://www.doh.gov.uk/com/malathion.htm, p. 1-16, Mar. 2003, printed on Oct. 7, 2003.
"COM meeting Apr. 25, 2002", Department of Health, http://www.doh.gov.uk/com/mut023.htm, p. 1-8, printed on Oct. 6, 2003.
"Guidelines for Physicians who supervise workers exposed to cholinesterase-inhibiting pesticides", 4$^{th}$ Ed., Office of Environmental Hazard Assessment California Environmental Protection Agency, 2002.
Ovide (Malathion) Lotion, 0.5%, NDA 18-613, vol. 2, Dec. 31, 1998.

PROCESS FOR PREPARING MALATHION FOR PHARMACEUTICAL USE

This application is a continuation of application Ser. No. 11/427,863, filed on Jun. 30, 2006 now U.S. Pat. No. 7,560,445 which claims the priority under 35 U.S.C. §1.119(e) of Provisional Application Ser. Nos. 60/697,010 filed Jul. 6, 2005, 60/741,360 filed Dec. 1, 2005 and 60/743,741 filed Mar. 24, 2006, all of which are incorporated by reference in their entireties herein.

FIELD OF THE INVENTION

The present invention relates to a process of preparing malathion for pharmaceutical use and compositions comprising a highly purified form of malathion that is stable during storage.

BACKGROUND OF THE INVENTION

Malathion ([(dimethoxyphosphinothioyl)thio]butanedioic acid diethyl ester; CAS # 121-75-5) is an organophosphate insecticide that inhibits cholinesterase activity in vivo. Malathion has the following chemical structure:

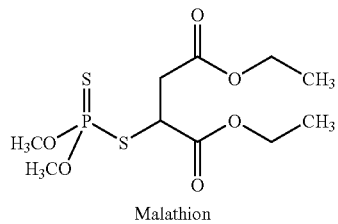

Malathion

Malathion may be prepared by reacting O,O-dimethyldithiophosphoric acid (DMDP) with diethyl maleate (U.S. Pat. Nos. 2,578,652, 2,879,284, 3,403,201, 3,463,841, 3,470,272, 4,367,180 and 4,681,964).

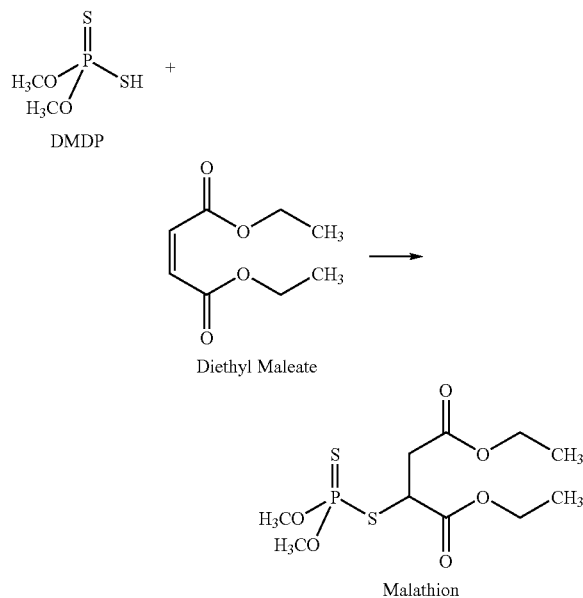

Numerous impurities are found in malathion preparations; these impurities include, O,O,S-trimethyl phosphorodithioate (MeOOSPS), O,O,S-trimethyl phosphorothioate (MeOOSPO), O,S,S-trimethyl phosphorodithioate (MeOSSPO), malaoxon, isomalathion, diethyl fumarate, methyl malathion, dimethyl malathion, O,O-methyl,ethyl-S-(1,2-dicarboethoxy)ethyl-phosphorodithioate, and tetraethyl dithiodisuccinate (See, WHO Specifications and Evaluations for Public Health Pesticides: Malathion, World Health Organization, 2003). Some of these impurities are formed as breakdown products during storage, but, the majority of these impurities are generated as unintentional byproducts during synthesis. (Health Risk Assessment of Malathion Coproducts in Malthion-Bait Used for Agricultural Pest Eradication in Urban Areas, Report of the California Environmental Protection Agency, 1997). For example, during storage, malathion can convert to isomalathion by dimerization, and the extent of isomerization is dependent on particular storage conditions. (Health Risk Assessment of Malathion Coproducts in Malthion-Bait Used for Agricultural Pest Eradication in Urban Areas, Report of the California Environmental Protection Agency, 1997).

Storage of malathion at elevated temperatures, e.g., 40° C., significantly enhances toxicity of the malathion preparation (Umetsu et al., *J. Agric. Food Chem.*, 25:946-953 (1977)). In part, this enhancement is due to an increase in isomalathion after storage. For example, after storage for 6 months at 40° C., there was an increase in isomalathion content from 0.2% to 0.45%, with an accompanying 35% increase in toxicity as measured by $LD_{50}$ in mice (Umetsu et al., *J. Agric. Food Chem.*, 25:946-953 (1977)). Because even small or trace quantities of malathion impurities such as isomalathion have been shown to be highly toxic, the presence of these impurities in any malathion preparation, but especially one developed for pharmaceutical use, should be reduced as much as possible. Moreover, given that malathion breaks down into toxic by-products during storage, it is also desirable to prepare malathion which is storage stable.

Many of these malathion impurities have been found to be toxic. MeOOSPO and MeOSSPO can cause liver damage (Keadtisuke et al., *Toxicology Letters* 52:35-46 (1990)), or immune suppression (Rodgers et al., *Immunopharmacology* 17:131-140 (1989)). Isomalathion has been shown to cause death in people after spraying during insect eradication programs. (Aldridge et al., *Archives Toxicology* 42:95-106 (1979)). The toxicity of isomalathion is due to its ability to inhibit acetylcholinesterase; in fact, isomalathion is approximately 1,000 times as active against acetylcholinesterase as compared with malathion. (Berkman et al. Synthesis of Chiral Malathion and Malathion, *Terahedron Letters* 33(11): 1415-1418 (1992)). O,O-methyl,ethyl-S-(1,2-dicarboethoxy)ethyl-phosphorodithioate, isomalathion and MeOOSPO all exhibit pulmonary toxicity and can cause death from hypoxia. (Imamura et al., *Pharmacology and Therapeutics* 38(3):419-427 (1988)). Malaoxon inhibits cholinesterase enzymes. (Umetsu et al., *J. Agric. Food Chem.*, 25:946-953 (1977)). Diethyl fumarate can cause contact urticaria. (Maibach, *Contact Dermatitis* 12(3):139-140 (1985)). Malathion's physical properties make it difficult to remove impurities by conventional means. For example, because malathion is a liquid at ambient temperature (melting point=2.9° C.), crystallization is difficult. Malathion also has a high boiling point (156-157° C.), consequently, distillation also has its problems, especially as malathion is unstable at elevated temperatures.

We have now developed a novel method for synthesizing and purifying malathion for pharmaceutical use. The malathion prepared by the methods of this invention has significantly lower levels of toxic impurities such as isomalathion when compared with other, commercially available malathion preparations that are currently used for pharmaceutical purposes. Moreover, because malathion is known to be unstable, the levels of toxic impurities, e.g., isomalathion, are known to increase over time, there is a need to develop a stable form of malathion. The malathion of the present invention is storage stable, i.e., even after storage at elevated temperature and humidity, the levels of toxic impurities do not increase significantly.

SUMMARY OF THE INVENTION

The methods of the invention provide for a process for preparing malathion, comprising, the steps of (a) preparing a solution of O,O-dimethyldithiophosphoric acid in an organic solvent, selected from the group consisting of toluene, xylene and benzene; (b) extracting the O,O-dimethyldithiophosphoric acid into water to generate an aqueous solution of O,O-dimethyldithiophosphoric acid; (c) reacting the aqueous solution of O,O-dimethyldithiophosphoric acid with diethyl maleate to form malathion; and, (d) treating the malathion from step (c) with a sulfur reagent, wherein the sulfur reagent has a pH less than about 7.0. 2. In one embodiment, the organic solvent is toluene.

The O,O-dimethyldithiophosphoric acid in step (a) may be prepared by the steps comprising, the steps of: (i) adding phosphorous pentasulfide ($P_2S_5$) to toluene to form a suspension; (ii) heating the suspension to about 60° C.; (iii) adding methanol to the suspension; (iv) stirring the suspension after addition of the methanol for at least about 1 hour, while maintaining the temperature of the suspension from about 55° C. to about 60° C.; (v) filtering the suspension from step (iv) after cooling to about 18° C. to about 25° C.; and, (vi) subjecting the suspension from step (v) to vacuum distillation.

The malathion from step (d) may be isolated after treatment with the sulfur reagent. The ratio of water to O,O-dimethyldithiophosphoric acid in step (b) may be about 1:1 to about 10:1 (w/w). In one embodiment, the ratio of water to O,O-dimethyldithiophosphoric acid is about 3:1 (w/w).

The solution of O,O-dimethyldithiophosphoric acid in step (a) may be filtered before extraction into water in step (b). Alternatively, the solution of O,O-dimethyldithiophosphoric acid in step (a) is distilled before extraction into water in step (b).

In one embodiment, the molar ratio of diethyl maleate to O,O-dimethyldithiophosphoric acid in step (c) is about 1:1 to about 2:1. In another embodiment, the molar ratio of diethyl maleate to O,O-dimethyldithiophosphoric acid in step (c) is about 1:1.

A polymerization inhibitor may be added to step (c) during the reaction of the aqueous solution of O,O-dimethyldithiophosphoric acid with the solution of diethyl maleate. The molar ratio of diethyl maleate to the polymerization inhibitor may be about 50:1 to about 500:1. In one embodiment, the molar ratio of diethyl maleate to polymerization inhibitor is about 300:1. The polymerization inhibitor may be hydroquinone.

The sulfur reagent is selected from the group consisting of alkali metal bisulfites and alkaline earth metal bisulfites. In one embodiment, the sulfur reagent is sodium bisulfite. In another embodiment, the sulfur reagent comprises a 20% sodium bisulfite solution having a pH from about 6.1 to about 6.3. The malathion in step (d) may be treated with the 20% sodium bisulfite solution for about 2 hours.

After treatment with the 20% sodium bisulfite solution, the malathion may be washed with water, a 5% NaOH solution and at least two more times with water. After washing with these solutions, the malathion may be assayed for the presence of at least one impurity selected from the group consisting of MeOOSPS, malaoxon, diethyl fumarate, dimethyl malathion, methyl malathion, isomalathion and O,O-methyl, ethyl S-(1,2-dicarboethoxy)ethyl phosphorodithioate, and combinations thereof. In addition, the malathion is assayed for purity. If the malathion at step contains greater than about 5.0% (w/w) diethyl fumarate, the washing steps with water, NaOH and again with water may be repeated as discussed above prior to isolating the malathion.

The malathion prepared as above may be further purified by the steps of: (1) adding water to the malathion; (m) subjecting the malathion from step (k) to azeotropic distillation; (n) repeating steps (l) to (m) at least one (1) time; and, (o) isolating the malathion. The ratio of water to malathion in step (l) ranges from about 2:1 (w/w) to about 10:1 (w/w). In one embodiment, the ratio of water to malathion in step (l) is about 3:1 (w/w). After azeotropic distillation, the malathion is assayed for the presence of at least one impurity selected from the group consisting of MeOOSPO, MeOSSPO, malaxon, MeOOSPS, diethyl fumarate, dimethyl malathion, methyl malathion, O,O-methyl, ethyl S-(1,2-dicarboethoxy)ethyl phosphorodithioate, tetraethyl dithiosuccinate, isomalathion, malathion carboxylic acid, mercaptosuccinate, tetraethyl thiodisuccinate and combinations thereof. In addition, the malathion is assayed for purity. Steps (l) to (o) are repeated if the malathion has greater than about 0.2% (w/w) MeOOSPS, greater than about 0.1% (w/w) malaoxon, greater than about 0.2% (w/w) diethyl furnarate, greater than about 0.2% (w/w) dimethylmalathion, greater than about 0.3% (w/w) methylmalathion, greater than about 0.1% (w/w) isomalathion, or there is less than about 98.5% (w/w) malathion.

The malathion prepared by the process of the invention comprises the following embodiments: (i) greater than about 98.5% (w/w) malathion, less than about 0.1% (w/w) MeOOSPO, less than about 0.1% (w/w) MeOSSPO, less than about 0.2% (w/w) MeOOSPS, less than about 0.3% (w/w) malathion carboxylic acid and less than about 0.1% (w/w) isomalathion; (ii) greater than about 98.5% (w/w) malathion, less than about 0.1% (w/w) MeOOSPO, less than about 0.1% (w/w) MeOSSPO, less than about 0.2% (w/w) MeOOSPS, less than about 0.3% (w/w) malathion carboxylic acid and less than about 0.02% (w/w) isomalathion; (iii) greater than about 99.0% (w/w) malathion, less than about 0.1% (w/w) MeOOSPO, less than about 0.1% (w/w) MeOSSPO and less than about 0.1% (w/w) MeOSSPS, 0.03% (w/w) malathion carboxylic acids and less than about 0.02% (w/w) isomalathion; and, (iv) greater than about 99.0% (w/w) malathion, less than about 0.04% (w/w) MeOOSPO, less than about 0.02% (w/w) MeOSSPO and less than about 0.1% (w/w) MeOSSPS, 0.03% (w/w) malathion carboxylic acids and less than about 0.02% (w/w) isomalathion.

The malathion prepared by the process of this invention is stable after storage. Specifically, after storage at 5° C. for 3 months the amount of isomalathion is not more than about 0.1% (w/w). After storage for 3 months at 25° C. and 60% relative humidity, the amount of isomalathion is not more than about 0.1% (w/w). After storage for 3 months at 30° C. and 60% relative humidity, the amount of isomalathion is not more than about 0.1% (w/w).

DETAILED DESCRIPTION OF THE INVENTION

The present invention provides a process for preparing a highly purified form of malathion that may be used for pharmaceutical formulations. Malathion is synthesized by (a) preparing a solution of O,O-dimethyldithiophosphoric acid in an organic solvent; (b) extracting the O,O-dimethyldithiophosphoric acid into water to generate an aqueous solution of O,O-dimethyldithiophosphoric acid; (c) reacting the aqueous solution of O,O-dimethyldithiophosphoric acid with diethyl maleate to form malathion; and, (d) treating the malathion from step (c) with a sulfur reagent, wherein the sulfur reagent has a pH less than about 7.0.

The O,O-dimethyldithiophosphoric acid in step (a) may be produced by (i) suspending phosphorus sulfide in an organic solvent, (ii) adding methanol to the phosphorous sulfide suspension drop-wise and, (iii) mixing the phosphorous sulfide suspension. A phosphorus sulfide is a compound of formula $P_xS_y$, wherein x and y are integers. Examples of phosphorus sulfides include compounds such as phosphorus pentasulfide ($P_2S_5$), tetraphosphorus heptasulfide ($P_4S_7$) as well as mixtures of these compounds. Phosphorus pentasulfide is usually found as a dimer, tetraphosphorus decasulfide ($P_4S_{10}$) (the term phosphorus pentasulfide includes, the dimer, tetraphosphorus decasulfide). In one embodiment, the phosphorus sulfide is phosphorus pentasulfide. Any suitable organic solvent may be used to suspend the phosphorus sulfide. Suitable organic solvents such as toluene, xylene and benzene as well as mixtures may be used. In a preferred embodiment, toluene is used as the organic solvent for suspending the phosphorous sulfide.

Because higher temperatures cause decomposition of O,O-dimethyldithiophosphoric acid as well as formation of undesirable byproducts, the temperature of the step where the phosphorous sulfide suspension is mixed (step (iii), above) is controlled. Mixing may proceed for approximately 1 hour, while maintaining the temperature of the reaction vessel between about 55° C. to about 65° C. with nitrogen ($N_2$) bubbling. After mixing, the reaction mixture is cooled to a temperature of about 18° C. to about 25° C.

Prior to extraction into water, the solution of O,O-dimethyldithiophosphoric acid in an organic solvent may be further purified by filtration, distillation or evaporation. Filtration removes insoluble impurities such as any un-reacted solids, e.g., $P_2S_5$. Other suitable methods of removing insoluble impurities, include, decantation and centrifugation.

The solution of O,O-dimethyldithiophosphoric acid in the organic solvent may be concentrated or purified by distillation. Preferably, the solution of O,O-dimethyldithiophosphoric acid in the organic solvent is distilled by azeotropic distillation. An advantage of distillation (e.g., azeotropic distillation) is that it effectively removes MeOOSPS without generating the isomerization products of malathion and isomalathion. Distillation may be performed under vacuum. Distillation removes volatile impurities such as, hydrogen sulfide ($H_2S$) as well as any unreacted methanol or other organic solvents, e.g., toluene. If hydrogen sulfide is present in the O,O-dimethyldithiophosphoric acid, it can react with diethyl maleate or diethyl fumarate to form diethyl 2-mercaptosuccinate. Diethyl 2-mercaptosuccinate can be oxidized to form a dimeric impurity, tetraethyl dithiodisuccinate, which is very difficult to remove from any malathion preparation.

Another advantage of the distillation (e.g., azeotropic distillation) is to effectively remove unreacted methanol. If unreacted methanol is present as an impurity in the O,O-dimethyldithiophosphoric acid, it can react with malathion to form both methanolysis and transesterification impurities. Methanolysis impurities include, O,O,O,-trimethylthiophosphoric acid (MeOOOPS) and O,O,S-trimethylthiophosphoric acid (MeOOSPO). Transesterification impurities include, [(dimethoxyphosphinothioyl)thio]butanedioic acid dimethyl ester (dimethyl malathion), 1-carboethoxy-2-carbomethoxy-1-[(dimethoxyphosphinothioyl)thio]ethane, and 2-carboethoxy-1-carbomethoxy-1-[(dimethoxyphosphinothioyl)thio] ethane; 1-carboethoxy-2-carbomethoxy-1-[(dimethoxyphosphinothioyl)thio]ethane, and 2-carboethoxy-1-carbomethoxy-1-[(dimethoxyphosphinothioyl)thio]ethane are collectively referred to as methyl malathion. These impurities are difficult to remove from the malathion preparation.

Another advantage of the distillation process is to remove dissolved $H_2S$. If $H_2S$ is present, it will react with diethyl maleate to afford diethyl 2-mercaptosuccinate and dimerize to form tetraethyl dithiodisuccinate.

Typically, the distillation step removes a portion of the organic solvent, e.g., toluene xylene or benzene, together with other volatile impurities such as methanol. After distillation, the concentration of the O,O-dimethyldithiophosphoric acid in the solution is about 30% (w/w) to about 70% (w/w); more preferably, the concentration of the O,O-dimethyldithiophosphoric acid in solution may be about 50% (w/w). Preferably, the distillation may be performed at reduced pressure, e.g., less than about 1 atmosphere (1 atmosphere=760 mm Hg). In another embodiment, the distillation may be performed at a pressure of about 0.5 atmosphere, while in a third embodiment, the distillation may be performed at a pressure of about 0.2 atmosphere.

After the distillation, evaporation or filtration step, the O,O-dimethyldithiophosphoric acid in the organic solvent is extracted into water to yield an aqueous solution of O,O-dimethyldithiophosphoricacid. An advantage of the present invention is that extraction of the O,O-dimethyldithiophosphoric acid into water significantly removes MeOOSPS. Analysis by gas chromatography of the O,O-dimethyldithiophosphoric acid in the organic solvent before extraction with the water indicates that the O,O-dimethyldithiophosphoric acid is contaminated with up to about 25-30% (w/w) of O,O, S-trimethyl phosphorodithioate (MeOOSPS) as well as with other impurities, such as, O,O,S-trimethyl phosphorothioate (MeOOSPO). After extraction with water, gas chromatography analysis indicates that the quantity of O,O,S-trimethyl phosphorodithioate (MeOOSPS) in the aqueous solution of O,O-dimethyldithiophosphoric acid is reduced to about 5-6% (w/w) or less.

Any suitable quantity of water may be used for the extraction. The ratio of water to the organic solution of O,O-dimethyldithiophosphoric acid may be from about 1:1 to about 10:1 (w/w); preferably, the ratio is about 3:1 (w/w). More preferably, the ratio of the solution of O,O-dimethyldithiophosphoric acid in the organic solvent to water may be about 1:1. Mixing of the water and the solution of O,O-dimethyldithiophosphoric acid in the organic solvent produces a reaction mixture containing two layers, an organic and an aqueous layer. After separation of the organic and aqueous layers, the aqueous layer which now contains the O,O-dimethyldithiophosphoric acid may be washed with toulene. The aqueous solution of O,O-dimethyldithiophosphoric acid is then reacted with a diethyl maleate to form malathion. Diethyl fumarate may also be used in the reaction with the aqueous solution of O,O-dimethyldithiophosphoric acid to form malathion. Because diethyl maleate is not miscible with an aqueous solvent such as water, the reaction is performed as a heterogeneous, two layer mixture containing an aqueous layer (the aqueous solution of O,O-dimethyldithiophosphoric acid) and organic layer (diethyl maleate or diethyl fumarate). The two-phase mixture is subjected to mechanical mixing. Malathion collects in the lower or organic phase. The above reaction is done by direct addition of diethyl maleate to the aqueous solution of O,O-dimethyldithiophosphoric acid. An advantage of the present invention is that there is no need to isolate the O,O-dimethyldithiophosphoric acid in a concentrated form. O,O-dimethyldithiophosphoric acid is poisonous, thus, direct addition avoids the need to isolate any toxic compounds during the formation of malathion.

In order to maximize the yield and purity of the malathion, the conditions for reacting the aqueous solution of O,O-dimethyldithiophosphoric with the diethyl maleate, e.g., reaction temperature, reaction time, reagent ratio, may be optimized by those of ordinary skill in the art. In one embodiment, the molar ratio of diethyl maleate to O,O-dimethyldithiophosphoric acid may be from about 1:1 to about 2:1. The reaction temperature may range from about 25° C. to about 70° C.; more preferably, the reaction temperature is about 40° C. to about 65° C.; still more preferably, the reaction temperature is about 53° C. The reaction time may vary, e.g., (i) from about two (2) to about twelve (12) hours, (ii) from about five (5) to about ten (10) hours, or, (iii) about eight (8) hours. The reaction may be performed under a $N_2$ atmosphere. After completion of the reaction, the two solutions, the aqueous solution of O,O-dimethyldithiophosphoric and the diethyl maleate, are cooled to about 18° C. to about 25° C. temperature, the solutions separated and the diethyl maleate which contains the malathion washed at least two more times with water.

Diethyl fumarate may be formed during the reaction of the aqueous solution of O,O-dimethyldithiophosphoric acid with diethyl maleate. In order to decrease polymerization of diethyl maleate and diethyl fumarate, the reaction may be performed in the presence of a polymerization inhibitor. Suitable polymerization inhibitors include hydroquinone. The molar ratio of diethyl maleate to polymerization inhibitor is about 50:1 to about 500:1. For example, in one embodiment, the molar ratio of diethyl maleate to polymerization inhibitor is about 300:1.

In order to further purify the malathion, the diethyl maleate containing the malathion may be treated with a sulfur solution. The inventors of the present invention surprisingly found that a sulfur solution with a pH of less than about 7 is effective to eliminate dimer impurity formation. The pH of the sulfur solution ranges from about 6.0 to about 7.0. The sulfur solution may be for example, a (i) bisulfite, such as, sodium bisulfite, sodium metabisulfite, magnesium bisulfite or ammonium bisulfite, (ii) sulfite, such as, sodium sulfite, potassium sulfite, magnesium sulfite or ammonium sulfite, or (iii) sulfide such as, sodium sulfide, potassium sulfide, calcium sulfide, ammonium sulfide or ammonium bisulfide. The acidic, aqueous sulfur solution may be prepared in any suitable manner (note, an aqueous solution of a bisulfite is inherently acidic); suitable methods for preparing an acidic aqueous solution of a bisulfite include dissolving a bisulfite in water. Aqueous solutions of sulfites or sulfides are inherently basic. Therefore, an acidic, aqueous solution of a sulfite or sulfide may be prepared by dissolving a sulfite in water, followed by addition of an acid, such as, hydrochloric acid or sulfuric acid, to reduce the pH below 7.0. An advantage of the acidic sulfur solution is that it effectively increases the purity of malathion. The importance of using an acidic sulfur solution to further purify the malathion was demonstrated by the fact that if the malathion was treated with a basic solution (i.e., pH>7.0) of sulfites or sulfides, the resulting malathion was found to be contaminated with greater than 0.2% (w/w) tetraethyl dithiodisuccinate. In contrast, if the pH of the aqueous, sulfur solution was acidic, i.e., pH below 7.0, the malathion formed contained less than 0.2% (w/w) tetraethyl dithiodisuccinate. At pH 7-12, treatment of malathion with sulfur solution may also cause formation of tetraethyl thiodisuccinate impurity. An additional advantage of using acidic sulfur solution is to avoid malathion decomposition, which is known to occur more likely at a basic pH (i.e., pH>7). (See, e.g., Cotham W E Jr., et al. *Food Chem.* 37:824-828 (1989)).

In one embodiment, the diethyl maleate, which contains the malathion, is treated with a 20% (w/w) solution of sodium bisulfite (pH from about 6.1 to about 6.3). After mixing the diethyl maleate with the 20% (w/w) sodium bisulfite solution at about 60° C. for about 2 hours, the mixture containing the two solutions, diethyl maleate and 20% (w/w) sodium bisulfite, is cooled to about 18° C. to about 25° C. and the two solutions are then separated. The diethyl maleate is then washed with water and the two solutions, the diethyl maleate and water, separated; the diethyl maleate is then washed with a 5% (w/w) NaOH and the solutions separated. After washing with the NaOH, the diethyl maleate may be washed at least two (2) more times with water as described above.

At this stage of the purification, the purity of the malathion may be assayed by high pressure liquid chromatography (HPLC). Other techniques for assaying the purity of malathion and for determining the presence of impurities include, gas chromatography (GC), and nuclear magnetic resonance (NMR) spectroscopy (WHO Specifications and Evaluations for Public Health Pesticides: Malathion, World Health Organization, 2003). Using these analytical techniques, the presence of the following impurities may be determined, MeOOSPS, malaoxon, diethyl fumarate, dimethyl malathion, methyl malathion, isomalathion, O,O-methyl, ethyl S-(1,2-dicarboethoxy)ethyl phosphorodithioate, O,O-methyl, ethyl S-(1,2-dicarboethoxy)ethyl phosphorodithioate; in addition, the presence of any other detectable impurity may be determined using this methodology.

If the malathion contains greater than 5% (w/w) diethyl fumarate, the malathion is reprocessed by treating it again with the sulfur solution (pH 6.0-7.0), 5% (w/w) NaOH and water, sequentially, as described above. After reprocessing, the resulting malathion is assayed by HPLC for both the purity of malathion and for the presence of any of the impurities listed above.

At this stage of the purification, the malathion may exhibit the following purity/impurity profile: (i) greater than about 98.5% (w/w) malathion; (ii) less than about 5.0% (w/w) diethyl fumarate, and (iii) less than about 0.1% (w/w) isomalathion. In a preferred embodiment, the malathion may have the following purity/impurity profile: (i) greater than about 98.5% (w/w) malathion, (ii) less than about 0.2% (w/w) MeOOSPS, (iii) less than about 0.1% (w/w) malaoxon, (iv) less than about 0.2% (w/w) diethyl fumarate, (v) less than about 0.3% (w/w) methylmalathion, (vi) less than about 0.1% (w/w) isomalathion, and (vii) less than about 0.3% (w/w) O,O-methyl, ethyl S-(1,2-dicarboethoxy)ethyl phosphorodithioate. In addition, at this stage of the purification, there is not more than about 0.1% (w/w) of any other detectable impurity present in the malathion.

In order to reduce the levels of impurities further, the malathion prepared by the above process or malathion obtained from another synthetic route may be further purified by the distillation with water. Water is added to the malathion and the mixture subjected to azeotropic distillation. An advantage of this azeotropic distillation process is that it effectively removes MeOOSPS without producing the isomerization product of malathion (i.e., isomalathion). Additionally, azeotropic distillation is a more simple process as compared to air stripping or flash distillation. It is also much more effective in removing MeOOSPS. In one embodiment, the ratio of water to malathion is 3:1 (w/w). After the first distillation is completed, water is added, and azeotropic distillation repeated at least one more time. Again, the ratio of water to malathion at this stage in the purification may be about 3:1 (w/w). As long as there is a comparative excess of water present, the ratio of water to malathion may range from about 2:1 to greater than about 10:1 (w/w). After these additional purification steps, addition of water followed by azeotropic distillation, the purity of the malathion is determined by HPLC. The impurities assayed for can include, MeOOSPS, malaoxon, diethyl fumarate, dimethylmalathion, methylmalathion, isomalathion, malathion carboxylic acids as well as any other detectable impurity. If (i) MeOOSPS is greater than about 0.2% (w/w), (ii) malaxon is greater than about 0.1% (w/w), (iii) diethyl fumarate is greater than about 0.2% (w/w), (iv) dimethylmalathion is greater than about 0.2% (w/w), (v) methylmalathion is greater than about 0.3% (w/w), (vi) isomalathion is greater than about 0.1% (w/w), (vii) any other individual detectable impurity is greater than 0.1% (w/w), or (viii) the malathion is less than about 98.5% (w/w), then, additional water is added to the malathion and azeotropic distillation repeated as described above. The purity/impurity profile of the malathion is then assayed a second time. Azeotropic distillation with the addition of water may be repeated until the purity/impurity profile the wet malathion conforms to the criteria set forth above for the purity of the malathion and for the % (w/w) of various impurities.

At this stage of the purification, the malathion may have the following purity/impurity profile:
(i) greater than about 98.5% (w/w) malathion;
(ii) less than about 0.2% (w/w) MeOOSPS;
(iii) less than about 0.1% (w/w) malaxon;
(iv) less than about 0.2% (w/w) diethyl fumarate;
(v) less than about 0.2% (w/w) dimethylmalathion;
(vi) less than about 0.3% (w/w) methylmalathion; or,
(vii) less than about 0.1% (w/w) isomalathion.

Malathion free of water may be obtained by heating the malathion after addition of water, followed by azeotropic distillation at a temperature from about 35° C. to about 45° C., together with air bubbling through the wet mass. The water content may be monitored by the Karl Fisher procedure. United States Pharmacopeia <921>. When the water content is reduced to not more than 0.1% (w/w), the malathion is cooled and filtered to remove any foreign particles. Filtration may be through glass paper.

After drying, the malathion is assayed by HPLC for the purity of malathion as well as for the presence of various impurities, including, MeOOSPO, MeOSSPO, malaxon, MeOOSPS, diethyl fumarate, dimethyl malathion, methyl malathion, O,O-methyl, ethyl S-(1,2-dicarboethoxy)ethyl phosphorodithioate, tetraethyl dithiosuccinate, isomalathion, malathion carboxylic acids such as O,O-dimethyl-S-(1-carboxy-2-carboxyethoxy) ethyl phosphorodithioate or O,O-dimethyl-S-(1-carboxy-2-carboxy) ethyl phosphorodithioate), mercaptosuccinate and tetraethyl thiodisuccinate. The HPLC assay of impurities may include all or only some of the impurities selected from the above list of impurities. In addition, the malathion may also be assayed for the presence of any other detectable impurities.

Various embodiments of malathion are encompassed by the invention including: (i) greater than about 98.5% (w/w) malathion, less than about 0.1% (w/w) MeOOSPO, less than about 0.1% (w/w) MeOSSPO, less than about 0.2% (w/w) MeOOSPS, less than about 0.3% (w/w) malathion carboxylic acid and/or less than about 0.1% (w/w) isomalathion; (ii) greater than about 98.5% (w/w) malathion, less than about 0.1% (w/w) MeOOSPO, less than about 0.1% (w/w) MeOSSPO, less than about 0.2% (w/w) MeOOSPS, less than about 0.3% (w/w) malathion carboxylic acid and/or less than about 0.02% (w/w) isomalathion; (iii) greater than about 99.0% (w/w) malathion, less than about 0.1% (w/w) MeOOSPO, less than about 0.1% (w/w) MeOSSPO and/or less than about 0.1% (w/w) MeOSSPS, 0.03% (w/w) malathion carboxylic acids and less than about 0.02% (w/w) isomalathion; and, (iv) greater than about 99.0% (w/w) malathion, less than about 0.04% (w/w) MeOOSPO, less than about 0.02% (w/w) MeOSSPO and/or less than about 0.1% (w/w) MeOSSPS, 0.03% (w/w) malathion carboxylic acids and less than about 0.02% (w/w) isomalathion.

The malathion prepared by the process of the invention was tested for storage stability. Malathion prepared by the process of the invention was stored under a variety of different temperature and humidity conditions for up to three (3) months. The storage conditions were:
(i) 5° C., (ii) 25° C., 60% relative humidity and (iii) 30° C. and 60% relative humidity. The purity of the sample was determined after storage using HPLC. After storage, the malathion prepared by the process of the invention exhibits the following with respect to isomalathion and malathion:
(i) less than about 0.1% (w/w) isomalathion and greater than 98.5% (w/w) malathion after storage at 5° C. for 3 months;
(ii) less than about 0.1% (w/w) isomalathion and greater than about 98.5% (w/w) malathion after storage for 3 months at 25° C. and 60% relative humidity; and,
(iii) less than about 0.1% (w/w) isomalathion and greater than about 98.5% (w/w) malathion after storage for 3 months at 30° C. and 60% relative humidity.

The malathion prepared by the process of the invention may be used for the preparation of malathion formulations such as Ovide® lotion and gels (see, U.S. Patent Application No. PCT/US05/24643 and 24558), lotions, creams or solutions.

The invention is further illustrated, but not limited by, the following examples.

EXAMPLE 1

Preparation of Dimethyl Dithiophosphoric Acid

Phosphorus pentasulfide (1.4 kg) and toluene (1.4 L) were combined under nitrogen in a 5-L jacketed glass reactor equipped with mechanical stirrer, and the resulting suspension was heated with stirring to about 60° C. Methanol (1.1 L) was added dropwise over the course of four (4) hours and fifteen (15) minutes, while maintaining the temperature of the reaction mass at 67° C. or lower. The resulting gaseous $H_2S$ was trapped using an aqueous solution of sodium hypochlorite/sodium hydroxide. After complete addition of the methanol, the mixture was stirred at 55-65° C. for an additional one (1) hour.

The mixture was cooled to a temperature of 22-30° C. and the mixture was filtered to remove unreacted phosphorus pentasulfide. Additional toluene (0.3 L) was added to the resulting filtrate. The mixture was distilled under vacuum (≦200 mbar) at a temperature of about 50-60° C. to remove about 600 mL of toluene. The resulting concentrate was cooled to a temperature of 22-30° C. and water (3 kg) was added. The two phases were mixed for 20 minutes, and then the phases were separated. The aqueous phase was washed with toluene (0.3 L), and the aqueous phase again was separated, to provide an aqueous solution of dimethyldithiophosphoric acid (about 4.22 kg containing about 1.22 kg of dimethyldithiophosphoric acid).

EXAMPLE 2

Preparation of Malathion

The solution of dimethyl dithiophosphoric acid was added to diethyl maleate (the ratio of dimethyl dithiophosphoric acid to diethyl maleate was approximately 1-1.25 kg: 1.2 kg). Hydroquinone (approximately 3 grams) was added to the mixture. The reaction mixture which contains two separate solutions, an organic solution of diethyl maleate and an aqueous solution of dimethyl dithiophosphoric acid, was mixed for about 8 hours at 53° C. under a nitrogen atmosphere. After mixing, the reaction was cooled to ambient temperature and the organic and aqueous solutions were separated. The organic or diethyl maleate solutions which contained malathion was washed two (2) times with water (approximately 1 liter each time). The organic and aqueous solutions were separated and the malathion in the solution of diethyl maleate retained. This reaction yielded approximately 1.5-1.9 kg of malathion.

EXAMPLE 3

Purification of the Malathion

The solution of diethylmaleate (organic) which contained the malathion (approximately 1.5-1.9 kg) was treated with about 4.6 kg of a 20% sodium bisulfite solution (aqueous) (pH 6.1-6.3) at 60° C. for 2 hours. The mixture was cooled to ambient temperature and the organic and aqueous layers separated; the organic layer was washed with water (approximately 1.5 kg). The organic and aqueous layers were separated. The organic layer was then washed with a 0.5% NaOH solution. After separation of the two layers, the organic layer containing the malathion was washed twice with water (approximately 1 liter of water was used for each wash) to yield, approximately 0.75-0.95 kg of malathion. The purity of the malathion at this stage was determined by HPLC. If more than 5% (w/w) diethyl fumarate was present in the malathion, the material was reprocessed by treatment with the sodium bisulfite solution and water. After reprocessing, the malathion was assayed a second time for purity. This reprocessing step could be repeated until the purity profile of the malathion conformed with the diethyl fumarate cut-off set forth above.

EXAMPLE 4

Analysis of Malathion after Purification

The purity of malathion and the percentage of impurities present were determined by HPLC instrument with a variable wavelength detector. The mobile phase composition and/or flow rate were adjusted to meet the chromatographic parameters. The results of the HPLC analyses for two different sample batches of malathion are shown below in Table I.

TABLE I

| HPLC Analysis of Malathion | | |
|---|---|---|
| Analyte | Malathion (%(w/w)) (Batch A) | Malathion (%(w/w)) (Batch B) |
| MeOOSPS | 0.12 | 0.14 |
| Malaoxon | <0.05 | <0.05 |
| Diethyl fumarate | <0.01 | <0.01 |
| Dimethylmalathion | <0.02 | <0.02 |
| Methylmalthion | 0.06 | 0.06 |
| Isomalthion | <0.04 | <0.04 |
| O,O-methyl, ethyl S-(1,2-dicarboethoxy)ethyl phosphorodithioate | 0.18 | 0.12 |
| Any other detectable impurity | 0.10 | <0.04 |
| Malathion Purity | 99.5 | 99.6 |

EXAMPLE 5

Azeotropic Distillation of Malathion

Water (2.8 kg) was added to the malathion formed as described in Example 4 and the resulting two-phase mixture subjected to azeotropic distillation over the course of four days at a temperature of about 35-50° C. and a pressure of about 30-60 mbar. Water was added to the mixture at approximately one-hour intervals to replace the quantity removed by azeotropic distillation during that period (about 0.2-0.7 L each time). A total of about 34.2 L of water was distilled during this process. The two-phase mixture was cooled to 22-30° C., and the phases were separated, providing malathion (0.84 kg) (note, the malathion is wet, i.e., contains water).

The purity of the obtained malathion was determined using HPLC; the results are shown in Table II.

TABLE II

| Analysis of Malathion after Azeotropic Distillation | |
|---|---|
| Compound | Quantity (% w/w) |
| Diethyl fumarate | <0.01 (LOD) |
| Isomalathion | 0.07 |
| MeOOSPS | 0.1 |
| Malaoxon | <0.05 (LOD) |
| Dimethyl malathion | <0.02 (LOD) |
| Methyl malathion | 0.06 |
| Malathion purity | 99.5 |

These data demonstrate that at least 97% (w/w) of the MeOOSPS was removed from the malathion of Example 3. These data further demonstrate that the purified malathion contained only 0.07% (w/w) of isomalathion.

EXAMPLE 6

Analysis of Sample Batches of Malathion Prepared by the Process of this Invention In Table III set forth below, three different batches of malathion prepared by the process of the invention (these batches are noted in the table as A, B and C) were analyzed after drying by HPLC for malathion purity and for the presence of impurities as set forth above. As a comparison, the following samples of malathion were analyzed, malathion approved for pharmaceutical use from the United States Pharmacopeia ("USP") and malathion used for pharmaceutical preparations obtained from Cheminova (referered to herein as, Cheminova A/S, Thyborønvej 78 DK-7673 Harboøre, Denmark). The purity of these samples, USP and Cheminova, was compared with the purity of the malathion prepared by the process of the invention. The results of the analysis are shown in Table III.

TABLE III

HPLC Analysis of Malathion Prepared by the Process of the Invention after Drying and Comparison with Malathion from the USP and Cheminova***

| Batch | Malathion | MeOOSPO | MeOSSPO | Malaxon | MeOOSPS | Diethyl Fumarate | Dimethyl Malathion | Methyl Malathion |
|---|---|---|---|---|---|---|---|---|
| A | 99.3 | <0.04 | <0.02 | <0.05 | 0.1 | <0.01 | <0.02 | 0.07 |
| B | 99.2 | <0.04 | <0.02 | <0.05 | 0.1 | <0.01 | <0.02 | 0.07 |
| C | 99.2 | <0.04 | <0.02 | <0.05 | 0.2 | <0.01 | <0.02 | 0.06 |
| USP |  | <0.04 | 0.04 | <0.05 | 0.09 | 0.05 | <0.02 | 0.17 |
| I*** |  | 0.05 | <0.02 | <0.05 | 0.05 | 0.02 | <0.02 | 0.2 |
| II*** |  | 0.05 | <0.02 | 0.07 | 0.06 | <0.02 | <0.02 | 0.1 |
| III*** |  | 0.06 | <0.02 | <0.05 | 0.04 | 0.02 | <0.02 | 0.2 |

| Batch | O,O methyl, ethyl S-(1,2-dicarboethoxy)ethyl phosphorodithioate | Tetraethyl dithiodi-succinate | Isomalathion | Malathion Carboxylic Acids | Mercapto Succinate | Tetraethyl thiodi-succinate |
|---|---|---|---|---|---|---|
| A | 0.1 | 0.05 | <0.02 | <0.03 | 0.01 | ND* |
| B | 0.1 | 0.06 | <0.02 | <0.03 | 0.01 | ND |
| C | 0.1 | 0.05 | <0.02 | <0.03 | 0.01 | ND |
| USP | 0.14 | <0.03 | 0.27 | 0.77 | 0.04 | ND |
| I*** | — | — | 0.2 | — | — | — |
| II*** | — | — | 0.2 | — | — | — |
| III*** | — | — | 0.2 | — | — | — |

*ND—not detected
**all numbers presented as (w/w)%
***I-III commercial sample of pharmaceutical grade malathion obtained from Cheminova. Samples were stored for at least 1 year under proper storage conditions prior to analysis.

When compared with the USP malathion, malathion prepared by the methods of the present invention has less isomalathion, <0.02% (w/w) versus 0.27% (w/w) USP malathion. In addition, there is less (i) MeOSSPO present, <0.02% (w/w), malathion prepared by the methods of the present invention, versus 0.04% (w/w), USP malathion, (ii) diethyl fumarate, <0.01% (w/w), malathion prepared by the methods of the present invention, versus 0.05% (w/w), USP malathion, (iii) methyl malathion, 0.06-0.07% (w/w), malathion prepared by the methods of the present invention versus 0.17% (w/w), USP malathion, (iv) malathion carboxylic acids, <0.03% (w/w), malathion prepared by the methods of the present invention versus 0.77% (w/w), USP malathion, and mercapto succinate, 0.01% (w/w), malathion prepared by the methods of the present invention versus 0.04% (w/w), USP malathion.

When compared with malathion from Cheminova, malathion prepared by the methods of the present invention has less isomalathion, <0.02% (w/w) versus 0.2% (w/w) malathion from Cheminova. In addition, there is less (i) MeOOSPO present, <0.02% (w/w), malathion prepared by the methods of the present invention, versus 0.05% (w/w), USP malathion, (ii) diethyl fumarate, <0.01% (w/w), malathion prepared by the methods of the present invention, versus 0.02% (w/w), malathion from Cheminova, and, (iii) methyl malathion, 0.06-0.07% (w/w), malathion prepared by the methods of the present invention versus 0.1-0.2% (w/w), malathion from Cheminova.

Embodiments of malathion at this stage of the purification include:

(i) greater than about 98.5% (w/w) malathion, less than about 0.1% (w/w) MeOOSPO, less than about 0.1% (w/w) MeOSSPO, less than about 0.1% (w/w) malaxon, less than about 0.2% (w/w) MeOOSPS, less than about 0.2% (w/w) diethyl fumarate, less than about 0.3% (w/w) methyl malathion, and/or less than about 0.1% (w/w) isomalathion;

(ii) greater than about 98.5% (w/w) malathion, less than about 0.1% (w/w) MeOOSPO, less than about 0.1% (w/w) MeOSSPO, less than about 0.1% (w/w) malaxon, less than about 0.2% (w/w) MeOOSPS, less than about 0.2% (w/w) diethyl fumarate, less than about 0.3% (w/w) methyl malathion, less than about 0.3% (w/w) O,O methyl, ethyl S-(1,2-dicarboethoxy)ethyl phosphorodithioate, less than about 0.3% (w/w) malathion carboxylic acids and/or less than about 0.1% (w/w) isomalathion;

(iii) greater than about 99.0% (w/w) malathion, less than about 0.1% (w/w) MeOOSPO, less than about 0.1% (w/w) MeOSSPO, less than about 0.1% (w/w) malaxon, less than about 0.2% (w/w) MeOOSPS, less than about 0.2% (w/w) diethyl fumarate, less than about 0.3% (w/w) methyl malathion, and/or less than about 0.1% (w/w) isomalathion;

(iv) greater than about 99.0% (w/w) malathion, less than about 0.1% (w/w) MeOOSPO, less than about 0.1% (w/w) MeOSSPO, less than about 0.1% (w/w) malaxon, less than about 0.2% (w/w) MeOOSPS, less than about 0.2% (w/w) diethyl fumarate, less than about 0.3% (w/w) methyl malathion, less than about 0.3% (w/w) O,O methyl, ethyl S-(1,2-dicarboethoxy)ethyl phosphorodithioate, less than about 0.3% (w/w) malathion, less than about 0.3% (w/w) malathion carboxylic acids (O,O-dimethyl-S-(1-carboxy-2-carboxyethoxy) ethyl phosphorodithioate and/or O,O-dimethyl-S-(1-carboxy-2-carboxy) ethyl phosphorodithioate) less than 0.1% (w/w) isomalathion;

(v) greater than about 99.0% (w/w) malathion, less than about 0.1% (w/w) isomalathion and/or less than about 0.3% (w/w) malathion carboxylic acids;

(vi) greater than about 99.0% (w/w) malathion, less than about 0.02% (w/w) isomalathion and/or less than about 0.03% (w/w) malathion carboxylic acids;

(vii) greater than about 99.0% (w/w) malathion, less than about 0.02% (w/w) isomalathion, less than about 0.03% (w/w) malathion carboxylic acids, less than about 0.1% (w/w) MeOOSPO, less than about 0.1% (w/w) MeOSSPO and/or less than about 0.2% (w/w) MeOSSPS; and, (viii) greater than about 99.0% (w/w) malathion, less than about 0.02% (w/w) isomalathion, less than about 0.03%

(w/w) malathion carboxylic acids, less than about 0.04% (w/w) MeOOSPO, less than about 0.02% (w/w) MeOSSPO and/or less than about 0.1% (w/w) MeOSSPS. Additionally, in any of the above embodiments, there may be less than 0.1% (w/w) of any other detectable impurity present in the malathion at this stage of the purification.

EXAMPLE 7

Storage Stability of Malathion

Table IV presents the analytical data showing storage of two, different batches of malathion after storage under a variety of different conditions.

TABLE IV

Analysis of Malathion Prepared by the Process of the Invention after Storage under Different Conditions for 3 Months*

| Compound | Baseline** | Storage at 5° C. | Storage at 25° C., 60% relative humidity | Storage at 30° C. and 60% relative humidity | Storage at 40° C. and 75% relative humidity |
|---|---|---|---|---|---|
| (a) Batch I | | | | | |
| MeOOSPO | <0.04 | <0.04 | <0.04 | <0.04 | 0.05 |
| MeOSSPO | <0.02 | <0.02 | <0.02 | <0.02 | <0.02 |
| MeOOSPS | 0.1 | 0.1 | 0.1 | 0.1 | 0.2 |
| Malaoxon | <0.05 | <0.02 | <0.02 | <0.02 | <0.05 |
| Diethyl fumarate | <0.01 | <0.01 | <0.01 | <0.01 | <0.02 |
| Dimethyl malathion | <0.02 | <0.02 | <0.02 | <0.02 | <0.02 |
| Methyl malathion | 0.06 | 0.06 | 0.06 | 0.06 | 0.06 |
| Isomalathion | 0.06 | <0.05 | 0.04 | 0.06 | 0.1 |
| Malathion Purity | 99.5 | 99.7 | 99.0 | 99.0 | 97.5 |
| (b) Batch II | | | | | |
| MeOOSPO | <0.04 | <0.04 | <0.04 | <0.04 | 0.05 |
| MeOSSPO | <0.02 | <0.09 | <0.02 | <0.02 | <0.02 |
| MeOOSPS | 0.09 | 0.1 | 0.09 | 0.1 | 0.2 |
| Malaxon | <0.05 | <0.05 | <0.05 | <0.05 | <0.05 |
| Diethyl fumarate | <0.06 | <0.01 | <0.01 | <0.01 | <0.02 |
| Dimethyl malathion | <0.02 | <0.02 | <0.02 | <0.02 | <0.02 |
| Methyl malathion | 0.08 | 0.07 | 0.07 | 0.08 | 0.08 |
| Isomalathion | <0.04 | <0.05 | 0.07 | 0.08 | 0.2 |
| Malathion Purity | 99.5 | 99.7 | 99.4 | 99.1 | 97.4 |

*All data is shown as % (w/w)
**Baseline - results at time 0.

Table IV shows the results of the HPLC analysis after three months of storage conditions under these test conditions for two different batches of malathion prepared by the process of this invention.

The invention provides for a malathion characterized by the fact that it is stable after storage under a variety of different conditions. Stability may be characterized by the fact that the levels of isomalathion, MeOOSPO, MeOSSPO and MeOOSPS do not exceed 0.2% (w/w) after storage.

After storage at 5° C. for 3 months, the malathion may have the following purity/impurity profile, greater than about 98.5% (w/w) malathion, less than about 0.1% (w/w) MeOOSPO, less than about 0.1% (w/w) MeOSSPO, less than about 0.1% (w/w) malaxon, less than about 0.2% (w/w) MeOOSPS, less than about 0.2% (w/w) diethyl fumarate, less than about 0.2% (w/w) dimethylmalathion, less than about 0.3% (w/w) methylmalathion and/or less than about 0.1% (w/w) isomalathion. In another embodiment, the profile for the malathion after storage at 5° C. for 3 months is greater than about 99.7% (w/w) malathion, less than about 0.04% (w/w) MeOOSPO, less than about 0.02% (w/w) MeOSSPO, less than about 0.05% (w/w) malaxon, less than about 0.1% (w/w) MeOOSPS, less than about 0.01% (w/w) diethyl fumarate, less than about 0.02% (w/w) dimethylmalathion, less than about 0.06% (w/w) methylmalathion and/or less than about 0.05% (w/w) isomalathion.

After storage for 3 months at 25° C., 60% relative humidity the malathion may have the following purity/impurity profile, greater than about 98.5% (w/w) malathion, less than about 0.1% (w/w) MeOOSPO, less than about 0.1% (w/w) MeOSSPO, less than about 0.1% (w/w) malaxon, less than about 0.2% (w/w) MeOOSPS, less than about 0.2% (w/w) diethyl fumarate, less than about 0.2% (w/w) dimethylmalathion, less than about 0.3% (w/w) methylmalathion and/or less than about 0.1% (w/w) isomalathion. In a second embodiment, the malathion has the following profile after storage for 3 months at 25° C., 60% relative humidity, greater than about 99.0% (w/w) malathion, less than about 0.04% (w/w) MeOOSPO, less than about 0.02% (w/w) MeOSSPO, less than about 0.05% (w/w) malaxon, less than about 0.1% (w/w) MeOOSPS, less than about 0.01% (w/w) diethyl fumarate, less than about 0.02% (w/w) dimethylmalathion, less than about 0.06% (w/w) methylmalathion and/or less than about 0.04% (w/w) isomalathion.

After storage for 3 months at 30° C. and 60% relative humidity, the malathion may have the following purity/impurity profile, greater than about 98.5% (w/w) malathion, less than about 0.1% (w/w) MeOOSPO, less than about 0.1% (w/w) MeOSSPO, less than about 0.1% (w/w) malaxon, less than about 0.2% (w/w) MeOOSPS, less than about 0.2% (w/w) diethyl fumarate, less than about 0.2% (w/w) dimethylmalathion, less than about 0.3% (w/w) methylmalathion and/or less than about 0.1% (w/w) isomalathion. In a second embodiment, the malathion has the following profile after storage at 30° C., 60% relative humidity, greater than about 99.0% (w/w) malathion, less than about 0.04% (w/w) MeOOSPO, less than about 0.02% (w/w) MeOSSPO, less than about 0.05% (w/w) malaxon, less than about 0.1% (w/w) MeOOSPS, less than about 0.01% (w/w) diethyl fumarate, less than about 0.02% (w/w) dimethylmalathion, less than about 0.06% (w/w) methylmalathion and/or less than about 0.04% (w/w) isomalathion.

After storage for 3 months at 40° C. and 75% relative humidity, the malathion has the following purity/impurity profile, greater than about 97.0% (w/w) malathion, less than about 0.1% (w/w) MeOOSPO, less than about 0.1% (w/w) MeOSSPO, less than about 0.1% (w/w) malaxon, less than about 0.2% (w/w) MeOOSPS, less than about 0.2% (w/w) diethyl fumarate, less than about 0.2% (w/w) dimethylmalathion, less than about 0.3% (w/w) methylmalathion and/or less than about 0.1% (w/w) isomalathion. In a second embodiment, the malathion has the following purity/impurity profile after storage for 3 months at 40° C., 75% relative humidity, greater than about 97.5% (w/w) malathion, less than about 0.05% (w/w) MeOOSPO, less than about 0.02% (w/w) MeOSSPO, less than about 0.05% (w/w) malaxon, less than about 0.2% (w/w) MeOOSPS, less than about 0.02% (w/w) diethyl fumarate, less than about 0.02% (w/w) dimethylmalathion, less than about 0.06% (w/w) methylmalathion and/or less than about 0.1% (w/w) isomalathion.

EXAMPLE 8

An example of a lotion formulation prepared using malathion prepared by the process of the present invention comprises the following components:

TABLE V

Malathion Lotion

| Ingredient | % (w/w) |
|---|---|
| Isopropyl Alcohol | 70* |
| Terpineol | 12.672 |
| Dipentene | 10.493 |
| Malathion | 0.654 |
| Pine Needle Oil | 0.284 |

*the amount of isopropyl alcohol may be increased so that the sum of all percentages of the various ingredients equals one hundred percent (100%).

The stability of the malathion prepared by the process of the invention in a malathion lotion formulation (Table V) was tested under a variety of different storage conditions. The percentages of impurities under each storage condition were assayed. The results are shown in Table VI. In one embodiment, the malathion in the lotion has the following purity/impurity profile after storage at 5° C. for 3 months, less than about 0.5% (w/w) diethyl fumarate, less than about 0.5% (w/w) methylmalathion, less than about 0.1% (w/w) isomalathion, less than about 0.1% (w/w) malaoxon, and/or less than about 0.5% (w/w) dimethylmalathion. In addition, in this embodiment, there is less than 0.5% (w/w) of any other detectable impurity present. In another embodiment, the malathion in the lotion has the following purity/impurity profile after storage at 5° C. for 3 months, less than about 0.02% (w/w) diethyl fumarate, less than about 0.2% (w/w) methylmalathion, less than about 0.05% (w/w) isomalathion, less than about 0.03% (w/w) malaoxon, and/or less than about 0.03% (w/w) dimethylmalathion.

After storage for 3 months at 25° C., 60% relative humidity, the malathion in the lotion has the following purity/impurity profile, less than about 0.5% (w/w) diethyl fumarate, less than about 0.5% (w/w) methylmalathion, less than about 0.1% (w/w) isomalathion, less than about 0.03% (w/w) malaoxon, and/or less than about 0.03% (w/w) dimethylmalathion. In addition, in this embodiment, there is less than 0.5% (w/w) of any other detectable impurity present. In another embodiment, the malathion in the lotion has the following purity/impurity profile after storage at 5° C. for 3 months, less than about 0.01% (w/w) diethyl fumarate, less than about 0.1% (w/w) methylmalathion, less than about 0.05% (w/w) isomalathion, less than about 0.03% (w/w) malaoxon, and/or less than about 0.03% (w/w) dimethylmalathion.

After storage for 3 months at 30° C. and 60% relative humidity, the malathion in the lotion has the following purity/impurity profile, less than about 0.5% (w/w) diethyl fumarate, less than about 0.5% (w/w) methylmalathion, less than about 0.1% (w/w) isomalathion, less than about 0.03% (w/w) malaoxon, and/or less than about 0.03% (w/w) dimethylmalathion. In this embodiment, there is less than 0.5% (w/w) of any other detectable impurity present. In a second embodiment under these storage conditions (30° C. and 60% relative humidity) the malathion in the lotion has the following purity/impurity profile, less than about 0.02% (w/w) diethyl fumarate, less than about 0.02% (w/w) methylmalathion, less than about 0.05% (w/w) isomalathion, less than about 0.03% (w/w) malaoxon, and/or less than about 0.03% (w/w) dimethylmalathion.

After storage for 3 months at 40° C. and 75% relative humidity, the malathion in the lotion has the following purity/impurity profile, less than about 0.5% (w/w) diethyl fumarate, less than about 0.5% (w/w) methylmalathion, less than about 0.1% (w/w) isomalathion, less than about 0.03% (w/w) malaoxon, and/or less than about 0.03% (w/w) dimethylmalathion. In this embodiment, there is less than 0.5% (w/w) of any other detectable impurity present. Under these storage conditions, in a second embodiment, the malathion in the lotion has the following profile, less than about 0.01% (w/w) diethyl fumarate, less than about 0.04% (w/w) methylmalathion, less than about 0.07% (w/w) isomalathion, less than about 0.03% (w/w) malaoxon, and/or less than about 0.22% (w/w) dimethylmalathion.

TABLE VI

Stability of Malathion in a Malathion Lotion after three (3) months after storage under different conditions

| Compound | Baseline Time 0 | Storage at 5° C. | Storage at 25° C., 60% relative humidity | Storage at 30° C. and 60% relative humidity | Storage at 40° C. and 75% relative humidity |
|---|---|---|---|---|---|
| Malaoxon | <0.1 | <0.03 | <0.03 | <0.03 | <0.03 |
| Diethyl | <0.5 | 0.02 | 0.01 | 0.02 | 0.01 |

TABLE VI-continued

Stability of Malathion in a Malathion Lotion after three
(3) months after storage under different conditions

| Compound | Baseline Time 0 | Storage at 5° C. | Storage at 25° C., 60% relative humidity | Storage at 30° C. and 60% relative humidity | Storage at 40° C. and 75% relative humidity |
|---|---|---|---|---|---|
| fumarate | | | | | |
| Dimethyl malathion | <0.5 | <0.03 | <0.03 | <0.03 | 0.22 |
| Methyl malathion | <0.05 | 0.2 | 0.1 | <0.02 | <0.04 |
| Isomalathion | <0.1 | <0.05 | <0.05 | <0.05 | 0.07 |

EXAMPLE 9

Analytical Methods

MeOOSPO, MeOSSPO, malaxon, MeOOSPS, diethyl fumarate, dimethyl malathion, methyl malathion, O,O-methyl, ethyl S-(1,2-dicarboethoxy)ethyl phosphorodithioate, tetraethyl dithiosuccinate, isomalathion, malathion carboxylic acids, mercaptosuccinate and the tetraethyl thiodisuccinate were assayed for by HPLC. The mobile phase was a mixture of water, acetonitrile and methanol (480:370:150) and one drop of 85% phosphoric acid for each 1000 ml of mobile phase. Method validation was performed and system reproducibility, linearity, repeatability, intermediate precision, recovery of related compounds and sensitivity were assessed according to standard methology (U.S. Pharmacopeia, 2004, U.S. Pharmacopeial Convention, Inc., 12601 Twinbrook Parkway, Rockville, Md. 20852). If necessary, the mobile phase composition and/or flow rate were adjusted to meet the chromatographic parameters. The analytical parameters for various impurities and for malathion is shown below in Table VII.

surrogate and corresponding internal standard). The resolution is the separation of two peaks in terms of their average peak width at base ($t_{R2} > t_{R1}$):

$$\text{Resolution} = \frac{(t_{R2} - t_{R1})}{(w_{b1} + w_{b2})/2} = \frac{2(t_{R2} - t_{R1})}{(w_{b1} + w_{b2})}$$

In the case of two adjacent peaks it may be assumed that $w_{b1} = w_{b2}$, and thus, the width of the second peak may be substituted for the average value: Resolution=$(t_{R2}-t_{R1})/w_{b2}$.

(a) Calculation of Malathion Assay $$\% \text{ Assay (as is) } (w/w) = \frac{Wst \times Ssm \times Ast}{Sst \times Wsm}$$

Wst=Weight of malathion standard in mg
Wsm=Weight of malathion sample in mg
Ssm=Peak area of malathion obtained from malathion sample solution

TABLE VII

Analytical Parameters for Various Impurities and For Malathion

| Compound | Retention Time (min) | Relative Retention Time | Limit of Detection (LOD, %) | Limit of Quantitation (LOQ, %) | Relative Response Factor | Resolution |
|---|---|---|---|---|---|---|
| MeOOSPO | 1.7 | 0.08 | 0.04 | 0.05 | 0.06 | — |
| MeOSSPO | 2.1 | 0.10 | 0.02 | 0.03 | 0.2 | 3.3 |
| Malaoxon | 4.2 | 0.19 | 0.05 | 0.06 | 0.1 | 13.2 |
| MeOOSPS | 6.5 | 0.30 | 0.02 | 0.03 | 1.1 | 10.1 |
| Diethyl fumarate | 7.2 | 0.33 | 0.01 | 0.02 | 8.8 | 2.6 |
| Dimethyl malathion | 8.9 | 0.41 | 0.02 | 0.03 | 1.2 | 5.4 |
| Methyl malathion | 13.8 | 0.63 | 0.03 | 0.04 | 1.1 | 10.5 |
| Malathion | 21.8 | 1.00 | 0.03 | 0.04 | 1.0 | 11.0 |
| ethyl S-(1,2-dicarboethoxy)ethyl phosphorodithioate | 32.6 | 1.58 | 0.02 | 0.03 | 0.9 | — |
| Isomalathion | 5.3 | 0.3 | 0.02 | 0.03 | 0.3 | — |
| Malathion | 19.0 | 1.00 | 0.02 | 0.03 | 1.0 | — |

The limit of detection is the minimum concentration (% w/w) at which the analyte can reliably be detected. The limit of quantitation is the minimum concentration (% w/w) at which the analyte can reliably be quantified. Limits of detection and quantitation were determined by comparing measured signals from samples with known low concentrations of analyte to measured signals from blank samples. The relative response factor is the ratio of slopes provided by calibration curves for analyte and corresponding internal standard (or Sst=Average peak area of malathion obtained from malathion standard solution
Ast=Assay of malathion standard in percent (b) Calculation of Impurity Content % known or unknown impurity (an unknown impurity is one that is detectable, but not chemically characterized)

$(w/w) = (Wst \times Ssm \times Ast)/(Sst \times Wsm \times RRF \times 200)$

Wst=Weight of malathion standard in mg
Wsm=Weight of malathion sample in mg

Ssm=Peak area of impurity obtained from sample solution
Sst=Average peak area of malathion obtained from known impurity standard solution
Ast=Assay of malathion standard in percent
RRF=Relative Response Factor (1.0 for unknown impurities)
Note: For unknown impurities, values of Limit of Detection and Limit of Quantitation as for malathion were used, and relative response factor RRF=1

(c) Calculation of Malathion Purity

% Malathion Purity (w/w)=100−[% (w/w) known impurities+% (w/w) unknown impurities]

(d) Samples were analyzed for the presence of impurities by gas chromatography (GC) instrument with a FID detector. The chromatographic conditions used was: (i) Column—HP-5, 5% Phenyl Methyl Siloxane or equivalent; (ii) Sample introduction inlet—Split; (iii) Inlet temperature—230° C.; (iv) Split ratio—10:1; (v) Carrier Gas—He, constant flow of 3.5 mL/min; (vi) Injection volume—1 μL; (vii) Detection—FID; (viii) Detector temperature—250° C.; (ix) Constant Flow+Make-up Flow—30.0 mL/min; (x) Oven—Initial temperature, 100° C.; (xi) Initial time—8 min; (xii) Rate—25° C.; (xiii) Final temperature—220° C.; (xiv) Final time=7 min; (xv) Run time—19.8 min; and, (xv) Diluent—Acetonitrile.

EXAMPLE 10

Preparation of Impurities for Analytical Assays (a) O,O,S-Trimethyl Phosphorodithioate (MeOOSPS)—

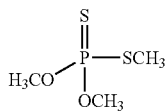

A solution of dimethyl dithiophosphoric acid in toluene was reacted with methyl iodide in the presence of sodium carbonate at ambient temperature and the toluene removed by filtration. The liquid residue was distilled at 130° C. to produce a colorless liquid.

(b) O,S,S-Trimethyl Phosphorodithioate (MeOSSPO)

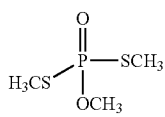

A solution of dimethyl dithiophosphoric acid in a mixture of toluene/acetonitrile was refluxed for 20 hours in the presence of KOH. The potassium salt of S,S-dimethyl phosphorodithioate was precipitated in an ice/water bath. The salt was collected by filtration. After filtration, the salt was suspended in acetonitrile and treated with dimethyl sulfate at the reflux temperature for 6 hours. Water was then added and the mixture refluxed for 1 hour to destroy excess of the methylating agent. The reaction mixture was filtered and the solvent evaporated. The residual residue was extracted into chloroform and the chloroform layer washed with water. The chloroform layer was dried over sodium sulfate and the residue vacuum distilled to yield MeOSSPO.

(c) Trimethyl Phosphorothioate (MeOOSPO)

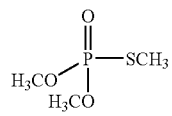

A pre-cooled solution of dimethyl dithiophosphoric acid in toluene was treated with $Cl_2$ while maintaining the reaction temperature between 5-10° C. The mixture was then heated to the reflux temperature for 1.5 hours. After cooling to room temperature, an aqueous solution of KOH was drop wise added to the reaction mixture until a basic (pH>7.0) was achieved. The organic and aqueous layers were separated and the aqueous layer evaporated to dryness. Acetonitrile was added to the solid residue, the mixture filtered and the acetonitrile evaporated. The residual residue was resuspended in acetonitrile and then treated with methyl iodide at ambient temperature for 10 hours. The solvent was evaporated and the residue extracted with ethyl acetate. After extraction, the ethyl acetate was evaporated to dryness. The residual liquid was vacuum distilled to yield MeOOSPO.

(d) Isomalathion

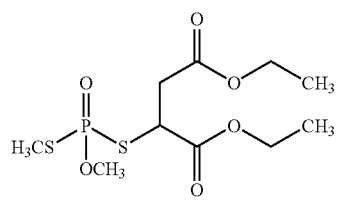

This product is commercially available from the United States Pharmacopeia, Reference Standard (B.No. F1B107) (www.usp.org).

(e) Malaoxon

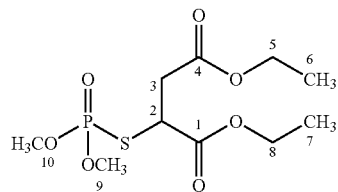

This product is commercially available European Pharmacopoeia Chemical Reference Substance (Ph. Eur. CRS) Malaoxon CRS (Malathion Impurity B), B.No. 2. (www.pheur.org).

(f) Dimethyl Malathion

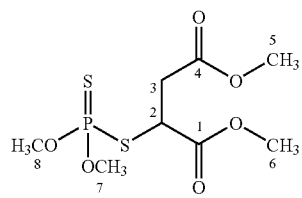

A mixture of malathion, methanol and a catalytic amount of concentrated sulfuric acid was refluxed for 7 hours. After cooling to ambient temperature, the solution was treated with aqueous solution of sodium bicarbonate. The solution was evaporated and extracted into chloroform. The chloroform layer was then filtered. The chloroform layer contained a mixture of malathion, mono-methyl malathion and dimethyl malathion. Dimethyl malathion was isolated by preparative HPLC.

(g) Methyl Malathion

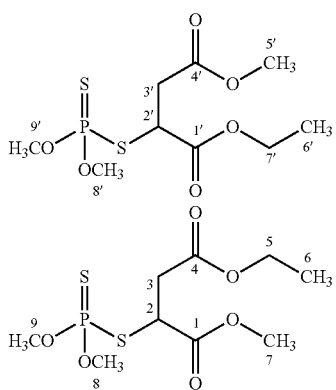

Mono-methyl malathion was isolated by preparative HPLC from the reaction mixture described in (f).

(h) Diethyl Fumarate

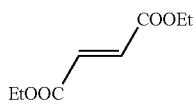

Diethyl Fumarate B.No. DEF M-354, purchased from SigmaAldrich (sigmaaldrich.com).

(i) O,O-dimethyl-S-(1-carboxy-2-carboethoxy) Ethyl Phosphorodithioate and the Corresponding Ethyl Analogue (Malathion Carboxylic Acids)

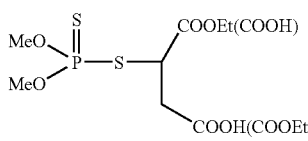

The malathion mono acids were prepared as described by N. Lee Wolfe et al. (*J. Agric. Food Chem.* 23(6):121-1215 (1976)).

(j) O,O-methyl ethyl S-(1,2-dicarboethoxy)ethyl Phosphorodithioate

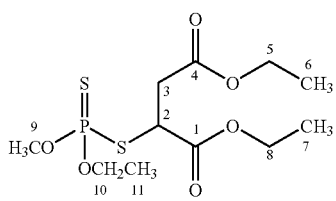

The chemical was prepared by two chemical steps and one purification step.

(i) Step I: Preparation of Dithiolo Acids

Twenty grams of $P_2S_5$ was suspended in toluene. A mixture of 1:1 (v/v) of methanol:ethanol was added drop-wise while maintaining the temperature below 70° C. After addition of the methanol:ethanol, air was bubbled through the reaction mass to remove any dissolved $H_2S$. The mixture was then cooled to ambient temperature and any un-reacted $P_2S_5$ removed by filtration. The toluene solution was extracted with water.

(ii) Step II: Preparation of Crude Malathion Derivatives

The aqueous layer containing the dithiolo acids was treated with diethyl maleate together with hydroquinone at 55° C. After 5 hours, the reaction mass was cooled to ambient temperature and the layers separated. The lower organic layer was washed twice with water and the reaction mixture analyzed by gas chromatography and HPLC. There were three main products: (i) malathion (19.3%); (ii) O,O-methyl ethyl S-(1,2-dicarboethoxy)ethyl phosphorodithioate (38.82%); and, (iii) O,O-diethyl S-(1,2-dicarboethoxy)ethyl phosphorodithioate (8.87%) (data is shown as the % area).

(iii) Step III: Purification of O,O-methyl Ethyl S-(1,2-dicarboethoxy)ethyl Phosphorodithioate The products were isolated by preparative HPLC.

(k) Diethyl 2-mercaptosuccinate

The corresponding mercapto diacid (10 grams) was esterified in 100 ml of absolute ethanol in the presence of 1 gram of sulfuric acid 98% at reflux for 3 hours. The reaction mixture was then cooled to ambient temperature and a major portion of the ethanol removed under reduced pressure. Water and ethylacetate were added to the residue. The layers were separated and the organic solvent removed to yield a colorless product with a purity by gas chromatography of 96% (w/w).

(l) Tetraethyl Dithiosuccinate

Diethyl 2-mercaptosuccinate was treated with 30% (v/v) hydrogen peroxide at ambient temperature for 16 hours in the presence of catalytic amount of HCl (32%). The reaction mixture was extracted with ethyl acetate and the organic layer washed with 2% sodium hydroxide solution in water to get rid of any un-reacted starting material. Removal of the solvent yielded a colorless product with purity of 95% (GC).

(m) Tetraethyl Thiosuccinate

The sodium salt of diethyl 2-mercaptosuccinate was reacted in two layer system (toluene/water) at ambient temperature with diethyl malaeate to yield the desired product.

Numerous references, including patents and various publications, are cited and discussed in the description of this invention. The citation and discussion of such references is provided merely to clarify the description of the present invention and is not an admission that any reference is prior art to the invention described herein. All references cited and discussed in this specification are incorporated herein by reference in their entirety. The embodiments illustrated and discussed in this specification are intended only to teach those skilled in the art the best way known to the inventors to make and use the invention. Nothing in this specification should be considered as limiting the scope of the present invention. Modifications and variation of the above-described embodiments of the invention are possible without departing from the invention, as appreciated by those skilled in the art in light of the above teachings. It is therefore understood that, within the scope of the claims and their equivalents, the invention may be practiced otherwise than as specifically described.

What is claimed is:

1. A pharmaceutical formulation comprising pharmaceutical grade malathion, said pharmaceutical grade malathion containing 0.1% or less (w/w) MeOOSPO, 0.1% or less (w/w) MeOSSPO, 0.2% or less (w/w) MeOOSPS, less than 0.1% (w/w) methyl malathion, 0.1% or less (w/w) malaoxon and 0.1% or less (w/w) isomalathion.

2. The pharmaceutical formulation of claim 1, comprising pharmaceutical grade malathion having a purity of greater than 99% (w/w).

3. The pharmaceutical formulation of claim 1 wherein the malathion in the formulation contains 0.05% or less (w/w) MeOOSPO.

4. The pharmaceutical formulation of claim 1 wherein the malathion in the formulation contains 0.04% or less (w/w) MeOOSPO.

5. The pharmaceutical formulation of claim 1 wherein the malathion in the formulation contains 0.02% or less (w/w) MeOSSPO.

6. The pharmaceutical formulation of claim 1, comprising pharmaceutical grade malathion containing not more than about 0.1% (w/w) of any other detectable impurity.

7. The pharmaceutical formulation of claim 1, wherein the malathion in the formulation contains 0.08% or less (w/w) methyl malathion.

8. The pharmaceutical formulation of claim 1, wherein the malathion in the formulation contains 0.06% or less (w/w) methyl malathion.

9. The pharmaceutical formulation of claim 1, wherein the malathion in the formulation contains 0.05% or less (w/w) isomalathion.

10. The pharmaceutical formulation of claim 1, wherein the malathion in the formulation contains 0.02% or less (w/w) isomalathion.

11. The pharmaceutical formulation of claim 1, wherein the malathion in the formulation contains 0.2% or less (w/w) diethyl fumarate and 0.2% or less (w/w) dimethylmalathion.

12. The formulation of claim 1, wherein the malathion in the formulation contains less than 0.05% (w/w) malaoxon.

13. The pharmaceutical formulation of claim 1 wherein the malathion in the formulation contains 0.1% or less (w/w) MeOOSPS.

14. The pharmaceutical formulation of claim 1, wherein the amount of isomalathion is not more than 0.1% (w/w), after storage for 3 months at 25° C. and 60% relative humidity.

15. The pharmaceutical formulation of claim 1, wherein the amount of isomalathion is not more than 0.1% (w/w), after storage for 3 months at 30° C. and 60% relative humidity.

16. The pharmaceutical formulation of claim 1, wherein the amount of isomalathion is not more than 0.1% (w/w), after storage for 3 months at 40° C. and 75% relative humidity.

17. A pharmaceutical formulation comprising at least 0.5% (w/w) malathion wherein the malathion contains less than 0.1% (w/w) isomalathion, less than 0.2% (w/w) MeOOSPS, less than 0.1% (w/w) malaoxon, and less than 0.07% methyl malathion.

18. The pharmaceutical formulation of claim 17, wherein the malathion has a purity greater than 98.5% (w/w).

19. The pharmaceutical formulation of claim 18, wherein the malathion has a purity greater than 99.0% (w/w).

20. The pharmaceutical formulation of claim 17, wherein the malathion contains less than 0.1% (w/w) MeOOSPO, less than 0.1% (w/w) MeOSSPO, and less than 0.1% malathion carboxylic acids.

21. The pharmaceutical formulation of claim 17, comprising 0.65% (w/w) of the pharmaceutical grade malathion.

22. The pharmaceutical formulation of claim 17, further comprising terpineol, dipentene, pine needle oil, and isopropyl alcohol.

23. The pharmaceutical formulation of claim 22, wherein the pharmaceutical formulation comprises at least 70% (w/w) isopropyl alcohol.

24. The pharmaceutical formulation of claim 22, comprising at least 12% (w/w) terpineol, at least 10% (w/w) dipentene, and at least 0.28% (w/w) pine needle oil.

25. The pharmaceutical formulation of claim 17 wherein the formulation is a lotion, gel, cream or solution.

26. The pharmaceutical formulation of claim 17, wherein the amount of isomalathion is less than 0.05% (w/w), after storage for 3 months at 5° C.

27. The pharmaceutical formulation of claim 17, wherein the amount of isomalathion is not more than 0.05% (w/w), after storage for 3 months at 25° C. and 60% relative humidity.

28. The pharmaceutical formulation of claim 17, wherein the amount of isomalathion is not more than 0.05% (w/w), after storage for 3 months at 30° C. and 60% relative humidity.

29. The pharmaceutical formulation of claim 17, wherein the amount of isomalathion is not more than 0.07% (w/w), after storage for 3 months at 40° C. and 75% relative humidity.

30. A pharmaceutical formulation comprising pharmaceutical grade malathion, said pharmaceutical grade malathion having a purity greater than 98.5 and containing 0.1% or less (w/w) MeOOSPO, 0.1% or less (w/w) MeOSSPO, 0.2% or less (w/w) MeOOSPS, less than 0.1% (w/w) methyl malathion, 0.1% or less (w/w) malaoxon and 0.1% or less (w/w) isomalathion.

31. The pharmaceutical formulation of claim 30, wherein the malathion further contains less than 0.1% (w/w) malathion carboxylic acids.

32. The pharmaceutical formulation of claim 30, containing not more than about 0.1% (w/w) of any other detectable impurity.

33. The pharmaceutical formulation of claim 1, wherein the pharmaceutical formulation is a lotion.

34. The pharmaceutical formulation of claim 33, comprising pharmaceutical grade malathion having a purity of greater than 99% (w/w).

35. The pharmaceutical formulation of claim 33 wherein the malathion in the formulation contains 0.05% or less (w/w) MeOOSPO.

36. The pharmaceutical formulation of claim 33, comprising pharmaceutical grade malathion containing 0.1% or less (w/w) of any detectable impurity other than MeOOSPO, MeOSSPO, MeOOSPS, methyl malathion, malaoxon or isomalathion.

37. The pharmaceutical formulation of claim 33, wherein the malathion in the formulation contains 0.08% or less (w/w) methyl malathion.

38. The pharmaceutical formulation of claim 33, wherein the malathion in the formulation contains 0.05% or less (w/w) isomalathion.

39. The pharmaceutical formulation of claim 33, wherein the malathion in the formulation contains 0.2% or less (w/w) diethyl fumarate and 0.2% or less (w/w) dimethylmalathion.

40. The formulation of claim 33, wherein the malathion in the formulation contains less than 0.05% (w/w) malaoxon.

41. The pharmaceutical formulation of claim 33 wherein the malathion in the formulation contains 0.1% or less (w/w) MeOOSPS.

42. The pharmaceutical formulation of claim 33, wherein the amount of isomalathion is not more than 0.1% (w/w), after storage for 3 months at 25° C. and 60% relative humidity.

43. The pharmaceutical formulation of claim 33, comprising 0.65% (w/w) of the pharmaceutical grade malathion.

44. The pharmaceutical formulation of claim 33, further comprising terpineol, dipentene, pine needle oil, and isopropyl alcohol.

45. The pharmaceutical formulation of claim 33, wherein the pharmaceutical formulation comprises at least 70% (w/w) isopropyl alcohol.

46. The pharmaceutical formulation of claim 33, comprising at least 12% (w/w) terpineol, at least 10% (w/w) dipentene, and at least 0.28% (w/w) pine needle oil.

47. The pharmaceutical formulation of claim 17, wherein the pharmaceutical formulation is a gel.

48. The pharmaceutical formulation of claim 47, wherein the malathion has a purity greater than 99.0% (w/w).

49. The pharmaceutical formulation of claim 47, wherein the malathion contains less than 0.1% (w/w) MeOOSPO, less than 0.1% (w/w) MeOSSPO, and less than 0.1% malathion carboxylic acids.

50. The pharmaceutical formulation of claim 47, comprising 0.65% (w/w) of the pharmaceutical grade malathion.

51. The pharmaceutical formulation of claim 47, further comprising terpineol, dipentene, pine needle oil, and isopropyl alcohol.

52. The pharmaceutical formulation of claim 47, wherein the pharmaceutical formulation comprises at least 70% (w/w) isopropyl alcohol.

53. The pharmaceutical formulation of claim 47, wherein the amount of isomalathion is not more than 0.05% (w/w), after storage for 3 months at 25° C. and 60% relative humidity.

54. The pharmaceutical formulation of claim 30, wherein the pharmaceutical formulation is a lotion.

55. The pharmaceutical formulation of claim 30, wherein the pharmaceutical formulation is a gel.

* * * * *

UNITED STATES PATENT AND TRADEMARK OFFICE
CERTIFICATE OF CORRECTION

| | | |
|---|---|---|
| PATENT NO. | : 7,977,324 B2 | |
| APPLICATION NO. | : 12/353691 | |
| DATED | : July 12, 2011 | |
| INVENTOR(S) | : Gutman et al. | |

It is certified that error appears in the above-identified patent and that said Letters Patent is hereby corrected as shown below:

Delete Patent number 7,977,324 in its entirety and insert Patent number 7,977,324 in its entirety as attached.

Signed and Sealed this
Twenty-first Day of August, 2012

David J. Kappos
*Director of the United States Patent and Trademark Office*

(12) United States Patent
Gutman et al.

(10) Patent No.: US 7,977,324 B2
(45) Date of Patent: *Jul. 12, 2011

(54) PROCESS FOR PREPARING MALATHION FOR PHARMACEUTICAL USE

(75) Inventors: Daniella Gutman, Rishon Lezion (IL); Wael Baidussi, Hamisholash (IL)

(73) Assignee: Taro Pharmaceuticals North America, Inc., Cayman (KY)

( * ) Notice: Subject to any disclaimer, the term of this patent is extended or adjusted under 35 U.S.C. 154(b) by 45 days.

This patent is subject to a terminal disclaimer.

(21) Appl. No.: 12/353,691

(22) Filed: Jan. 14, 2009

(65) Prior Publication Data
US 2009/0124823 A1 May 14, 2009

Related U.S. Application Data

(63) Continuation of application No. 11/427,863, filed on Jun. 30, 2006, now Pat. No. 7,560,445.

(60) Provisional application No. 60/697,010, filed on Jul. 6, 2005, provisional application No. 60/741,360, filed on Dec. 1, 2005, provisional application No. 60/743,741, filed on Mar. 24, 2006.

(51) Int. Cl.
*A61K 31/66* (2006.01)
(52) U.S. Cl. ............................................. 514/127
(58) Field of Classification Search .............. 514/127
See application file for complete search history.

(56) References Cited

U.S. PATENT DOCUMENTS

| | | |
|---|---|---|
| 2,578,652 A | 12/1951 | Cassaday |
| 2,863,902 A | 12/1958 | Santay |
| 2,879,284 A | 3/1959 | Divine et al. |
| 2,931,825 A | 4/1960 | Lutz |
| 2,962,521 A | 11/1960 | Usui |
| 2,980,723 A | 4/1961 | Frank et al. |
| 3,309,432 A | 3/1967 | English |
| 3,352,664 A | 11/1967 | Nolan et al. |
| 3,396,223 A | 8/1968 | Stark, Jr. |
| 3,403,201 A | 9/1968 | Adrian et al. |
| 3,440,305 A | 4/1969 | Divine |
| 3,463,841 A | 8/1969 | Backlund et al. |
| 3,470,272 A | 9/1969 | Melton |
| 3,515,782 A | 6/1970 | Nolan |
| 3,714,301 A | 1/1973 | Thomsen |
| 4,049,755 A | 9/1977 | Bianchi et al. |
| 4,367,180 A | 1/1983 | Rouy et al. |
| 4,520,013 A | 5/1985 | Nezat |
| 4,681,964 A | 7/1987 | Annarelli et al. |
| 5,783,202 A | 7/1998 | Tomlinson et al. |
| 6,103,248 A | 8/2000 | Burkhart et al. |
| 6,121,478 A | 9/2000 | Pedersen |
| 6,280,729 B1 | 8/2001 | Huang et al. |
| 6,500,994 B1 | 12/2002 | Brosch et al. |
| 6,521,762 B2 | 2/2003 | Keri et al. |
| 6,524,602 B1 | 2/2003 | Burkhart et al. |
| 6,562,363 B1 | 5/2003 | Mantelle et al. |
| 6,596,291 B2 | 7/2003 | Bell |
| 6,607,716 B1 | 8/2003 | Smith et al. |
| 6,689,394 B2 | 2/2004 | Van Scoik et al. |
| 6,806,292 B2 | 10/2004 | Riebel et al. |
| 6,939,715 B2 | 9/2005 | Beck et al. |
| 2002/0009486 A1 | 1/2002 | Godbey |
| 2002/0048558 A1 | 4/2002 | Niemiec et al. |
| 2003/0036530 A1 | 2/2003 | Bessette |
| 2004/0024052 A1 | 2/2004 | Gyuricza et al. |
| 2005/0031547 A1 | 2/2005 | Tamarkin et al. |
| 2006/0121073 A1 | 6/2006 | Goyal et al. |

FOREIGN PATENT DOCUMENTS

| | | |
|---|---|---|
| FR | 1541883 | 10/1968 |
| GB | 834814 | 5/1960 |
| GB | 2204243 | 11/1988 |
| GB | 2222949 | 3/1990 |
| RO | 86214 | 2/1985 |
| RO | 87602 | 12/1985 |
| WO | WO-03/066009 A1 | 8/2003 |
| WO | WO/2006/017232 | 2/2006 |
| WO | WO/2006/017263 | 2/2006 |

OTHER PUBLICATIONS

Meinking et al., Pediatric Dermatology, vol. 21, No. 6, pp. 670-674, 2004.
Nature's Mist, Skin Functioning and Dehydration, www.naturesmist.com, p. 1-4, 2003.
"A modern scourge parent scratch their heads over lice," Consumer Reports, Feb. 1998.
Office Action issued by the USPTO on Feb. 18, 2009 for U.S. Appl. No. 11/179,719.
Office Action issued by the USPTO on Sep. 16, 2009 for U.S. Appl. No. 11/179,719.
Office Action issued by the USPTO on May 27, 2010 for U.S. Appl. No. 11/179,719.
Office Action issued by the USPTO on Feb. 19, 2009 for U.S. Appl. No. 11/351,188.
Office Action issued by the USPTO on Sep. 21, 2009 for U.S. Appl. No. 11/351,188.
Office Action issued by the USPTO on May 27, 2010 for U.S. Appl. No. 11/351,188.
Al-Wakil et al., "Separation and Preconcentration of Malathion and Azamethiphos by Unloaded Polyurethane Foams," Qatar University Science Journal, vol. 14(spec. issue), 1994. (Abstract Only).

(Continued)

*Primary Examiner* — Rei-tsang Shiao
(74) *Attorney, Agent, or Firm* — Venable LLP; Michael A. Gollin; Zayd Alathari

(57) ABSTRACT

The present invention provides a process for preparing a highly pure form of malathion having a reduced level of toxic impurities. In addition, the malathion prepared by the process of this invention is storage stable. The level of toxic impurities in the malathion, e.g., isomalathion, O,O,S-trimethyl phosphorodithioate (MeOOSPS), O,O,S-trimethyl phosphorothioate (MeOOSPO), O,S,S-trimethyl phosphorodithioate (MeOSSPO), malaoxon, isomalathion, diethyl fumarate, methyl malathion, dimethyl malathion, O,O-methyl,ethyl-S-(1,2-dicarboethoxy)ethyl-phosphorodithioate are lower than that of any other commercial preparation of malathion that may be used for pharmaceutical purposes.

55 Claims, No Drawings

CERTIFICATE OF CORRECTION (continued)

OTHER PUBLICATIONS

Baker, Jr. et al., Epidemic Malathion Poisoning in Pakistan Malaria Workers, The Lancet, vol. 1, No. 8054, 1978.
Blasiak et al., "In Vitro Studies on the Genotoxicity of the Organophosphorus Insecticide Malathion and Its Two Analogues," Mutat. Res., vol. 445, No. 2, pp. 275-283, 2003. (Abstract Only).
Imamura et al., "Pulmonary Toxicity of Phosphorothioate Impurities Found in Organophosphate Insecticides," Pharmacology and Therapeutics, vol. 38, No. 3, pp. 419-427, 1988. (Abstract Only).
Liu et al., "Rapid Isolation with Sep-Pak C18 Cartridges and Wide Bore Capillary Gas Chromatography of Organophosphate Pesticides," Forensic Science International, vol. 41, No. 1-2, pp. 67-72, 1989. (Abstract Only).
Lupea et al., "Addition of Dimethyl Dithiophosphate to Ethyl Maleate and Ethyl Fumarate," Buletinul Stiintific si Tehnic al Institutului Politechnic Traian Vuia Timisoara, Seria Chimie, vol. 26, No. 1, pp. 51-60, 1981. (English Abstract Only).
Makarova et al., "Photometric Determination of Organophosphorus Pesticides After Separation By Thin Layer Chromatography," Industr. Lab., vol. 40, No. 7, pp. 961-964, 1974. (Abstract Only).
Malathion, 1GM, Neat—Product No. PS86; Sigma-Aldrich Catalog, 2003; with Certificate of Analysis.
Malathion, Pestanal®, analytical standard, Sigma-Aldrich Catalog, 2006, with Certificate of Analysis.
Ovide (Malathion) Lotion, 0.5%, NDC 51672-5276-4, Jul. 2005.
Patel et al., "Manufacture of Malathion," Pestic., Symp. (1968), Meeting Date 1964, pp. 69-72. (Abstract Only).
Polec et al., "Simple Syntheses of Malathion and Malaoxon Enantiomers, and Isomalathion Diastereoisomers: Toxicity-Configuration Relationship," Pesticide Science, vol. 53, No. 2, pp. 165-171, 1998. (Abstract Only).
Polec et al., "Synthesis of Malathion Enantiomers," Organika, vol. date 1995, pp. 7-15, 1996. (English Abstract Only).
Reimschussel et al., "Radioisotopic Studies On the Content and Conversion Rates of Toxic Impurities in Malathion," Pesticides: food and environmental implications, Proceedings of a symposium held in Neuherberg, Nov. 24-27, 1987, pp. 301-303, Published 1988. (Abstract Only).
Shvetsova-Shilovskaya et al., "Purification of Technical Carbophos," Khimicheskaya Promyshlennost, vol. 47, No. 11, p. 869, 1971. (English Abstract Only).
Supplementary European Search Report issued in EP Application No. 06774561 on Jun. 4, 2010.
Talcott et al., "Inactivation of Esterases by Impurities Isolated from Technical Malathion," Toxicology and Applied Pharmacology, vol. 49, No. 1, pp. 107-112, 1979. (Abstract Only).
Toia et al., "Identification and Toxicological Evaluation of Impurities in Technical Malathion and Fenthion," J. Agric. Food Chem., vol. 28, No. 3, pp. 599-604, 1980. (Abstract A Only).
Toia et al., "Identification and Toxicological Evaluation of Impurities in Technical Malathion and Fenthion," J. Agric. Food Chem., vol. 28, No. 3, pp. 599-604, 1980. (Abstract B Only).
Umezu, "Toxicity of Malathion to Mammals Potentiation of Toxicity by Impurities," Kagaku To Seibutsu (Chem. Biol.) vol. 16, No. 5, pp. 302-304, 1978. (English Abstract Only).
USP Monographs: Malathion Lotion, 2008.
USP Monographs: Malathion, 2008.
Wilkins et al., "A Study of the Trans-Esterification Products of Malathion by Capillary Gas Chromatography-Mass Spectrometry," Pesticide Science, vol. 20, No. 4, pp. 259-270, 1987. (Abstract Only).
Retro Search, Malathion Impurities, Sep. 13, 2005. (Collection of Abstracts).
Retro Search, Malathion Impurity, Sep. 13, 2005. (Collection of Abstracts).
Stability Results for Malathion Lotion, Aug.-Nov. 2004.
Certificates of Analysis, malathion USP, Cheminova, Jun. 1999-Oct. 2002.
"Impurities of maldison," Review Scope Document Maldison, p. 6-11, Feb. 2003.
EPA 1600 Methods, p. 213, 2003.
EPA 8000 Methods, pp. 238-239, 2003.
"Occupational Exposure to Organophosphate and Carbamate Insecticides," Department of Health and Human Services, p. 1-5, 2003.
Subpart II. B. Pharmacology and Toxicology, p. 62-123, 2003.
"Malathion Reregistration Eligibility Document: Environmental Fate and Effects Chapter," United States Environmental Protection Agency, p. 1-52, 2004.
Ovide (Malathion) Lotion, 0.5%, NDA 18-613, vol. 1 of 21, 1980.
Prioderm Lotion NDA 18-613, Replacement Pages, Book 1 of 3, 1980.
Ovide (Malathion) Lotion, 0.5%, NDC 99207-650-2, p. 3-8, 2004.
Memorandum: EFED's Response to Docket Comment, United States Environmental Protection Agency, p. 1-26, 2000.
Picchioni et al., "Activated Charcoal vs. "Universal Antidote" as an Antidote for Poisons," Toxicology and Applied Pharmacology, vol. 8, pp. 447-454, 1966.
Imamura et al., "Malathion and Phenthoate Carboxylesterase Activities in Pulmonary Alveolar Macrophages as Indicators of Lung Injury," Toxicology and Applied Pharmacology, vol. 70, pp. 140-147, 1983.
Rodgers et al., "Effect of administration of malathion for 90 days on macrophage function and mast cell degranulation," Toxicology Letters, vol. 93, pp. 73-82, 1997.
R. Baselt et al.,"Malathion", Disposition of Toxic Drugs and Chemicals in Man, p. 475-478, 1989.
Office Action issued by the USPTO on Oct. 21, 2008 for U.S. Appl. No. 11/427,863.
Certificate of Analysis for Batch No. S040110, dated Jan. 24, 2005 (redacted).
Certificate of Analysis for Batch No. S050133, dated Jan. 26, 2005 (redacted).
Certificate of Analysis for Batch No. S050151, dated Jan. 26, 2005 (redacted).
Certificate of Analysis for Batch No. S040109, dated Jan. 24, 2005 (redacted).
Certificate of Analysis for Batch No. S050134, dated Feb. 8, 2005 (redacted).
Certificate of Analysis for Batch No. S050135, dated Feb. 10, 2005 (redacted).
Certificate of Analysis for Batch No. S050136, dated Feb. 17, 2005 (redacted).
Certificate of Analysis for Batch No. S050137, dated Feb. 27, 2005 (redacted).
Certificate of Analysis for Batch No. S050155, dated Mar. 22, 2005 (redacted).
Certificate of Analysis for Batch No. S050169, dated Feb. 27, 2005 (redacted).
Certificate of Analysis for Batch No. S050170, dated Mar. 14, 2005 (redacted).
Certificate of Analysis for Batch No. S050171, dated Mar. 14, 2005 (redacted).
Certificate of Analysis for Batch No. S050172, dated Mar. 15, 2005 (redacted).
Certificate of Analysis for Batch No. S050173, dated Apr. 4, 2005 (redacted).
Certificate of Analysis for Batch No. S050174, dated Apr. 4, 2005 (redacted).
Certificate of Analysis for Batch No. S050190, dated Apr. 10, 2005 (redacted).
Certificate of Analysis for Batch No. S050200, dated Apr. 19, 2005 (redacted).
Certificate of Analysis for Batch No. S050201, dated Apr. 19, 2005 (redacted).
WHO Specifications and Evaluations for Public Health Pesticides: Malathion, World Health Organization, 2003.
Health Risk Assessment of Malathion Coproducts in Malathion-Bait Used for Agricultural Pest Eradication in Urban Areas, Report of the California Environmental Protection Agency, 1997.
Umetsu et al., *J. Agric. Food Chem.*, 25: 946-953 (1977).
Keadtisuke et al., *Toxicology Letters*, 52: 35-46 (1990).
Rodgers et al., *Immunopharmacology*, 17: 131-140 (1989).
Aldridge et al., *Archives Toxicology*, 42: 95-106 (1979).
Berkman et al., "Synthesis of Chiral Malathion and Isomalathion", *Terahedron Letters*, 33(11): 1415-1418 (1992).
Imamura et al., *Pharmacology and Therapeutics*, 38(3): 419-427 (1988).
Lahti et al., *Contact Dermatitis*, 12(3): 139-140 (1985).

Cotham WE Jr., et al., *Food Chem*, 37: 824-828 (1989).

N. Lee Wolfe et al., *J. Agric. Food Chem.*, 23(6): 1212-1215 (1976).

P. Boutsiouki et al., "Effects of local blood flow on the percutaneous absorption of the organophosphorus compound malathion: a microdialysis study in man.", *Arch. Toxicology*, 75(6): 321-8 (2001). PubMed Abstract, http://eresources.library.mssm.edu:2115/entrez/query.fcgi?CMD=Text&DM=pubmed, 1 page.

F. Musshoff et al., "Simple determination of 22 organophosphorous pesticides in human blood using headspace solid-phase microextraction and gas chromatorgrphy with mass spectrometric detection", *Chromatogr. Sci.*, 40(1): 29-34 (2002). PubMed Abstract, http://eresources.library.mssm.edu:2115/entrez/query.fcgi?CMD=Text&DB=pubmed, 1 page.

S. Bradu et al., "Flammability of Topical Agents to Common Environmental Fire Hazards", Ab#155-04, Mar. 2005.

M. Bouchard et al., *Toxicological Sciences*, 73: 182-194 (2003).

S. Padilla et al., *Journal of Toxicology and Environmental Health*, Part A, 67: 1477-1489 (2004).

P. Lee et al., *Intensive Care Med.*, 27: 694-699 (2001).

R. Zweiner et al., *Pediatrics*, 81(1): 121-126 (1988).

C. Vidair, Toxicology and Applied Pharmacology, 196: 287-302 (2004).

D. Hamilton, "JMPS Evaluation of Data Supporting Specification—the Practicalities", CIPAC Symposium, Utrecht, 8 pages (Jun. 6, 2005).

M. Fuller, "Jun. 28, 1998—Bradenton Mediterranean Fruit Fly Update DACS", http://pestalert.ifas.ufl.edu/Medfly/dacs06228.htm (accessed Nov. 13, 2005).

W. Boyes et al., *Journal of Applied Toxicology*, 19: 473-483 (1999).

J. Cocker et al., *Toxicology Letters*, 134: 97-103 (2002).

M. Maroni et al., *Toxicology*, 143: 5-37 (2000).

M. Brown et al., *Environ. Sci. Technol.*, 27(2): 388-397 (1993).

R. Krieger et al., *Arch. Environ. Contam. Toxicol.*, 38: 546-553 (2000).

J. Storm et al., *Toxicology*, 150: 1-29 (2000).

J. Cocker et al., *Toxicology*, 134: 97-103 (2002).

B. Nutley et al., *Pestic. Sci.*, 38: 315-322 (1993).

R. Fenske et al., *J. Agric. Food Chem.*, 37: 995-998 (1989).

K. Rodgers et al., *Pesticide Biochemistry and Physiology*, 25: 358-365 (1986).

J. Herath et al., *Cytologia*, 54: 191-195 (1989).

A. Nishio et al., *Journal of Toxicology and Environmental Health*, 8: 939-946 (1981).

Z. Walter et al., *Human Genetics*, 53: 375-381 (1980).

P. Flessel et al., *Environmental and Molecular Mutagenesis*, 22: 7-17 (1993).

S. Amer et al., *Journal of Applied Toxicology*, 16(1): 1-3 (1996).

V. Garry et al., *Teratogenesis, Carcinogenesis, and Mutagenesis*, 10: 21-29 (1990).

A. Nicholas et al., *Mutation Research*, 67: 167-172 (1979).

International Search Report issued for PCT Appleiation PCT/US06/26251, mailed on Nov. 21, 2007.

Written Opinion issued for PCT Application PCT/US06/26251, mailed on Nov. 21, 2007.

FAO Specifications and Evaluations for Agricultural Pesticides, Malathion, Food and Agricultural Organization of the United States, Dec. 2004.

Talley, Todd T. "My Research", http://www2.uml.edu/medchem/ttt/research%20page.html, printed on Nov. 13, 2005.

"Determination of minor components in technical Malathion", Cheminova Analyical Methods, edition 1, Jul. 1, 2003.

Malathion, monograph numbe 5470, copyright 1999 by Merck & Co., Inc., Whitehouse Stations, NJ, USA.

Cheminova, "Formulations and Brands", <http://www.cheminova.com/en/insectices/fyfanon/formulations and brands.htm>, 1 page, printed Aug. 26, 2005.

Cheminova, "Background—Fyfanon®", <http://www.cheminova.com/en/insectices/fyfanon/background.htm>, 1 page, printed Aug. 26, 2005.

Attorney for Medicis manufacturer, of Malathion based Ovide—who writes below that "USP grade Malathion is safe, effective and non-toxic", http://ww.safe2use.com/ca-ipm/00-11-28-ltr.htm, printed Oct. 6, 2005.

"Malathion vs. Mosquitoes", CBC Manitoba, http://winnipeg.cbc.ca/indepth/malathion/, 3 pages, Jul. 7, 2004, printed Dec. 14, 2004.

"Pesticides: Topical & Chemical Fact Sheet; Malathion for Mosquito Control", U.S. Environmental Protection Agency, http://www.epa.gov/pesticides/factsheets/malathion4mosquitos.htm, 5 pages, updated Apr. 17, 2002, printed Dec. 14, 2004.

"Malathion—toxicity, ecological toxicity and regulatory information", PAN Pesticides Database—Chemicals, http://www.pesticidenfo.org/Detail_Chemical.jsp?Rec_Id=PC32924, 9 pages, printed Aug. 31, 2005.

"4.20 Malathion (T)**", http://www.fao.org/docrep/W8141E/w8141e0x.htm, 4 pages, printed May 7, 2004.

"Insecticides Used as Ectoparasiticides", Goodman & Gilman's "The Pharmacological Bases of Therapeutics", 9_th Ed., Copyright 1996 McGraw-Hill Companies, Inc., printed May 2, 2003.

"I.A. Reference Dose for Chronic Oral Exposure (RfD): Substance Name—Malathion", 1 page, Last Revised Jan. 1, 1992.

Sigma-Aldrich, "Product Name: Malathion", http://www.sigmaaldrich.com/cgi-bin/hsrun/Distributed/HahtShop/HahtShop.htx;start=frmCa...., 1 page, printed Oct. 9, 2003.

Chemservice, "Detailed Database Results, Description: Malathion", http://www.chemservice.com/result_detail.asp?CATNUM=F2118, 2 pages, printed Oct. 7, 2003.

"Malathion", IARC Summaries & Evaluations, vol. 30, 1983, http://www.inchem.org/documents/iarc/vol30/malathion.html, 4 pages, printed Jul. 11, 2005.

"Maldison (Malathion) Review Scope Document", National Registration Authority For Agricultural and Veterinary Chemicals, Feb. 2003.

"Joint Statement on Review of Malathion", Department of Health, http://www.doh.gov.uk/com/malathion.htm, p. 1-16, Mar. 2003, printed on Oct. 7, 2003.

"COM meeting Apr. 25, 2002", Department of Health, http://www.doh.gov.uk/com/mut023.htm, p. 1-8, printed on Oct. 6, 2003.

"Guidelines for Physicians who supervise workers exposed to cholinesterase-inhibiting pesticides", 4th Ed., Office of Environmental Hazard Assessment California Environmental Protection Agency, 2002.

Ovide (Malathion) Lotion, 0.5%, NDA 18-613, vol. 2, Dec. 31, 1998.

PROCESS FOR PREPARING MALATHION FOR PHARMACEUTICAL USE

This application is a continuation of application Ser. No. 11/427,863, filed on Jun. 30, 2006 now U.S. Pat. No. 7,560,445 which claims the priority under 35 U.S.C. §1.119(e) of Provisional Application Ser. Nos. 60/697,010 filed Jul. 6, 2005, 60/741,360 filed Dec. 1, 2005 and 60/743,741 filed Mar. 24, 2006, all of which are incorporated by reference in their entireties herein.

FIELD OF THE INVENTION

The present invention relates to a process of preparing malathion for pharmaceutical use and compositions comprising a highly purified form of malathion that is stable during storage.

BACKGROUND OF THE INVENTION

Malathion ([(dimethoxyphosphinothioyl)thio]butanedioic acid diethyl ester; CAS # 121-75-5) is an organophosphate insecticide that inhibits cholinesterase activity in vivo. Malathion has the following chemical structure:

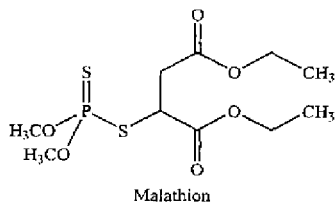

Malathion

Malathion may be prepared by reacting O,O-dimethyldithiophosphoric acid (DMDP) with diethyl maleate (U.S. Pat. Nos. 2,578,652, 2,879,284, 3,403,201, 3,463,841, 3,470,272, 4,367,180 and 4,681,964).

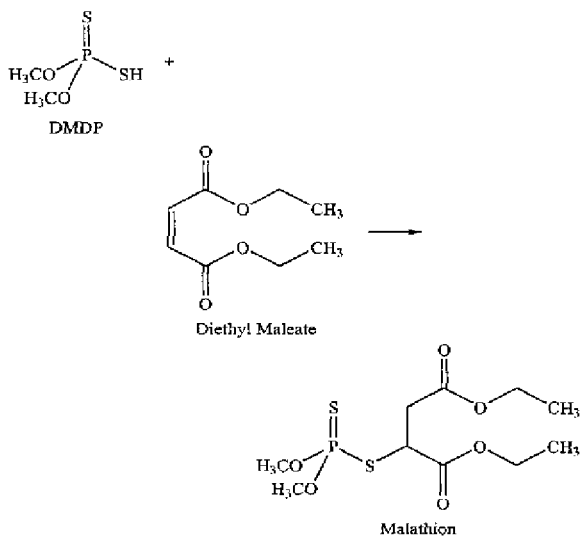

DMDP

Diethyl Maleate

Malathion

Numerous impurities are found in malathion preparations; these impurities include, O,O,S-trimethyl phosphorodithioate (MeOOSPS), O,O,S-trimethyl phosphorothioate (MeOOSPO), O,S,S-trimethyl phosphorodithioate (MeOSSPO), malaoxon, isomalathion, diethyl fumarate, methyl malathion, dimethyl malathion, O,O-methyl,ethyl-S-(1,2-dicarboethoxy)ethyl-phosphorodithioate, and tetraethyl dithiodisuccinate (See, WHO Specifications and Evaluations for Public Health Pesticides: Malathion, World Health Organization, 2003). Some of these impurities are formed as breakdown products during storage, but, the majority of these impurities are generated as unintentional byproducts during synthesis. (Health Risk Assessment of Malathion Coproducts in Malthion-Bait Used for Agricultural Pest Eradication in Urban Areas, Report of the California Environmental Protection Agency, 1997). For example, during storage, malathion can convert to isomalathion by dimerization, and the extent of isomerization is dependent on particular storage conditions. (Health Risk Assessment of Malathion Coproducts in Malthion-Bait Used for Agricultural Pest Eradication in Urban Areas, Report of the California Environmental Protection Agency, 1997).

Storage of malathion at elevated temperatures, e.g., 40° C., significantly enhances toxicity of the malathion preparation (Umetsu et al., *J. Agric. Food Chem.*, 25:946-953 (1977)). In part, this enhancement is due to an increase in isomalathion after storage. For example, after storage for 6 months at 40° C., there was an increase in isomalathion content from 0.2% to 0.45%, with an accompanying 35% increase in toxicity as measured by $LD_{50}$ in mice (Umetsu et al., *J. Agric. Food Chem.*, 25:946-953 (1977)). Because even small or trace quantities of malathion impurities such as isomalathion have been shown to be highly toxic, the presence of these impurities in any malathion preparation, but especially one developed for pharmaceutical use, should be reduced as much as possible. Moreover, given that malathion breaks down into toxic by-products during storage, it is also desirable to prepare malathion which is storage stable.

Many of these malathion impurities have been found to be toxic. MeOOSPO and MeOSSPO can cause liver damage (Keadtisuke et al., *Toxicology Letters* 52:35-46 (1990)), or immune suppression (Rodgers et al., *Immunopharmacology* 17:131-140 (1989)). Isomalathion has been shown to cause death in people after spraying during insect eradication programs. (Aldridge et al., *Archives Toxicology* 42:95-106 (1979)). The toxicity of isomalathion is due to its ability to inhibit acetylcholinesterase; in fact, isomalathion is approximately 1,000 times as active against acetylcholinesterase as compared with malathion. (Berkman et al. Synthesis of Chiral Malathion and Malathion, *Terahedron Letters* 33(11): 1415-1418 (1992)). O,O-methyl,ethyl-S-(1,2-dicarboethoxy)ethyl-phosphorodithioate, isomalathion and MeOOSPO all exhibit pulmonary toxicity and can cause death from hypoxia. (Imamura et al., *Pharmacology and Therapeutics* 38(3):419-427 (1988)). Malaoxon inhibits cholinesterase enzymes. (Umetsu et al., *J. Agric. Food Chem.*, 25:946-953 (1977)). Diethyl fumarate can cause contact urticaria. (Maibach, *Contact Dermatitis* 12(3):139-140 (1985)). Malathion's physical properties make it difficult to remove impurities by conventional means. For example, because malathion is a liquid at ambient temperature (melting point=2.9° C.), crystallization is difficult. Malathion also has a high boiling point (156-157° C.), consequently, distillation also has its problems, especially as malathion is unstable at elevated temperatures.

We have now developed a novel method for synthesizing and purifying malathion for pharmaceutical use. The malathion prepared by the methods of this invention has significantly lower levels of toxic impurities such as isomalathion when compared with other, commercially available malathion preparations that are currently used for pharmaceutical purposes. Moreover, because malathion is known to be unstable, the levels of toxic impurities, e.g., isomalathion, are known to increase over time, there is a need to develop a stable form of malathion. The malathion of the present invention is storage stable, i.e., even after storage at elevated temperature and humidity, the levels of toxic impurities do not increase significantly.

SUMMARY OF THE INVENTION

The methods of the invention provide for a process for preparing malathion, comprising, the steps of (a) preparing a solution of O,O-dimethyldithiophosphoric acid in an organic solvent, selected from the group consisting of toluene, xylene and benzene; (b) extracting the O,O-dimethyldithiophosphoric acid into water to generate an aqueous solution of O,O-dimethyldithiophosphoric acid; (c) reacting the aqueous solution of O,O-dimethyldithiophosphoric acid with diethyl maleate to form malathion; and, (d) treating the malathion from step (c) with a sulfur reagent, wherein the sulfur reagent has a pH less than about 7.0. 2. In one embodiment, the organic solvent is toluene.

The O,O-dimethyldithiophosphoric acid in step (a) may be prepared by the steps comprising, the steps of: (i) adding phosphorous pentasulfide ($P_2S_5$) to toluene to form a suspension; (ii) heating the suspension to about 60° C.; (iii) adding methanol to the suspension; (iv) stirring the suspension after addition of the methanol for at least about 1 hour, while maintaining the temperature of the suspension from about 55° C. to about 60° C.; (v) filtering the suspension from step (iv) after cooling to about 18° C. to about 25° C.; and, (vi) subjecting the suspension from step (v) to vacuum distillation.

The malathion from step (d) may be isolated after treatment with the sulfur reagent. The ratio of water to O,O-dimethyldithiophosphoric acid in step (b) may be about 1:1 to about 10:1 (w/w). In one embodiment, the ratio of water to O,O-dimethyldithiophosphoric acid is about 3:1 (w/w).

The solution of O,O-dimethyldithiophosphoric acid in step (a) may be filtered before extraction into water in step (b). Alternatively, the solution of O,O-dimethyldithiophosphoric acid in step (a) is distilled before extraction into water in step (b).

In one embodiment, the molar ratio of diethyl maleate to O,O-dimethyldithiophosphoric acid in step (c) is about 1:1 to about 2:1. In another embodiment, the molar ratio of diethyl maleate to O,O-dimethyldithiophosphoric acid in step (c) is about 1:1.

A polymerization inhibitor may be added to step (c) during the reaction of the aqueous solution of O,O-dimethyldithiophosphoric acid with the solution of diethyl maleate. The molar ratio of diethyl maleate to the polymerization inhibitor may be about 50:1 to about 500:1. In one embodiment, the molar ratio of diethyl maleate to polymerization inhibitor is about 300:1. The polymerization inhibitor may be hydroquinone.

The sulfur reagent is selected from the group consisting of alkali metal bisulfites and alkaline earth metal bisulfites. In one embodiment, the sulfur reagent is sodium bisulfite. In another embodiment, the sulfur reagent comprises a 20% sodium bisulfite solution having a pH from about 6.1 to about 6.3. The malathion in step (d) may be treated with the 20% sodium bisulfite solution for about 2 hours.

After treatment with the 20% sodium bisulfite solution, the malathion may be washed with water, a 5% NaOH solution and at least two more times with water. After washing with these solutions, the malathion may be assayed for the presence of at least one impurity selected from the group consisting of MeOOSPS, malaoxon, diethyl fumarate, dimethyl malathion, methyl malathion, isomalathion and O,O-methyl, ethyl S-(1,2-dicarboethoxy)ethyl phosphorodithioate, and combinations thereof. In addition, the malathion is assayed for purity. If the malathion at step contains greater than about 5.0% (w/w) diethyl fumarate, the washing steps with water, NaOH and again with water may be repeated as discussed above prior to isolating the malathion.

Preferably, the purified malathion contains 0.1% (w/w) or less of tetraethyl dithiodisuccinate.

Preferably, the purified malathion contains 0.1% (w/w) or less of diethyl fumarate. More preferably, the purified malathion contains 0.05% (w/w) or less of diethyl fumarate.

At this stage of the purification, the malathion may be greater than about 98.5% (w/w) malathion, less than about 5% (w/w) diethyl fumarate and less than about 0.1% (w/w) isomalathion. In another embodiment, the malathion may be greater than 98.5% (w/w) malathion, less than about 0.2% (w/w) MeOOSPS, less than about 0.1% (w/w) malaoxon, less than about 0.2% (w/w) diethyl fumarate, less than about 0.3% (w/w) methylmalathion, and less than about 0.3% (w/w) O,O-methyl, ethyl S-(1,2-dicarboethoxy)ethyl phosphorodithioate. In addition, there may be less than about 0.1% (w/w) of any other detectable impurity in the malathion at this stages of the purification.

The malathion prepared as above may be further purified by the steps of: (1) adding water to the malathion; (m) subjecting the malathion from step (k) to azeotropic distillation; (n) repeating steps (l) to (m) at least one (1) time; and, (o) isolating the malathion. The ratio of water to malathion in step (l) ranges from about 2:1 (w/w) to about 10:1 (w/w). In one embodiment, the ratio of water to malathion in step (l) is about 3:1 (w/w). After azeotropic distillation, the malathion is assayed for the presence of at least one impurity selected from the group consisting of MeOOSPO, MeOSSPO, malaxon, MeOOSPS, diethyl fumarate, dimethyl malathion, methyl malathion, O,O-methyl, ethyl S-(1,2-dicarboethoxy)ethyl phosphorodithioate, tetraethyl dithiosuccinate, isomalathion, malathion carboxylic acid, mercaptosuccinate, tetraethyl thiodisuccinate and combinations thereof. In addition, the malathion is assayed for purity. Steps (l) to (o) are repeated if the malathion has greater than about 0.2% (w/w) MeOOSPS, greater than about 0.1% (w/w) malaoxon, greater than about 0.2% (w/w) diethyl fumarate, greater than about 0.2% (w/w) dimethylmalathion, greater than about 0.3% (w/w) methylmalathion, greater than about 0.1% (w/w) isomalathion, or there is less than about 98.5% (w/w) malathion.

Preferably, the purified malathion contains 0.2% (w/w) or less of O,O,S-trimethyl phosphorodithioate. More preferably, the purified malathion contains 0.1% (w/w) or less of O,O,S-trimethyl phosphorodithioate.

At this stage of the purification, the malathion may have greater than about 98.0% (w/w) malathion, less than about 0.1% (w/w) isomalathion and less than about 0.1% (w/w) malathion monoacid. In one embodiment, the isomalathion in this malathion preparation may be less than about 0.02% (w/w). In a third embodiment, the malathion has greater than about 98.5% (w/w) malathion, less than about 0.2% (w/w) MeOOSPS, less than about 0.1% (w/w) malaoxon, less than about 0.2% (w/w) diethyl fumarate, less than abut 0.2% (w/w) dimethylmalathion, less than about 0.3% (w/w) methylmalathion and less than about 0.02% (w/w) isomalathion.

In another embodiment, the malathion has greater than about 99.5% (w/w) malathion, less than about 0.1% (w/w) MeOOSPS, less than about 0.05% (w/w) malaoxon, less than about 0.01% (w/w) diethyl fumarate, less than about 0.02% (w/w) dimethylmalathion, less than about 0.07% (w/w) methylmalathion, and less than about 0.02% (w/w) isomalathion. In any of the above embodiments, there may be less than about 0.1% (w/w) of any other detectable impurity.

The malathion may be stored under a variety of different conditions. After storage, the malathion is assayed for purity and for the presence of various impurities. For example, after storage for about 3 months at about 5° C., the malathion is greater than about 98.0% (w/w) malathion and less than about 0.03% (w/w) isomalathion. After storage for at least about 3 months at about 25° C. and about 60% relative humidity, the malathion may have greater than about 98.0% (w/w) malathion and less than about 0.04% (w/w) isomalathion. After storage for at least about 3 months at about 30° C. and about 60% relative humidity, the malathion may have greater than about 98.0% (w/w) malathion and less than about 0.06% (w/w) isomalathion. After storage for at least about 3 months at about 40° C. and about 75% relative humidity, the malathion may have greater than about 98.0% (w/w) malathion and less than about 0.1% (w/w) isomalathion.

Malathion containing greater than about 98.0% (w/w) malathion, less than about 0.1% (w/w) isomalathion and less than about 0.1% (w/w) malathion monoacid may be formulated into a pharmaceutical formulation comprising, at least about 0.5% (w/w) malathion and at least about 70% (w/w) isopropyl alcohol. After storage at about 40° C. and about 75% relative humidity for about 3 months, the isomalathion present in the formulation is less than about 0.07% (w/w). The pharmaceutical formulation may further comprise at least about 12% (w/w) terpineol, at least about about 10% (w/w) dipentene and at least about 0.28% pine needle alcohol.

The malathion prepared by the process of the invention comprises the following embodiments: (i) greater than about 98.5% (w/w) malathion, less than about 0.1% (w/w) MeOOSPO, less than about 0.1% (w/w) MeOSSPO, less than about 0.2% (w/w) MeOOSPS, less than about 0.3% (w/w) malathion carboxylic acid and less than about 0.1% (w/w) isomalathion; (ii) greater than about 98.5% (w/w) malathion, less than about 0.1% (w/w) MeOOSPO, less than about 0.1% (w/w) MeOSSPO, less than about 0.2% (w/w) MeOOSPS, less than about 0.3% (w/w) malathion carboxylic acid and less than about 0.02% (w/w) isomalathion; (iii) greater than about 99.0% (w/w) malathion, less than about 0.1% (w/w) MeOOSPO, less than about 0.1% (w/w) MeOSSPO and less than about 0.1% (w/w) MeOSSPS, 0.03% (w/w) malathion carboxylic acids and less than about 0.02% (w/w) isomalathion; and, (iv) greater than about 99.0% (w/w) malathion, less than about 0.04% (w/w) MeOOSPO, less than about 0.02% (w/w) MeOSSPO and less than about 0.1% (w/w) MeOSSPS, 0.03% (w/w) malathion carboxylic acids and less than about 0.02% (w/w) isomalathion.

The malathion prepared by the process of this invention is stable after storage. Specifically, after storage at 5° C. for 3 months the amount of isomalathion is not more than about 0.1% (w/w). After storage for 3 months at 25° C. and 60% relative humidity, the amount of isomalathion is not more than about 0.1% (w/w). After storage for 3 months at 30° C. and 60% relative humidity, the amount of isomalathion is not more than about 0.1% (w/w).

The present invention further provides a process for preparing pharmaceutical grade malathion, comprising the steps of:

(a) reacting a phosphorus sulfide with methanol in an organic solvent to form an organic solution of O,O-dimethyldithiophosphoric acid;
(b) extracting O,O-dimethyldithiophosphoric acid from the organic solution into water to form an aqueous solution of O,O-dimethyldithiophosphoric acid;
(c) reacting the aqueous solution of O,O-dimethyldithiophosphoric acid with diethyl maleate to form malathion;
(d) preparing an acidic aqueous solution containing at least one sulfur reagent selected from the group consisting of bisulfites, sulfites, and sulfides;
(e) contacting the malathion with the acidic aqueous solution at a pH below 7;
(f) mixing the malathion with water; and
(g) distilling water from the mixture at a temperature of about 60° C. or lower.

Preferably, the process further comprises after step (a) and before step (b) the steps of:
(i) filtering the organic solution of O,O-dimethyldithiophosphoric acid; and
(ii) concentrating the organic solution of O,O-dimethyldithiophosphoric acid.

The present invention further provides a composition of pharmaceutical grade malathion, which contains 0.1% (w/w) or less of isomalathion, and 0.1% (w/w) or less of each individual unknown impurity present in the composition.

Preferably, the composition contains 0.05% (w/w) or less of isomalathion. More preferably, the composition contains 0.02% (w/w) or less of isomalathion.

Preferably, the composition contains less than 0.05% (w/w) of O,O,S-trimethyl phosphorothioate (MeOOSPO). More preferably, the composition contains less than 0.04% (w/w) of O,O,S-trimethyl phosphorothioate (MeOOSPO).

Preferably, the composition contains less than 0.1% (w/w) of methyl malathion. More preferably, the composition contains 0.08% (w/w) or less of methyl malathion. More preferably, the composition contains 0.06% (w/w) or less of methyl malathion.

Preferably, the composition contains less than 0.05% (w/w) of O,O,S-trimethyl phosphorothioate (MeOOSPO) and less than 0.1% (w/w) of methyl malathion. Preferably, the composition contains 0.05% (w/w) or less of isomalathion, less than 0.04% (w/w) of O,O,S-trimethyl phosphorothioate (MeOOSPO), and 0.08% (w/w) or less of methyl malathion. Preferably, the composition contains 0.02% (w/w) or less of isomalathion, less than 0.04% (w/w) of O,O,S-trimethyl phosphorothioate (MeOOSPO), and 0.06% (w/w) or less of methyl malathion.

The present invention further provides a commercial scale composition of pharmaceutical grade malathion, which contains 0.1% (w/w) or less of isomalathion, and 0.1% (w/w) or less of each individual unknown impurity present in the composition.

Preferably, the commercial scale composition contains 0.05% (w/w) or less of isomalathion. More preferably, the commercial scale composition contains 0.02% (w/w) or less of isomalathion.

Preferably, the commercial scale composition contains less than 0.05% (w/w) of O,O,S-trimethyl phosphorothioate (MeOOSPO). More preferably, the commercial scale composition contains less than 0.04% (w/w) of O,O,S-trimethyl phosphorothioate (MeOOSPO).

Preferably, the commercial scale composition contains less than 0.1% (w/w) of methyl malathion. More preferably, the commercial scale composition contains 0.08% (w/w) or less of methyl malathion. More preferably, the commercial scale composition contains 0.06% (w/w) or less of methyl malathion.

Preferably, the commercial scale composition contains less than 0.05% (w/w) of O,O,S-trimethyl phosphorothioate (MeOOSPO) and less than 0.1% (w/w) of methyl malathion. Preferably, the commercial scale composition contains 0.05% (w/w) or less of isomalathion, less than 0.04% (w/w) of O,O,S-trimethyl phosphorothioate (MeOOSPO), and 0.08% (w/w) or less of methyl malathion. Preferably, the commercial scale composition contains 0.02% (w/w) or less of isomalathion, less than 0.04% (w/w) of O,O,S-trimethyl phosphorothioate (MeOOSPO), and 0.06% (w/w) or less of methyl malathion.

The present invention further provides a commercial scale composition of pharmaceutical grade malathion, which contains 0.1% (w/w) or less of isomalathion after storing the composition for three (3) months at 25° C.±2° C. and 60%±5% relative humidity.

DETAILED DESCRIPTION OF THE INVENTION

The present invention provides a process for preparing a highly purified form of malathion that may be used for pharmaceutical formulations. Malathion is synthesized by (a) preparing a solution of O,O-dimethyldithiophosphoric acid in an organic solvent; (b) extracting the O,O-dimethyldithiophosphoric acid into water to generate an aqueous solution of O,O-dimethyldithiophosphoric acid; (c) reacting the aqueous solution of O,O-dimethyldithiophosphoric acid with diethyl maleate to form malathion; and, (d) treating the malathion from step (c) with a sulfur reagent, wherein the sulfur reagent has a pH less than about 7.0.

The O,O-dimethyldithiophosphoric acid in step (a) may be produced by (i) suspending phosphorus sulfide in an organic solvent, (ii) adding methanol to the phosphorous sulfide suspension drop-wise and, (iii) mixing the phosphorous sulfide suspension. A phosphorus sulfide is a compound of formula $P_xS_y$, wherein x and y are integers. Examples of phosphorus sulfides include compounds such as phosphorus pentasulfide ($P_2S_5$), tetraphosphorus heptasulfide ($P_4S_7$) as well as mixtures of these compounds. Phosphorus pentasulfide is usually found as a dimer, tetraphosphorus decasulfide ($P_4S_{10}$) (the term phosphorus pentasulfide includes, the dimer, tetraphosphorus decasulfide). In one embodiment, the phosphorus sulfide is phosphorus pentasulfide. Any suitable organic solvent may be used to suspend the phosphorus sulfide. Suitable organic solvents such as toluene, xylene and benzene as well as mixtures may be used. In a preferred embodiment, toluene is used as the organic solvent for suspending the phosphorous sulfide.

Because higher temperatures cause decomposition of O,O-dimethyldithiophosphoric acid as well as formation of undesirable byproducts, the temperature of the step where the phosphorous sulfide suspension is mixed (step (iii), above) is controlled. Mixing may proceed for approximately 1 hour, while maintaining the temperature of the reaction vessel between about 55° C. to about 65° C. with nitrogen ($N_2$) bubbling. After mixing, the reaction mixture is cooled to a temperature of about 18° C. to about 25° C.

Prior to extraction into water, the solution of O,O-dimethyldithiophosphoric acid in an organic solvent may be further purified by filtration, distillation or evaporation. Filtration removes insoluble impurities such as any un-reacted solids, e.g., $P_2S_5$. Other suitable methods of removing insoluble impurities, include, decantation and centrifugation.

The solution of O,O-dimethyldithiophosphoric acid in the organic solvent may be concentrated or purified by distillation. Preferably, the solution of O,O-dimethyldithiophosphoric acid in the organic solvent is distilled by azeotropic distillation. An advantage of distillation (e.g., azeotropic distillation) is that it effectively removes MeOOSPS without generating the isomerization products of malathion and isomalathion. Distillation may be performed under vacuum. Distillation removes volatile impurities such as, hydrogen sulfide ($H_2S$) as well as any unreacted methanol or other organic solvents, e.g., toluene. If hydrogen sulfide is present in the O,O-dimethyldithiophosphoric acid, it can react with diethyl maleate or diethyl fumarate to form diethyl 2-mercaptosuccinate. Diethyl 2-mercaptosuccinate can be oxidized to form a dimeric impurity, tetraethyl dithiodisuccinate, which is very difficult to remove from any malathion preparation.

Another advantage of the distillation (e.g., azeotropic distillation) is to effectively remove unreacted methanol. If unreacted methanol is present as an impurity in the O,O-dimethyldithiophosphoric acid, it can react with malathion to form both methanolysis and transesterification impurities. Methanolysis impurities include, O,O,O,-trimethylthiophosphoric acid (MeOOOPS) and O,O,S-trimethylthiophosphoric acid (MeOOSPO). Transesterification impurities include, [(dimethoxyphosphinothioyl)thio]butanedioic acid dimethyl ester (dimethyl malathion), 1-carboethoxy-2-carbomethoxy-1-[(dimethoxyphosphinothioyl)thio]ethane, and 2-carboethoxy-1-carbomethoxy-1-[(dimethoxyphosphinothioyl)thio]ethane; 1-carboethoxy-2-carbomethoxy-1-[(dimethoxyphosphinothioyl)thio]ethane, and 2-carboethoxy-1-carbomethoxy-1-[(dimethoxyphosphinothioyl)thio]ethane are collectively referred to as methyl malathion. These impurities are difficult to remove from the malathion preparation.

Another advantage of the distillation process is to remove dissolved $H_2S$. If $H_2S$ is present, it will react with diethyl maleate to afford diethyl 2-mercaptosuccinate and dimerize to form tetraethyl dithiodisuccinate.

Typically, the distillation step removes a portion of the organic solvent, e.g., toluene xylene or benzene, together with other volatile impurities such as methanol. After distillation, the concentration of the O,O-dimethyldithiophosphoric acid in the solution is about 30% (w/w) to about 70% (w/w); more preferably, the concentration of the O,O-dimethyldithiophosphoric acid in solution may be about 50% (w/w). Preferably, the distillation may be performed at reduced pressure, e.g., less than about 1 atmosphere (1 atmosphere=760 mm Hg). In another embodiment, the distillation may be performed at a pressure of about 0.5 atmosphere, while in a third embodiment, the distillation may be performed at a pressure of about 0.2 atmosphere.

After the distillation, evaporation or filtration step, the O,O-dimethyldithiophosphoric acid in the organic solvent is extracted into water to yield an aqueous solution of O,O-dimethyldithiophosphoricacid. An advantage of the present invention is that extraction of the O,O-dimethyldithiophosphoric acid into water significantly removes MeOOSPS. Analysis by gas chromatography of the O,O-dimethyldithiophosphoric acid in the organic solvent before extraction with the water indicates that the O,O-dimethyldithiophosphoric acid is contaminated with up to about 25-30% (w/w) of O,O,S-trimethyl phosphorodithioate (MeOOSPS) as well as with other impurities, such as, O,O,S-trimethyl phosphorothioate (MeOOSPO). After extraction with water, gas chromatography analysis indicates that the quantity of O,O,S-trimethyl phosphorodithioate (MeOOSPS) in the aqueous solution of O,O-dimethyldithiophosphoric acid is reduced to about 5-6% (w/w) or less.

Any suitable quantity of water may be used for the extraction. The ratio of water to the organic solution of O,O-dimethyldithiophosphoric acid may be from about 1:1 to about 10:1 (w/w); preferably, the ratio is about 3:1 (w/w). More preferably, the ratio of the solution of O,O-dimethyldithiophosphoric acid in the organic solvent to water may be about 1:1. Mixing of the water and the solution of O,O-dimethyldithiophosphoric acid in the organic solvent produces a reaction mixture containing two layers, an organic and an aqueous layer. After separation of the organic and aqueous layers, the aqueous layer which now contains the O,O-dimethyldithiophosphoric acid may be washed with toluene. The aqueous solution of O,O-dimethyldithiophosphoric acid is then reacted with a diethyl maleate to form malathion. Diethyl fumarate may also be used in the reaction with the aqueous solution of O,O-dimethyldithiophosphoric acid to form malathion. Because diethyl maleate is not miscible with an aqueous solvent such as water, the reaction is performed as a heterogeneous, two layer mixture containing an aqueous layer (the aqueous solution of O,O-dimethyldithiophosphoric acid) and organic layer (diethyl maleate or diethyl fumarate). The two-phase mixture is subjected to mechanical mixing. Malathion collects in the lower or organic phase. The above reaction is done by direct addition of diethyl maleate to the aqueous solution of O,O-dimethyldithiophosphoric acid. An advantage of the present invention is that there is no need to isolate the O,O-dimethyldithiophosphoric acid in a concentrated form. O,O-dimethyldithiophosphoric acid is poisonous, thus, direct addition avoids the need to isolate any toxic compounds during the formation of malathion.

In order to maximize the yield and purity of the malathion, the conditions for reacting the aqueous solution of O,O-dimethyldithiophosphoric with the diethyl maleate, e.g., reaction temperature, reaction time, reagent ratio, may be optimized by those of ordinary skill in the art. In one embodiment, the molar ratio of diethyl maleate to O,O-dimethyldithiophosphoric acid may be from about 1:1 to about 2:1. The reaction temperature may range from about 25° C. to about 70° C.; more preferably, the reaction temperature is about 40° C. to about 65° C.; still more preferably, the reaction temperature is about 53° C. The reaction time may vary, e.g., (i) from about two (2) to about twelve (12) hours, (ii) from about five (5) to about ten (10) hours, or, (iii) about eight (8) hours. The reaction may be performed under a $N_2$ atmosphere. After completion of the reaction, the two solutions, the aqueous solution of O,O-dimethyldithiophosphoric and the diethyl maleate, are cooled to about 18° C. to about 25° C. temperature, the solutions separated and the diethyl maleate which contains the malathion washed at least two more times with water.

Diethyl fumarate may be formed during the reaction of the aqueous solution of O,O-dimethyldithiophosphoric acid with diethyl maleate. In order to decrease polymerization of diethyl maleate and diethyl fumarate, the reaction may be performed in the presence of a polymerization inhibitor. Suitable polymerization inhibitors include hydroquinone. The molar ratio of diethyl maleate to polymerization inhibitor is about 50:1 to about 500:1. For example, in one embodiment, the molar ratio of diethyl maleate to polymerization inhibitor is about 300:1.

In order to further purify the malathion, the diethyl maleate containing the malathion may be treated with a sulfur solution. The inventors of the present invention surprisingly found that a sulfur solution with a pH of less than about 7 is effective to eliminate dimer impurity formation. The pH of the sulfur solution ranges from about 6.0 to about 7.0. The sulfur solution may be for example, a (i) bisulfite, such as, sodium bisulfite, sodium metabisulfite, magnesium bisulfite or ammonium bisulfite, (ii) sulfite, such as, sodium sulfite, potassium sulfite, magnesium sulfite or ammonium sulfite, or (iii) sulfide such as, sodium sulfide, potassium sulfide, calcium sulfide, ammonium sulfide or ammonium bisulfide. The acidic, aqueous sulfur solution may be prepared in any suitable manner (note, an aqueous solution of a bisulfite is inherently acidic); suitable methods for preparing an acidic aqueous solution of a bisulfite include dissolving a bisulfite in water. Aqueous solutions of sulfites or sulfides are inherently basic. Therefore, an acidic, aqueous solution of a sulfite or sulfide may be prepared by dissolving a sulfite in water, followed by addition of an acid, such as, hydrochloric acid or sulfuric acid, to reduce the pH below 7.0. An advantage of the acidic sulfur solution is that it effectively increases the purity of malathion. The importance of using an acidic sulfur solution to further purify the malathion was demonstrated by the fact that if the malathion was treated with a basic solution (i.e., pH>7.0) of sulfites or sulfides, the resulting malathion was found to be contaminated with greater than 0.2% (w/w) tetraethyl dithiodisuccinate. In contrast, if the pH of the aqueous, sulfur solution was acidic, i.e., pH below 7.0, the malathion formed contained less than 0.2% (w/w) tetraethyl dithiodisuccinate. At pH 7-12, treatment of malathion with sulfur solution may also cause formation of tetraethyl thiodisuccinate impurity. An additional advantage of using acidic sulfur solution is to avoid malathion decomposition, which is known to occur more likely at a basic pH (i.e., pH>7). (See, e.g., Cotham W E Jr., et al. *Food Chem.* 37:824-828 (1989)).

In one embodiment, the diethyl maleate, which contains the malathion, is treated with a 20% (w/w) solution of sodium bisulfite (pH from about 6.1 to about 6.3). After mixing the diethyl maleate with the 20% (w/w) sodium bisulfite solution at about 60° C. for about 2 hours, the mixture containing the two solutions, diethyl maleate and 20% (w/w) sodium bisulfite, is cooled to about 18° C. to about 25° C. and the two solutions are then separated. The diethyl maleate is then washed with water and the two solutions, the diethyl maleate and water, separated; the diethyl maleate is then washed with a 5% (w/w) NaOH and the solutions separated. After washing with the NaOH, the diethyl maleate may be washed at least two (2) more times with water as described above.

At this stage of the purification, the purity of the malathion may be assayed by high pressure liquid chromatography (HPLC). Other techniques for assaying the purity of malathion and for determining the presence of impurities include, gas chromatography (GC), and nuclear magnetic resonance (NMR) spectroscopy (WHO Specifications and Evaluations for Public Health Pesticides: Malathion, World Health Organization, 2003). Using these analytical techniques, the presence of the following impurities may be determined, MeOOSPS, malaoxon, diethyl fumarate, dimethyl malathion, methyl malathion, isomalathion, O,O-methyl, ethyl S-(1,2-dicarboethoxy)ethyl phosphorodithioate, O,O-methyl, ethyl S-(1,2-dicarboethoxy)ethyl phosphorodithioate; in addition, the presence of any other detectable impurity may be determined using this methodology.

If the malathion contains greater than 5% (w/w) diethyl fumarate, the malathion is reprocessed by treating it again with the sulfur solution (pH 6.0-7.0), 5% (w/w) NaOH and water, sequentially, as described above. After reprocessing, the resulting malathion is assayed by HPLC for both the purity of malathion and for the presence of any of the impurities listed above.

At this stage of the purification, the malathion may exhibit the following purity/impurity profile: (i) greater than about 98.5% (w/w) malathion; (ii) less than about 5.0% (w/w) diethyl fumarate, and (iii) less than about 0.1% (w/w) isomalathion. In a preferred embodiment, the malathion may have the following purity/impurity profile: (i) greater than about 98.5% (w/w) malathion, (ii) less than about 0.2% (w/w) MeOOSPS, (iii) less than about 0.1% (w/w) malaoxon, (iv) less than about 0.2% (w/w) diethyl fumarate, (v) less than about 0.3% (w/w) methylmalathion, (vi) less than about 0.1% (w/w) isomalathion, and (vii) less than about 0.3% (w/w) O,O-methyl, ethyl S-(1,2-dicarboethoxy)ethyl phosphorodithioate. In addition, at this stage of the purification, there is not more than about 0.1% (w/w) of any other detectable impurity present in the malathion.

In order to reduce the levels of impurities further, the malathion prepared by the above process or malathion obtained from another synthetic route may be further purified by the distillation with water. Water is added to the malathion and the mixture subjected to azeotropic distillation. An advantage of this azeotropic distillation process is that it effectively removes MeOOSPS without producing the isomerization product of malathion (i.e., isomalathion). Additionally, azeotropic distillation is a more simple process as compared to air stripping or flash distillation. It is also much more effective in removing MeOOSPS. In one embodiment, the ratio of water to malathion is 3:1 (w/w). After the first distillation is completed, water is added, and azeotropic distillation repeated at least one more time. Again, the ratio of water to malathion at this stage in the purification may be about 3:1 (w/w). As long as there is a comparative excess of water present, the ratio of water to malathion may range from about 2:1 to greater than about 10:1 (w/w). After these additional purification steps, addition of water followed by azeotropic distillation, the purity of the malathion is determined by HPLC. The impurities assayed for can include, MeOOSPS, malaoxon, diethyl fumarate, dimethylmalathion, methylmalathion, isomalathion, malathion carboxylic acids as well as any other detectable impurity. If (i) MeOOSPS is greater than about 0.2% (w/w), (ii) malaoxon is greater than about 0.1% (w/w), (iii) diethyl fumarate is greater than about 0.2% (w/w), (iv) dimethylmalathion is greater than about 0.2% (w/w), (v) methylmalathion is greater than about 0.3% (w/w), (vi) isomalathion is greater than about 0.1% (w/w), (vii) any other individual detectable impurity is greater than 0.1% (w/w), or (viii) the malathion is less than about 98.5% (w/w), then, additional water is added to the malathion and azeotropic distillation repeated as described above. The purity/impurity profile of the malathion is then assayed a second time. Azeotropic distillation with the addition of water may be repeated until the purity/impurity profile the wet malathion conforms to the criteria set forth above for the purity of the malathion and for the % (w/w) of various impurities.

At this stage of the purification, the malathion may have the following purity/impurity profile:
  (i) greater than about 98.5% (w/w) malathion;
  (ii) less than about 0.2% (w/w) MeOOSPS;
  (iii) less than about 0.1% (w/w) malaoxon;
  (iv) less than about 0.2% (w/w) diethyl fumarate;
  (v) less than about 0.2% (w/w) dimethylmalathion;
  (vi) less than about 0.3% (w/w) methylmalathion; or,
  (vii) less than about 0.1% (w/w) isomalathion.

In another embodiment, the purity/impurity profile of malathion is: (i) greater than about 98.5% (w/w) malathion; (ii) less than about 0.2% (w/w) MeOOSPS; (iii) less than about 0.1% (w/w) malaoxon; (iv) less than about 0.2% (w/w) diethyl fumarate; (v) less than abut 0.2% (w/w) dimethylmalathion; (vi) less than about 0.3% (w/w) methylmalathion; (vii) less than about 0.1% (w/w) isomalathion; and, (viii) less than 0.1% (w/w) any other detectable impurity.

In a third embodiment, the purity/impurity profile is: (i) malathion greater than about 99.5% (w/w), (ii) about 0.1% (w/w) MeOOSPS, (iii) less than about 0.05% (w/w) malaoxon, (iii) less than about 0.01% (w/w) diethyl fumarate, (iv) less than about 0.02% dimethylmalathion, (v) about 0.06% (w/w) methylmalathion, and, (vi) 0.07% (w/w) isomalathion.

Malathion free of water may be obtained by heating the malathion after addition of water, followed by azeotropic distillation at a temperature from about 35° C. to about 45° C., together with air bubbling through the wet mass. The water content may be monitored by the Karl Fisher procedure. United States Pharmacopeia <921>. When the water content is reduced to not more than 0.1% (w/w), the malathion is cooled and filtered to remove any foreign particles. Filtration may be through glass paper.

After drying, the malathion is assayed by HPLC for the purity of malathion as well as for the presence of various impurities, including, MeOOSPO, MeOSSPO, malaxon, MeOOSPS, diethyl fumarate, dimethyl malathion, methyl malathion, O,O-methyl, ethyl S-(1,2-dicarboethoxy)ethyl phosphorodithioate, tetraethyl dithiosuccinate, isomalathion, malathion carboxylic acids such as O,O-dimethyl-S-(1-carboxy-2-carboxyethoxy) ethyl phosphorodithioate or O,O-dimethyl-S-(1-carboxy-2-carboxy) ethyl phosphorodithioate), mercaptosuccinate and tetraethyl thiodisuccinate. The HPLC assay of impurities may include all or only some of the impurities selected from the above list of impurities. In addition, the malathion may also be assayed for the presence of any other detectable impurities.

Various embodiments of malathion are encompassed by the invention including: (i) greater than about 98.5% (w/w) malathion, less than about 0.1% (w/w) MeOOSPO, less than about 0.1% (w/w) MeOSSPO, less than about 0.2% (w/w) MeOOSPS, less than about 0.3% (w/w) malathion carboxylic acid and/or less than about 0.1% (w/w) isomalathion; (ii) greater than about 98.5% (w/w) malathion, less than about 0.1% (w/w) MeOOSPO, less than about 0.1% (w/w) MeOSSPO, less than about 0.2% (w/w) MeOOSPS, less than about 0.3% (w/w) malathion carboxylic acid and/or less than about 0.02% (w/w) isomalathion; (iii) greater than about 99.0% (w/w) malathion, less than about 0.1% (w/w) MeOOSPO, less than about 0.1% (w/w) MeOSSPO and/or less than about 0.1% (w/w) MeOSSPS, 0.03% (w/w) malathion carboxylic acids and less than about 0.02% (w/w) isomalathion; and, (iv) greater than about 99.0% (w/w) malathion, less than about 0.04% (w/w) MeOOSPO, less than about 0.02% (w/w) MeOSSPO and/or less than about 0.1% (w/w) MeOSSPS, 0.03% (w/w) malathion carboxylic acids and less than about 0.02% (w/w) isomalathion.

The malathion prepared by the process of the invention was tested for storage stability. Malathion prepared by the process of the invention was stored under a variety of different temperature and humidity conditions for up to three (3) months. The storage conditions were:
  (i) 5° C., (ii) 25° C., 60% relative humidity and (iii) 30° C. and 60% relative humidity. The purity of the sample was determined after storage using HPLC. After storage, the malathion prepared by the process of the invention exhibits the following with respect to isomalathion and malathion:
  (i) less than about 0.1% (w/w) isomalathion and greater than 98.5% (w/w) malathion after storage at 5° C. for 3 months;

(ii) less than about 0.1% (w/w) isomalathion and greater than about 98.5% (w/w) malathion after storage for 3 months at 25° C. and 60% relative humidity; and, (iii) less than about 0.1% (w/w) isomalathion and greater than about 98.5% (w/w) malathion after storage for 3 months at 30° C. and 60% relative humidity.

"Unknown impurity" refers to any impurity other than tetraethyl dithiodisuccinate, O,O,S-trimethyl phosphorothioate (MeOOSPO), O,S,S-trimethyl phosphorodithioate (MeOSSPO), malaoxon, O,O,S-trimethyl phosphorodithioate (MeOOSPS), diethyl fumarate, dimethyl malathion, methyl malathion, O,O-methyl,ethyl S-(1,2-dicarboethoxy)ethyl-phosphorodithioate (O,O-Me,Et Malathion analog), and isomalathion.

Preparation of Malathion

The present invention provides an improved process for preparing pharmaceutical grade malathion. In one embodiment, the present invention provides a process for preparing malathion, comprising the steps of:

(a) reacting a phosphorus sulfide with methanol in an organic solvent to form an organic solution of O,O-dimethyldithiophosphoric acid;

(b) extracting O,O-dimethyldithiophosphoric acid from the organic solution into water to form an aqueous solution of O,O-dimethyldithiophosphoric acid; and (c) reacting the aqueous solution of O,O-dimethyldithiophosphoric acid with diethyl maleate to form malathion.

For example, we have found that the malathion obtained after step (c) typically contains less than 0.5% (w/w) of malaoxon, less than 0.1% (w/w) of isomalathion, less than 0.1% (w/w) of methyl malathion, and less than 0.3% (w/w) of tetraethyl dithiodisuccinate. In a specific example, we have found that the malathion obtained after step (c) contained less than 0.05% (w/w) of malaoxon, less than 0.04% (w/w) of isomalathion, less than 0.03% (w/w) of methyl malathion, and less than 0.05% (w/w) of tetraethyl dithiodisuccinate. If these impurities are present in malathion, they are very difficult to remove.

Preferably, the malathion obtained after step (c) contains less than 0.2% (w/w) of malaoxon. More preferably, the malathion obtained after step (c) contains less than 0.1% (w/w) of malaoxon. More preferably, the malathion obtained after step (c) contains less than 0.05% (w/w) of malaoxon.

Preferably, the malathion obtained after step (c) contains less than 0.07% (w/w) of isomalathion. More preferably, the malathion obtained after step (c) contains less than 0.04% (w/w) of isomalathion.

Preferably, the malathion obtained after step (c) contains less than 0.08% (w/w) of methyl malathion. More preferably, the malathion obtained after step (c) contains less than 0.03% (w/w) of methyl malathion.

Preferably, the malathion obtained after step (c) contains less than 0.2% (w/w) of tetraethyl dithiodisuccinate. More preferably, the malathion obtained after step (c) contains less than 0.1% (w/w) of tetraethyl dithiodisuccinate. More preferably, the malathion obtained after step (c) contains less than 0.05% (w/w) of tetraethyl dithiodisuccinate.

Purification of Malathion

Removing Diethyl Fumarate Impurity

Crude malathion prepared from diethyl maleate is typically contaminated with a significant amount of diethyl fumarate (e.g., ≥ 2% (w/w)). As previously discussed, it is very difficult to remove impurities such as diethyl fumarate from malathion using conventional purification processes (e.g., crystallization or distillation of malathion).

In another embodiment, the present invention provides a process for purifying malathion contaminated with diethyl fumarate, comprising the steps of:

(a) preparing an acidic aqueous solution containing at least one sulfur reagent selected from the group consisting of bisulfites, sulfites, and sulfides; and (b) contacting the contaminated malathion with the acidic aqueous solution at a pH below 7 to remove at least about 50% (w/w) of the diethyl fumarate from the contaminated malathion, wherein the purified malathion contains less than 0.2% (w/w) of tetraethyl dithiodisuccinate.

Without wishing to be bound by theory, it is believed that the present purification process operates by converting the diethyl fumarate impurity into a sulfur derivative, which is water-soluble and is removed into the aqueous phase. Specifically, it is believed that the sulfur reagent reacts with the carbon-carbon double bond of diethyl fumarate to create an ionic, water-soluble derivative containing a carbon-sulfur bond.

Surprisingly, we have discovered that if step (b) is performed at an acidic pH (i.e., below pH 7), the purified malathion contains less than 0.2% (w/w) of tetraethyl dithiodisuccinate. Preferably, the purified malathion contains 0.1% (w/w) or less of tetraethyl dithiodisuccinate. More preferably, the purified malathion contains 0.05% (w/w) or less of tetraethyl dithiodisuccinate.

We have further discovered that the rate of the step (b) reaction is slower at lower pH. Preferably, step (b) is performed at a pH of about 3 or above. More preferably, step (b) is performed at a pH of about 5 or above. More preferably, step (b) is performed at a pH of about 6.

As previously stated, an aqueous solution of a bisulfite is inherently acidic, having a pH of about 3-4. Suitable methods for increasing the pH of an aqueous solution of a bisulfite include, but are not limited to, adding a base to the aqueous solution. Suitable bases include, but are not limited to, sodium hydroxide and potassium hydroxide. Suitable bases further include sulfites and sulfides.

Step (b) may be performed at any suitable temperature. Preferably, step (b) is performed at a temperature of about 20° C. to about 65° C. More preferably, step (b) is performed at ambient temperature.

At least about 50% (w/w) of the diethyl fumarate is removed from the contaminated malathion during step (b). Preferably, at least about 70% (w/w) of the diethyl fumarate is removed from the contaminated malathion during step (b). More preferably, at least about 90% (w/w) of the diethyl fumarate is removed from the contaminated malathion during step (b). More preferably, at least about 95% (w/w) of the diethyl fumarate is removed from the contaminated malathion during step (b). More preferably, at least about 98% (w/w) of the diethyl fumarate is removed from the contaminated malathion during step (b). More preferably, at least about 99% (w/w) of the diethyl fumarate is removed from the contaminated malathion during step (b).

Preferably, the purified malathion contains 0.1% (w/w) or less of diethyl fumarate. More preferably, the purified malathion contains 0.05% (w/w) or less of diethyl fumarate.

Removing O,O,S-trimethyl phosphorodithioate (MeOOSPS) Impurity

Crude malathion prepared from O,O-dimethyldithiophosphoric acid is typically contaminated with a significant amount of O,O,S-trimethyl phosphorodithioate (MeOOSPS) (e.g., ≥ 2% (w/w)). As previously discussed, it is very difficult to remove impurities such as MeOOSPS from malathion using conventional purification processes (e.g., crystallization or distillation of malathion).

In another embodiment, the present invention provides a process for purifying malathion contaminated with O,O,S-trimethyl phosphorodithioate, comprising the steps of:
(a) mixing the contaminated malathion with water; and
(b) distilling water from the mixture at a temperature of about 60° C. or lower, to remove at least about 50% (w/w) of the O,O,S-trimethyl phosphorodithioate from the contaminated malathion,
wherein the purified malathion contains 0.1% (w/w) or less of isomalathion.

Without wishing to be bound by theory, it is believed that O,O,S-trimethyl phosphorodithioate forms an azeotrope with water, and that the present process operates by removing this azeotrope from the contaminated malathion.

Any suitable amount of water may be mixed with the contaminated malathion in step (a). Preferably, the ratio of water to contaminated malathion in step (a) is at least about 1:1 (w/w). More preferably, the ratio of water to contaminated malathion in step (a) is at least about 3:1 (w/w).

The process of the present invention removes at least about 50% (w/w) of the O,O,S-trimethyl phosphorodithioate from the contaminated malathion. Preferably, at least about 70% (w/w) of the O,O,S-trimethyl phosphorodithioate is removed from the contaminated malathion. More preferably, at least about 90% (w/w) of the O,O,S-trimethyl phosphorodithioate is removed from the contaminated malathion. More preferably, at least about 95% (w/w) of the O,O,S-trimethyl phosphorodithioate is removed from the contaminated malathion. More preferably, at least about 97% (w/w) of the O,O,S-trimethyl phosphorodithioate is removed from the contaminated malathion. More preferably, at least about 99% (w/w) of the O,O,S-trimethyl phosphorodithioate is removed from the contaminated malathion.

Preferably, the purified malathion contains 0.2% (w/w) or less of O,O,S-trimethyl phosphorodithioate. More preferably, the purified malathion contains 0.1% (w/w) or less of O,O,S-trimethyl phosphorodithioate.

Preparation of Pharmaceutical Grade Malathion

The above-described embodiments of the present invention may be performed sequentially to produce pharmaceutical grade malathion. In another embodiment, the present invention provides a process for preparing pharmaceutical grade malathion, comprising the steps of:
(a) reacting a phosphorus sulfide with methanol in an organic solvent to form an organic solution of O,O-dimethyldithiophosphoric acid;
(b) extracting O,O-dimethyldithiophosphoric acid from the organic solution into water to form an aqueous solution of O,O-dimethyldithiophosphoric acid;
(c) reacting the aqueous solution of O,O-dimethyldithiophosphoric acid with diethyl maleate to form malathion;
(d) preparing an acidic aqueous solution containing at least one sulfur reagent selected from the group consisting of bisulfites, sulfites, and sulfides;
(e) contacting the malathion with the acidic aqueous solution at a pH below 7;
(f) mixing the malathion with water; and
(g) distilling water from the mixture at a temperature of about 60° C. or lower, to form pharmaceutical grade malathion.

Preferably, the process further comprises after step (a) and before step (b) the steps of:
(i) filtering the organic solution of O,O-dimethyldithiophosphoric acid; and
(ii) concentrating the organic solution of O,O-dimethyldithiophosphoric acid.

Preferably, the pharmaceutical grade malathion contains 0.2% (w/w) or less of tetraethyl dithiodisuccinate. More preferably, the pharmaceutical grade malathion contains 0.1% (w/w) or less of tetraethyl dithiodisuccinate. More preferably, the pharmaceutical grade malathion contains 0.05% (w/w) or less of tetraethyl dithiodisuccinate.

Preferably, the pharmaceutical grade malathion contains 0.1% (w/w) or less of O,O,S-trimethyl phosphorothioate (MeOOSPO). More preferably, the pharmaceutical grade malathion contains 0.05% (w/w) or less of O,O,S-trimethyl phosphorothioate (MeOOSPO). More preferably, the pharmaceutical grade malathion contains 0.04% (w/w) or less of O,O,S-trimethyl phosphorothioate (MeOOSPO).

Preferably, the pharmaceutical grade malathion contains 0.1% (w/w) or less of O,S,S-trimethyl phosphorodithioate (MeOSSPO). More preferably, the pharmaceutical grade malathion contains 0.05% (w/w) or less of O,S,S-trimethyl phosphorodithioate (MeOSSPO). More preferably, the pharmaceutical grade malathion contains 0.02% (w/w) or less of O,S,S-trimethyl phosphorodithioate (MeOSSPO).

Preferably, the pharmaceutical grade malathion contains 0.1% (w/w) or less of malaoxon. More preferably, the pharmaceutical grade malathion contains 0.05% (w/w) or less of malaoxon.

Preferably, the pharmaceutical grade malathion contains 0.2% (w/w) or less of O,O,S-trimethyl phosphorodithioate (MeOOSPS). More preferably, the pharmaceutical grade malathion contains 0.1% (w/w) or less of O,O,S-trimethyl phosphorodithioate (MeOOSPS). More preferably, the pharmaceutical grade malathion contains 0.05% (w/w) or less of O,O,S-trimethyl phosphorodithioate (MeOOSPS).

Preferably, the pharmaceutical grade malathion contains 0.2% (w/w) or less of diethyl fumarate. More preferably, the pharmaceutical grade malathion contains 0.1% (w/w) or less of diethyl fumarate. More preferably, the pharmaceutical grade malathion contains 0.05% (w/w) or less of diethyl fumarate. More preferably, the pharmaceutical grade malathion contains 0.01% (w/w) or less of diethyl fumarate.

Preferably, the pharmaceutical grade malathion contains 0.2% (w/w) or less of dimethyl malathion. More preferably, the pharmaceutical grade malathion contains 0.1% (w/w) or less of dimethyl malathion. More preferably, the pharmaceutical grade malathion contains 0.05% (w/w) or less of dimethyl malathion. More preferably, the pharmaceutical grade malathion contains 0.02% (w/w) or less of dimethyl malathion.

Preferably, the pharmaceutical grade malathion contains 0.2% (w/w) or less of methyl malathion. More preferably, the pharmaceutical grade malathion contains 0.1% (w/w) or less of methyl malathion. More preferably, the pharmaceutical grade malathion contains 0.06% (w/w) or less of methyl malathion.

Preferably, the pharmaceutical grade malathion contains 0.2% (w/w) or less of O,O-methyl,ethyl S-(1,2-dicarboethoxy)ethyl-phosphorodithioate (O,O-Me,Et Malathion analog). More preferably, the pharmaceutical grade malathion contains 0.1% (w/w) or less of O,O-methyl,ethyl S-(1,2-dicarboethoxy)ethyl-phosphorodithioate (O,O-Me,Et Malathion analog). More preferably, the pharmaceutical grade malathion contains 0.05% (w/w) or less of O,O-methyl,ethyl S-(1,2-dicarboethoxy)ethyl-phosphorodithioate (O,O-Me,Et Malathion analog).

Preferably, the pharmaceutical grade malathion contains 0.1% (w/w) or less of isomalathion. More preferably, the pharmaceutical grade malathion contains 0.05% (w/w) or less of isomalathion. More preferably, the pharmaceutical grade malathion contains 0.02% (w/w) or less of isomalathion.

Preferably, the pharmaceutical grade malathion contains 0.1% (w/w) or less of each individual unknown impurity. By unknown impurity is meant any impurity other than tetraethyl dithiodisuccinate, O,O,S-trimethyl phosphorothioate (MeOOSPO), O,S,S-trimethyl phosphorodithioate (MeOSSPO), malaoxon, O,O,S-trimethyl phosphorodithioate (MeOOSPS), diethyl fumarate, dimethyl malathion, methyl malathion, O,O-methyl,ethyl S-(1,2-dicarboethoxy) ethyl-phosphorodithioate (O,O-Me,Et Malathion analog), and isomalathion.

Preferably, the process of the present invention is performed at a commercial scale. Preferably, the pharmaceutical grade malathion is produced as a single batch of at least about 100 grams. More preferably, the pharmaceutical grade malathion is produced as a single batch of at least about 500 grams. More preferably, the pharmaceutical grade malathion is produced as a single batch of at least about one (1) kilogram.

Pharmaceutical Grade Malathion

In another embodiment, the present invention provides a composition of pharmaceutical grade malathion, which contains 0.1% (w/w) or less of isomalathion, and 0.1% (w/w) or less of each individual unknown impurity present in the composition.

Preferably, the composition contains 0.05% (w/w) or less of isomalathion. More preferably, the composition contains 0.02% (w/w) or less of isomalathion.

Preferably, the composition contains less than 0.5% (w/w) of O,O,S-trimethyl phosphorothioate (MeOOSPO). More preferably, the composition contains less than 0.04% (w/w) of O,O,S-trimethyl phosphorothioate (MeOOSPO).

Preferably, the composition contains less than 0.1% (w/w) of methyl malathion. More preferably, the composition contains 0.08% (w/w) or less of methyl malathion. More preferably, the composition contains 0.06% (w/w) or less of methyl malathion.

Preferably, the composition contains less than 0.05% (w/w) of O,O,S-trimethyl phosphorothioate (MeOOSPO) and less than 0.1% (w/w) of methyl malathion. More preferably, the composition contains 0.05% (w/w) or less of isomalathion, less than 0.04% (w/w) of O,O,S-trimethyl phosphorothioate (MeOOSPO), and 0.08% (w/w) or less of methyl malathion. More preferably, the composition contains 0.02% (w/w) or less of isomalathion, less than 0.04% (w/w) of O,O,S-trimethyl phosphorothioate (MeOOSPO), and 0.06% (w/w) or less of methyl malathion.

Preferably, the composition is produced as a single batch of at least about 100 grams. More preferably, the composition is produced as a single batch of at least about 500 grams. More preferably, the composition is produced as a single batch of at least about one (1) kilogram.

Preferably, the composition is a commercial scale composition.

In another embodiment, the present invention provides a pharmaceutical formulation comprising the composition of pharmaceutical grade malathion.

In another embodiment, the present invention provides a process for preparing a pharmaceutical formulation of the composition of pharmaceutical grade malathion, comprising the step of mixing the composition of pharmaceutical grade malathion with at least one pharmaceutically acceptable excipient.

Storage Stable Commercial Scale Composition of Malathion

Surprisingly, the pharmaceutical grade malathion prepared in accordance with the present invention maintains a low level of isomalathion and other impurities during storage. In another embodiment, the present invention provides a commercial scale composition of pharmaceutical grade malathion, which contains 0.1% (w/w) or less of isomalathion after storing the composition for three (3) months at 25° C.±2° C. and 60%±5% relative humidity.

Preferably, the commercial scale composition of pharmaceutical grade malathion contains 0.05% (w/w) or less of isomalathion after storing the composition for three (3) months at 25° C.±2° C. and 60%±5% relative humidity. More preferably, the commercial scale composition of pharmaceutical grade malathion contains 0.04% (w/w) or less of isomalathion after storing the composition for three (3) months at 25° C.±2° C. and 60%±5% relative humidity.

Preferably, the commercial scale composition of pharmaceutical grade malathion contains 0.1% (w/w) or less of isomalathion after storing the composition for three (3) months at 30° C.±2° C. and 60%±5% relative humidity. More preferably, the commercial scale composition of pharmaceutical grade malathion contains 0.06% (w/w) or less of isomalathion after storing the composition for three (3) months at 30° C.±2°C. and 60%±5% relative humidity.

Preferably, the commercial scale composition of pharmaceutical grade malathion contains 0.1% (w/w) or less of isomalathion after storing the composition for two (2) months at 40° C.±2° C. and 75%±5% relative humidity. More preferably, the commercial scale composition of pharmaceutical grade malathion contains 0.1% (w/w) or less of isomalathion after storing the composition for three (3) months at 40° C.±2° C. and 75%±5% relative humidity.

Preferably, the commercial scale composition of pharmaceutical grade malathion contains less than 0.1% (w/w) of methyl malathion after storing the composition for three (3) months at 30° C.±2° C. and 60%±5% relative humidity. More preferably, the commercial scale composition of pharmaceutical grade malathion contains 0.06% (w/w) or less of methyl malathion after storing the composition for three (3) months at 30° C.±2° C. and 60%±5% relative humidity.

Preferably, the commercial scale composition of pharmaceutical grade malathion contains less than 0.1% (w/w) of methyl malathion after storing the composition for three (3) months at 40° C.±2° C. and 75%±5% relative humidity. More preferably, the commercial scale composition of pharmaceutical grade malathion contains 0.06% (w/w) or less of methyl malathion after storing the composition for three (3) months at 40° C.±2° C. and 75%±5% relative humidity.

Preferably, the commercial scale composition of pharmaceutical grade malathion contains less than 0.05% (w/w) of O,O,S-trimethyl phosphorothioate (MeOOSPO) after storing the composition for three (3) months at 30° C.±2° C. and 60%±5% relative humidity. More preferably, the commercial scale composition of pharmaceutical grade malathion contains 0.04% (w/w) or less of O,O,S-trimethyl phosphorothioate (MeOOSPO) after storing the composition for three (3) months at 30° C.±2° C. and 60%±5% relative humidity.

Preferably, the commercial scale composition of pharmaceutical grade malathion contains less than 0.05% (w/w) of O,O,S-trimethyl phosphorothioate (MeOOSPO) after storing the composition for two (2) months at 40° C.±2° C. and 75%±5% relative humidity. More preferably, the commercial scale composition of pharmaceutical grade malathion contains 0.05% (w/w) or less of methyl malathion after storing the composition for three (3) months at 40° C.±2° C. and 75%±5% relative humidity.

Preferably, the commercial scale composition of pharmaceutical grade malathion contains 0.1% (w/w) or less of each individual unknown impurity present in the composition after storing the composition for three (3) months at 25° C.±2° C. and 60%±5% relative humidity. More preferably, the commercial scale composition of pharmaceutical grade malathion contains 0.06% (w/w) or less of each individual unknown impurity present in the composition after storing the composition for three (3) months at 25° C.±2° C. and 60% ±5% relative humidity.

Preferably, the commercial scale composition of pharmaceutical grade malathion contains 0.1% (w/w) or less of each individual unknown impurity present in the composition after storing the composition for three (3) months at 5° C.±3° C. and ambient relative humidity. More preferably, the commercial scale composition of pharmaceutical grade malathion contains 0.06% (w/w) or less of each individual unknown impurity present in the composition after storing the composition for three (3) months at 5° C.±2° C. and ambient relative humidity. More preferably, the commercial scale composition of pharmaceutical grade malathion contains 0.04% (w/w) or less of each individual unknown impurity present in the composition after storing the composition for three (3) months at 5° C.±2° C. and ambient relative humidity.

Preferably, the commercial scale composition of pharmaceutical grade malathion contains 0.1% (w/w) or less of each individual unknown impurity present in the composition after storing the composition for two (2) months at 30° C.±2° C. and 60%±5% relative humidity. Preferably, the commercial scale composition of pharmaceutical grade malathion contains 0.15% (w/w) or less of each individual unknown impurity present in the composition after storing the composition for three (3) months at 30° C.±2° C. and 60%±5% relative humidity.

Preferably, the commercial scale composition of pharmaceutical grade malathion contains 0.1% (w/w) or less of each individual unknown impurity present in the composition after storing the composition for one (1) month at 40° C.±2° C. and 75%±5% relative humidity.

Preferably, the commercial scale composition of pharmaceutical grade malathion contains 0.1% (w/w) or less of each impurity present in the composition after storing the composition for three (3) months at 25° C.±2° C. and 60%±5% relative humidity. More preferably, the commercial scale composition of pharmaceutical grade malathion contains 0.06% (w/w) or less of each impurity present in the composition after storing the composition for three (3) months at 25° C.±2° C. and 60%±5% relative humidity.

Preferably, the commercial scale composition of pharmaceutical grade malathion contains 0.1% (w/w) or less of each impurity present in the composition after storing the composition for three (3) months at 5° C.±3° C. and ambient relative humidity. More preferably, the commercial scale composition of pharmaceutical grade malathion contains 0.06% (w/w) or less of each impurity present in the composition after storing the composition for three (3) months at 5° C.±2° C. and ambient relative humidity. More preferably, the commercial scale composition of pharmaceutical grade malathion contains 0.04% (w/w) or less of each impurity present in the composition after storing the composition for three (3) months at 5° C.±2C. and ambient relative humidity.

Preferably, the commercial scale composition of pharmaceutical grade malathion contains 0.1% (w/w) or less of each impurity present in the composition after storing the composition for two (2) months at 30° C.±2° C. and 60%±5% relative humidity. Preferably, the commercial scale composition of pharmaceutical grade malathion contains 0.15% (w/w) or less of each impurity present in the composition after storing the composition for three (3) months at 30° C.±2° C. and 60%±5% relative humidity.

Preferably, the commercial scale composition of pharmaceutical grade malathion contains 0.1% (w/w) or less of each impurity present in the composition after storing the composition for one (1) month at 40° C.±2° C. and 75%±5% relative humidity.

Methodology and Protocols

In-Process Purity Determination by HPLC

Purity was determined using a high performance liquid chromatography (HPLC) instrument with a variable wavelength detector.

(a) Chromatographic Conditions

| | |
|---|---|
| Column | BetaMax Neutral, 150X4.6 mm, 5 µm (or equivalent) |
| Detection | UV at 210 nm |
| Mobile Phase | Mixture of water:acetonitrile:methanol (480:370:150 v/v/v), with one (1) drop of 85% phosphoric acid for each 1,000 mL of mobile phase |
| Diluent | Mixture of water and acetonitrile (250:750 v/v), with one (1) drop of 85% phosphoric acid for each 1,000 mL of diluent |
| Flow Rate | 1.2 mL/min |
| Column temperature | 25° C. |
| Sample temperature | 25° C. |
| Injection volume | 10 µL |
| Run time | 40 min for standard solutions, 50 minutes for sample solutions |

(b) Known Impurities Resolution Solution

The following known impurities were used: malaoxon, isomalathion, O,O,S-trimethyl phosphorodithioate (MeOOSPS), diethyl fumarate, dimethyl malathion, and methyl malathion.

Each known impurity (about ten (10) mg) was added to a 10-mL volumetric flask, and the flask was then filled to volume with diluent. A 2 5 mL aliquot of this solution was transferred to 25-mL volumetric flask, and the flask was then filled to volume with diluent to provide the Known Impurities Stock Solution.

A malathion working standard (about fifty (50) mg) and diluent (about fifteen (15) mL) were added to a 25-mL volumetric flask, and the solution mixed to dissolve. To the flask was added five (5) mL of the Known Impurities Stock Solution, and the flask was then filled to volume with diluent to provide the Known Impurities Resolution Solution.

(c) Malathion Sample Solution

Approximately one hundred (100) mg of the malathion sample to be assayed, accurately weighed, was transferred into a 50-mL volumetric flask, and the flask was then filled to volume with diluent to provide the Malathion Sample Solution.

(d) System Suitability Test

The Known Impurities Resolution Solution was injected into the HPLC system. The resolution factor between isomalathion and MeOOSPS was not less than 1.7. The resolution factor between McOOSPS and diethyl fumarate was not less than 1.7. The resolution factor between diethyl fumarate and dimethyl malathion was not less than 2.0. Resolution factors were calculated according to the United States Pharmacopeia (USP) <621>. Typical chromatographic parameters are listed in the following table:

| Compound | Retention Time (min) | Relative Retention Time | Limit of Detection (LOD, %) | Limit of Quantitation (LOQ, %) | Relative Response Factor | Resolution |
|---|---|---|---|---|---|---|
| Malaoxon | 4.1 | 0.19 | 0.05 | 0.06 | 0.1 | — |
| Isomalathion | 5.7 | 0.27 | 0.04 | 0.05 | 0.3 | 5.2 |
| MeOOSPS | 6.4 | 0.30 | 0.02 | 0.03 | 1.1 | 2.0 |
| Diethyl fumarate | 7.1 | 0.33 | 0.01 | 0.02 | 8.8 | 1.9 |
| Dimethyl malathion | 8.7 | 0.41 | 0.02 | 0.03 | 1.2 | 3.7 |
| Methyl malathion | 13.5 | 0.63 | 0.03 | 0.04 | 1.1 | 7.6 |
| Malathion | 21.4 | 1.00 | 0.03 | 0.04 | 1.0 | 8.0 |

(e) Calculation of Impurity Content $$\% \text{ Impurity (w/w)} = \frac{Ssm \times 100}{Ssum \times RRF}$$

Ssm = Peak area of impurity obtained from sample solution chromatogram
Ssum = Sum of the areas of all peaks obtained from the sample solution chromatogram
RRF = Relative Response Factor
Notes: For unknown impurities, values of Limit of Detection and Limit of Quantitation as for malathion were used, and relative response factor RRF = 1. The toluene peak at RRT = 0.66 was ignored.

(f) Calculation of Malathion Purity $$\% \text{ Malathion purity (w/w)} = \frac{Ssm \times 100}{Ssum}$$

Ssm = Peak area of malathion obtained from sample solution chromatogram
Ssum = Sum of the areas of all peaks obtained from the sample solution chromatogram
Note: The toluene peak at RRT = 0.66 was ignored.

End-of-Process Determination of Assay, Purity, and Impurities Other Than Isomalathion Purity was determined using a high performance liquid chromatography (HPLC) instrument with a variable wavelength detector.

(a) Chromatographic Conditions
See above (In-Process Purity Determination by HPLC).

(b) Known Impurities Resolution Solution
The Known Impurities Stock Solution and Known Impurities Resolution Solution were prepared as above (In-Process Purity Determination by HPLC) using the following known impurities: malaoxon, O,O,S-trimethyl phosphorodithioate (MeOOSPS), O,O,S-trimethyl phosphorothioate (MeOOSPO), O,S,S-trimethyl phosphorodithioate (MeOSSPO), diethyl fumarate, dimethyl malathion, methyl malathion, and O,O-methyl,ethyl S-(1,2- dicarboethoxy) ethyl-phosphorodithioate (O,O-Me,Et Malathion analog).

(c) Malathion Standard Solution
Approximately one hundred (100) mg of malathion working standard, accurately weighed, was transferred into a 50-mL volumetric flask, and the flask was then filled to volume with diluent to provide the Malathion Standard Solution.

(d) Known Impurities Standard Solution
An aliquot (2.5 mL) of the Malathion Standard Solution was transferred into a 50-mL volumetric flask, and the flask was then filled to volume with diluent. An aliquot (2.5 mL) of the obtained solution was transferred into a 25-mL volumetric flask, and the flask was then filled to volume with diluent to provide the Known Impurities Standard Solution.

(e) Malathion Sample Solution
See above (In-Process Purity Determination by HPLC).

(f) System Suitability Test
One (1) injection of the Known Impurities Resolution Solution, six (6) replicate injections of the Known Impurities Standard Solution, and five (5) replicate injections of the Malathion Standard Solution were made.

The resolution factor between MeOSSPO and MeOOSPO was not less than 1.7. The resolution factor between MeOOSPS and diethyl fumarate was not less than 1.7. The resolution factor between diethyl fumarate and dimethyl malathion was not less than 2.0. Resolution factors were calculated according to the United States Pharmacopeia (USP) <621>.

The relative standard deviation of five (5) replicate injections of the Malathion Standard Solution was not more than 2.0%. The relative standard deviation of six (6) replicate injections of the Known Impurities Standard Solution was not more than 10.0%. If necessary, the mobile phase composition and/or flow rate were adjusted to meet the chromatographic parameters. Typical chromatographic parameters are listed in the table in Example 9.

End-of-Process Determination of Isomalathion
Isomalathion content was determined using a high performance liquid chromatography (HPLC) instrument with a variable wavelength detector.

(a) Chromatographic Conditions

| | |
|---|---|
| Column | BetaMax Neutral, 150X4.6 mm, 5 gm (or equivalent) |
| Detection | UV at 210 nm |
| Mobile Phase | Mixture of water:acetonitrile:methanol (500:470:30 v/v/v) |
| Diluent | Mixture of water and acetonitrile (250:750 v/v) |
| Flow Rate | 1.0 mL/min |
| Column temperature | 30° C. |
| Injection volume | 10 µl |
| Run time | 25 min for standard solutions, 45 minutes for sample solutions |

(b) Isomalathion Resolution Solution
Isomalathion (about ten (10) mg) was added to a 20-mL volumetric flask, and the flask was then filled to volume with diluent to provide the Isomalathion Stock Solution.

A malathion working standard (about one hundred (100) mg), accurately weighed was added to a 50-mL volumetric flask. To the flask was added 2.0 mL of the Isomalathion Stock Solution, and the flask was then filled to volume with diluent to provide the Isomalathion Resolution Solution.

(c) Isomalathion Standard Solution

The Isomalathion Standard Solution was prepared in the same way as the Known Impurities Standard Solution (see above).

(d) Malathion Sample Solution

See above (In-Process Purity Determination by HPLC).

(e) System Suitability Test

One (1) injection of the Isomalathion Resolution Solution and six (6) replicate injections of the Isomalathion Standard Solution were made.

The relative standard deviation of six (6) replicate injections of the Isomalathion Standard Solution was not more than 10.0%. If necessary, the mobile phase composition and/or flow rate were adjusted to meet the chromatographic parameters. Typical chromatographic parameters are listed in the table in Example 9.

(f) Calculation of Isomalathion Content $$\% \text{ Isomalathion (w/w)} = \frac{Wst \times Ssm \times Ast}{Sst \times Wsm \times RRF \times 200}$$

Wst = Weight of malathion standard in mg
Wsm = Weight of malathion sample in mg
Ssm = Peak area of isomalathion obtained from sample solution
Sst = Average peak area of malathion obtained from known impurity standard solution
Ast = Assay of malathion standard in percent
RRF = Relative Response Factor The malathion prepared by the process of the invention may be used for the preparation of malathion formulations such as Ovide® lotion and gels (see, U.S. Patent Application No. PCT/US05/24643 and 24558), lotions, creams or solutions.

The invention is further illustrated, but not limited by, the following examples.

EXAMPLE 1

Preparation of Dimethyl Dithiophosphoric Acid

Phosphorus pentasulfide (1.4 kg) and toluene (1.4 L) were combined under nitrogen in a 5-L jacketed glass reactor equipped with mechanical stirrer, and the resulting suspension was heated with stirring to about 60° C. Methanol (1.1 L) was added dropwise over the course of four (4) hours and fifteen (15) minutes, while maintaining the temperature of the reaction mass at 67° C. or lower. The resulting gaseous $H_2S$ was trapped using an aqueous solution of sodium hypochlorite/sodium hydroxide. After complete addition of the methanol, the mixture was stirred at 55-65° C. for an additional one (1) hour.

The mixture was cooled to a temperature of 22-30° C. and the mixture was filtered to remove unreacted phosphorus pentasulfide. Additional toluene (0.3 L) was added to the resulting filtrate. The mixture was distilled under vacuum ($\leq$200 mbar) at a temperature of about 50-60° C. to remove about 600 mL of toluene. The resulting concentrate was cooled to a temperature of 22-30° C. and water (3 kg) was added. The two phases were mixed for 20 minutes, and then the phases were separated. The aqueous phase was washed with toluene (0.3 L), and the aqueous phase again was separated, to provide an aqueous solution of dimethyldithiophosphoric acid (about 4.22 kg containing about 1.22 kg of dimethyldithiophosphoric acid).

EXAMPLE 2

Preparation of Malathion

The solution of dimethyl dithiophosphoric acid was added to diethyl maleate (the ratio of dimethyl dithiophosphoric acid to diethyl maleate was approximately 1-1.25 kg: 1.2 kg). Hydroquinone (approximately 3 grams) was added to the mixture. The reaction mixture which contains two separate solutions, an organic solution of diethyl maleate and an aqueous solution of dimethyl dithiophosphoric acid, was mixed for about 8 hours at 53° C. under a nitrogen atmosphere. After mixing, the reaction was cooled to ambient temperature and the organic and aqueous solutions were separated. The organic or diethyl maleate solutions which contained malathion was washed two (2) times with water (approximately 1 liter each time). The organic and aqueous solutions were separated and the malathion in the solution of diethyl maleate retained. This reaction yielded approximately 1.5-1.9 kg of malathion.

EXAMPLE 3

Purification of the Malathion

The solution of diethylmaleate (organic) which contained the malathion (approximately 1.5-1.9 kg) was treated with about 4.6 kg of a 20% sodium bisulfite solution (aqueous) (pH 6.1-6.3) at 60° C. for 2 hours. The mixture was cooled to ambient temperature and the organic and aqueous layers separated; the organic layer was washed with water (approximately 1.5 kg). The organic and aqueous layers were separated. The organic layer was then washed with a 0.5% NaOH solution. After separation of the two layers, the organic layer containing the malathion was washed twice with water (approximately 1 liter of water was used for each wash) to yield, approximately 0.75-0.95 kg of malathion. The purity of the malathion at this stage was determined by HPLC. If more than 5% (w/w) diethyl fumarate was present in the malathion, the material was reprocessed by treatment with the sodium bisulfite solution and water. After reprocessing, the malathion was assayed a second time for purity. This reprocessing step could be repeated until the purity profile of the malathion conformed with the diethyl fumarate cut-off set forth above.

EXAMPLE 4

Analysis of Malathion after Purification

The purity of malathion and the percentage of impurities present were determined by HPLC instrument with a variable wavelength detector. The mobile phase composition and/or flow rate were adjusted to meet the chromatographic parameters. The results of the HPLC analyses for two different sample batches of malathion are shown below in Table I.

TABLE I

| HPLC Analysis of Malathion | | |
|---|---|---|
| Analyte | Malathion (%(w/w)) (Batch A) | Malathion (%(w/w)) (Batch B) |
| MeOOSPS | 0.12 | 0.14 |
| Malaoxon | <0.05 | <0.05 |
| Diethyl fumarate | <0.01 | <0.01 |
| Dimethylmalathion | <0.02 | <0.02 |
| Methylmalthion | 0.06 | 0.06 |

TABLE I-continued

HPLC Analysis of Malathion

| Analyte | Malathion (%(w/w)) (Batch A) | Malathion (%(w/w)) (Batch B) |
|---|---|---|
| Isomalthion | <0.04 | <0.04 |
| O,O-methyl, ethyl S-(1,2-dicarboethoxy)ethyl phosphorodithioate | 0.18 | 0.12 |
| Any other detectable impurity | 0.10 | <0.04 |
| Malathion Purity | 99.5 | 99.6 |

EXAMPLE 5

Azeotropic Distillation of Malathion

Water (2.8 kg) was added to the malathion formed as described in Example 4 and the resulting two-phase mixture subjected to azeotropic distillation over the course of four days at a temperature of about 35-50° C. and a pressure of about 30-60 mbar. Water was added to the mixture at approximately one-hour intervals to replace the quantity removed by azeotropic distillation during that period (about 0.2-0.7 L each time). A total of about 34.2 L of water was distilled during this process. The two-phase mixture was cooled to 22-30° C., and the phases were separated, providing malathion (0.84 kg) (note, the malathion is wet, i.e., contains water).

The purity of the obtained malathion was determined using HPLC; the results are shown in Table II.

TABLE II

Analysis of Malathion after Azeotropic Distillation

| Compound | Quantity (% w/w) |
|---|---|
| <0.01 (LOD) Diethyl fumarate | |
| Isomalathion | 0.07 |
| MeOOSPS | 0.1 |
| Malaoxon | <0.05 (LOD) |
| Dimethyl malathion | <0.02 (LOD) |
| Methyl malathion | 0.06 |
| Malathion purity | 99.5 |

These data demonstrate that at least 97% (w/w) of the MeOOSPS was removed from the malathion of Example 3. These data further demonstrate that the purified malathion contained only 0.07% (w/w) of isomalathion.

EXAMPLE 6

Analysis of Sample Batches of Malathion Prepared by the Process of this Invention In Table III set forth below, three different batches of malathion prepared by the process of the invention (these batches are noted in the table as A, B and C) were analyzed after drying by HPLC for malathion purity and for the presence of impurities as set forth above. As a comparison, the following samples of malathion were analyzed, malathion approved for pharmaceutical use from the United States Pharmacopeia ("USP") and malathion used for pharmaceutical preparations obtained from Cheminova (referered to herein as, Cheminova A/S, Thyborønvej 78 DK-7673 Harboøre, Denmark). The purity of these samples, USP and Cheminova, was compared with the purity of the malathion prepared by the process of the invention. The results of the analysis are shown in Table III.

TABLE III

HPLC Analysis of Malathion Prepared by the Process of the Invention after Drying and Comparison with Malathion from the USP and Cheminova***

| Batch | Malathion | MeOOSPO | MeOSSPO | Malaxon | MeOOSPS | Diethyl Fumarate | Dimethyl Malathion | Methyl Malathion |
|---|---|---|---|---|---|---|---|---|
| A | 99.3 | <0.04 | <0.02 | <0.05 | 0.1 | <0.01 | <0.02 | 0.07 |
| B | 99.2 | <0.04 | <0.02 | <0.05 | 0.1 | <0.01 | <0.02 | 0.07 |
| C | 99.2 | <0.04 | <0.02 | <0.05 | 0.2 | <0.01 | <0.02 | 0.06 |
| USP | | <0.04 | 0.04 | <0.05 | 0.09 | 0.05 | <0.02 | 0.17 |
| I*** | | 0.05 | <0.02 | <0.05 | 0.05 | 0.02 | <0.02 | 0.2 |
| II*** | | 0.05 | <0.02 | 0.07 | 0.06 | <0.02 | <0.02 | 0.1 |
| III*** | | 0.06 | <0.02 | <0.05 | 0.04 | 0.02 | <0.02 | 0.2 |

| Batch | O,O methyl, ethyl S-(1,2-dicarboethoxy)ethyl phosphorodithioate | Tetraethyl dithiodi-succinate | Isomalathion | Malathion Carboxylic Acids | Mercapto Succinate | Tetraethyl thiodi-succinate |
|---|---|---|---|---|---|---|
| A | 0.1 | 0.05 | <0.02 | <0.03 | 0.01 | ND* |
| B | 0.1 | 0.06 | <0.02 | <0.03 | 0.01 | ND |
| C | 0.1 | 0.05 | <0.02 | <0.03 | 0.01 | ND |
| USP | 0.14 | <0.03 | 0.27 | 0.77 | 0.04 | ND |
| I*** | — | — | 0.2 | — | — | — |
| II*** | — | — | 0.2 | — | — | — |
| III*** | — | — | 0.2 | — | — | — |

*ND—not detected
**all numbers presented as (w/w)%
***I-III commercial sample of pharmaceutical grade malathion obtained from Cheminova. Samples were stored for at least 1 year under proper storage conditions prior to analysis.

When compared with the USP malathion, malathion prepared by the methods of the present invention has less isomalathion, <0.02% (w/w) versus 0.27% (w/w) USP malathion. In addition, there is less (i) MeOSSPO present, <0.02% (w/w), malathion prepared by the methods of the present invention, versus 0.04% (w/w), USP malathion, (ii) diethyl fumarate, <0.01% (w/w), malathion prepared by the methods of the present invention, versus 0.05% (w/w), USP malathion, (iii) methyl malathion, 0.06-0.07% (w/w), malathion prepared by the methods of the present invention versus 0.17% (w/w), USP malathion, (iv) malathion carboxylic acids, <0.03% (w/w), malathion prepared by the methods of the present invention versus 0.77% (w/w), USP malathion, and mercapto succinate, 0.01% (w/w), malathion prepared by the methods of the present invention versus 0.04% (w/w), USP malathion.

When compared with malathion from Cheminova, malathion prepared by the methods of the present invention has less isomalathion, <0.02% (w/w) versus 0.2% (w/w) malathion from Cheminova. In addition, there is less (i) MeOOSPO present, <0.02% (w/w), malathion prepared by the methods of the present invention, versus 0.05% (w/w), USP malathion, (ii) diethyl fumarate, <0.01% (w/w), malathion prepared by the methods of the present invention, versus 0.02% (w/w), malathion from Cheminova, and, (iii) methyl malathion, 0.06-0.07% (w/w), malathion prepared by the methods of the present invention versus 0.1-0.2% (w/w), malathion from Cheminova.

In one embodiment, the malathion prepared by the process of the present invention, comprises, malathion greater than about 98.0% (w/w) malathion and less than about 0.1% (w/w) isomalathion and less than 0.1% (w/w) malathion monoacid. In another embodiment, the malathion prepared by the process of the present invention contains greater than about 98.0% (w/w) malathion and less than about 0.05% (w/w) isomalathion. In a third embodiment, the amount of isomalathion present is less than about 0.02% (w/w).

The malathion prepared by the process of the invention may also contain greater than about 98.5% (w/w) malathion, less than about 0.2% (w/w) MeOOSPS, less than about 0.1% (w/w) malaoxon, less than about 0.2% (w/w) diethyl fumarate, less than abut 0.2% (w/w) dimethylmalathion, less than about 0.3% (w/w) methylmalathion, and less than about 0.1% (w/w) isomalathion. In another embodiment, the malathion prepared by the process of the invention contains greater than about 99.0% (w/w) malathion, less than about 0.1% (w/w) MeOOSPS, less than about 0.05% (w/w) malaoxon, less than about 0.01% (w/w) diethyl fumarate, less than about 0.02% (w/w) dimethylmalathion, less than about 0.07% (w/w) methylmalathion, and less than about 0.02% (w/w) isomalathion. In each of the embodiments listed above for malathion prepared by the process of the invention, the amount of any other detectable impurity may be less than 0.1% (w/w).

Embodiments of malathion at this stage of the purification include:

(i) greater than about 98.5% (w/w) malathion, less than about 0.1% (w/w) MeOOSPO, less than about 0.1% (w/w) MeOSSPO, less than about 0.1% (w/w) malaxon, less than about 0.2% (w/w) MeOOSPS, less than about 0.2% (w/w) diethyl fumarate, less than about 0.3% (w/w) methyl malathion, and/or less than about 0.1% (w/w) isomalathion;

(ii) greater than about 98.5% (w/w) malathion, less than about 0.1% (w/w) MeOOSPO, less than about 0.1% (w/w) MeOSSPO, less than about 0.1% (w/w) malaxon, less than about 0.2% (w/w) MeOOSPS, less than about 0.2% (w/w) diethyl fumarate, less than about 0.3% (w/w) methyl malathion, less than about 0.3% (w/w) O,O methyl, ethyl S-(1,2-dicarboethoxy)ethyl phosphorodithioate, less than about 0.3% (w/w) malathion carboxylic acids and/or less than about 0.1% (w/w) isomalathion;

(iii) greater than about 99.0% (w/w) malathion, less than about 0.1% (w/w) MeOOSPO, less than about 0.1% (w/w) MeOSSPO, less than about 0.1% (w/w) malaxon, less than about 0.2% (w/w) MeOOSPS, less than about 0.2% (w/w) diethyl fumarate, less than about 0.3% (w/w) methyl malathion, and/or less than about 0.1% (w/w) isomalathion;

(iv) greater than about 99.0% (w/w) malathion, less than about 0.1% (w/w) MeOOSPO, less than about 0.1% (w/w) McOSSPO, less than about 0.1% (w/w) malaxon, less than about 0.2% (w/w) MeOOSPS, less than about 0.2% (w/w) diethyl fumarate, less than about 0.3% (w/w) methyl malathion, less than about 0.3% (w/w) O,O methyl, ethyl S-(1,2-dicarboethoxy)ethyl phosphorodithioate, less than about 0.3% (w/w) malathion, less than about 0.3% (w/w) malathion carboxylic acids (O,O-dimethyl-S-(1-carboxy-2-carboxyethoxy) ethyl phosphorodithioate and/or O,O-dimethyl-S-(1-carboxy-2-carboxy) ethyl phosphorodithioate) less than 0.1% (w/w) isomalathion;

(v) greater than about 99.0% (w/w) malathion, less than about 0.1% (w/w) isomalathion and/or less than about 0.3% (w/w) malathion carboxylic acids;

(vi) greater than about 99.0% (w/w) malathion, less than about 0.02% (w/w) isomalathion and/or less than about 0.03% (w/w) malathion carboxylic acids;

(vii) greater than about 99.0% (w/w) malathion, less than about 0.02% (w/w) isomalathion, less than about 0.03% (w/w) malathion carboxylic acids, less than about 0.1% (w/w) MeOOSPO, less than about 0.1% (w/w) MeOSSPO and/or less than about 0.2% (w/w) McOSSPS; and, (viii) greater than about 99.0% (w/w) malathion, less than about 0.02% (w/w) isomalathion, less than about 0.03% (w/w) malathion carboxylic acids, less than about 0.04% (w/w) MeOOSPO, less than about 0.02% (w/w) MeOSSPO and/or less than about 0.1% (w/w) MeOSSPS. Additionally, in any of the above embodiments, there may be less than 0.1% (w/w) of any other detectable impurity present in the malathion at this stage of the purification.

EXAMPLE 7

Storage Stability of Malathion

Table IV presents the analytical data showing storage of two, different batches of malathion after storage under a variety of different conditions.

TABLE IV

Analysis of Malathion Prepared by the Process of the Invention after Storage under Different Conditions for 3 Months*

| Compound | Baseline** | Storage at 5° C. | Storage at 25° C., 60% relative humidity | Storage at 30° C. and 60% relative humidity | Storage at 40° C. and 75% relative humidity |
|---|---|---|---|---|---|
| (a) Batch I | | | | | |
| MeOOSPO | <0.04 | <0.04 | <0.04 | <0.04 | 0.05 |
| MeOSSPO | <0.02 | <0.02 | <0.02 | <0.02 | <0.02 |
| MeOOSPS | 0.1 | 0.1 | 0.1 | 0.1 | 0.2 |
| Malaoxon | <0.05 | <0.02 | <0.02 | <0.02 | <0.05 |
| Diethyl fumarate | <0.01 | <0.01 | <0.01 | <0.01 | <0.02 |
| Dimethyl malathion | <0.02 | <0.02 | <0.02 | <0.02 | <0.02 |
| Methyl malathion | 0.06 | 0.06 | 0.06 | 0.06 | 0.06 |
| Isomalathion | 0.06 | <0.05 | 0.04 | 0.06 | 0.1 |
| Malathion Purity | 99.5 | 99.7 | 99.0 | 99.0 | 97.5 |
| (b) Batch II | | | | | |
| MeOOSPO | <0.04 | <0.04 | <0.04 | <0.04 | 0.05 |
| MeOSSPO | <0.02 | <0.09 | <0.02 | <0.02 | <0.02 |
| MeOOSPS | 0.09 | 0.1 | 0.09 | 0.1 | 0.2 |
| Malaxon | <0.05 | <0.05 | <0.05 | <0.05 | <0.05 |
| Diethyl fumarate | <0.06 | <0.01 | <0.01 | <0.01 | <0.02 |
| Dimethyl malathion | <0.02 | <0.02 | <0.02 | <0.02 | <0.02 |
| Methyl malathion | 0.08 | 0.07 | 0.07 | 0.08 | 0.08 |
| Isomalathion | <0.04 | <0.05 | 0.07 | 0.08 | 0.2 |
| Malathion Purity | 99.5 | 99.7 | 99.4 | 99.1 | 97.4 |

*All data is shown as % (w/w)
**Baseline - results at time 0.

Table IV shows the results of the HPLC analysis after three months of storage conditions under these test conditions for two different batches of malathion prepared by the process of this invention.

The invention provides for a malathion characterized by the fact that it is stable after storage under a variety of different conditions. Stability may be characterized by the fact that the levels of isomalathion, MeOOSPO, MeOSSPO and MeOOSPS do not exceed 0.2% (w/w) after storage.

After storage at 5° C. for 3 months, the malathion may have the following purity/impurity profile, greater than about 98.5% (w/w) malathion, less than about 0.1% (w/w) MeOOSPO, less than about 0.1% (w/w) MeOSSPO, less than about 0.1% (w/w) malaxon, less than about 0.2% (w/w) MeOOSPS, less than about 0.2% (w/w) diethyl fumarate, less than about 0.2% (w/w) dimethylmalathion, less than about 0.3% (w/w) methylmalathion and/or less than about 0.1% (w/w) isomalathion. In another embodiment, the profile for the malathion after storage at 5° C. for 3 months is greater than about 99.7% (w/w) malathion, less than about 0.04% (w/w) MeOOSPO, less than about 0.02% (w/w) MeOSSPO, less than about 0.05% (w/w) malaxon, less than about 0.1% (w/w) MeOOSPS, less than about 0.01% (w/w) diethyl fumarate, less than about 0.02% (w/w) dimethylmalathion, less than about 0.06% (w/w) methylmalathion and/or less than about 0.05% (w/w) isomalathion.

After storage for 3 months at 25° C., 60% relative humidity the malathion may have the following purity/impurity profile, greater than about 98.5% (w/w) malathion, less than about 0.1% (w/w) MeOOSPO, less than about 0.1% (w/w) MeOSSPO, less than about 0.1% (w/w) malaxon, less than about 0.2% (w/w) MeOOSPS, less than about 0.2% (w/w) diethyl fumarate, less than about 0.2% (w/w) dimethylmalathion, less than about 0.3% (w/w) methylmalathion and/or less than about 0.1% (w/w) isomalathion. In a second embodiment, the malathion has the following profile after storage for 3 months at 25° C., 60% relative humidity, greater than about 99.0% (w/w) malathion, less than about 0.04% (w/w) MeOOSPO, less than about 0.02% (w/w) MeOSSPO, less than about 0.05% (w/w) malaxon, less than about 0.1% (w/w) MeOOSPS, less than about 0.01% (w/w) diethyl fumarate, less than about 0.02% (w/w) dimethylmalathion, less than about 0.06% (w/w) methylmalathion and/or less than about 0.04% (w/w) isomalathion.

After storage for 3 months at 30° C. and 60% relative humidity, the malathion may have the following purity/impurity profile, greater than about 98.5% (w/w) malathion, less than about 0.1% (w/w) MeOOSPO, less than about 0.1% (w/w) MeOSSPO, less than about 0.1% (w/w) malaxon, less than about 0.2% (w/w) MeOOSPS, less than about 0.2% (w/w) diethyl fumarate, less than about 0.2% (w/w) dimethylmalathion, less than about 0.3% (w/w) methylmalathion and/or less than about 0.1% (w/w) isomalathion. In a second embodiment, the malathion has the following profile after storage at 30° C., 60% relative humidity, greater than about 99.0% (w/w) malathion, less than about 0.04% (w/w) MeOOSPO, less than about 0.02% (w/w) MeOSSPO, less than about 0.05% (w/w) malaxon, less than about 0.1% (w/w) MeOOSPS, less than about 0.01% (w/w) diethyl fumarate, less than about 0.02% (w/w) dimethylmalathion, less than about 0.06% (w/w) methylmalathion and/or less than about 0.04% (w/w) isomalathion.

After storage for 3 months at 40° C. and 75% relative humidity, the malathion has the following purity/impurity profile, greater than about 97.0% (w/w) malathion, less than about 0.1% (w/w) MeOOSPO, less than about 0.1% (w/w) MeOSSPO, less than about 0.1% (w/w) malaxon, less than about 0.2% (w/w) MeOOSPS, less than about 0.2% (w/w) diethyl fumarate, less than about 0.2% (w/w) dimethylmalathion, less than about 0.3% (w/w) methylmalathion and/or less than about 0.1% (w/w) isomalathion. In a second embodiment, the malathion has the following purity/impurity profile after storage for 3 months at 40° C., 75% relative humidity, greater than about 97.5% (w/w) malathion, less than about 0.05% (w/w) MeOOSPO, less than about 0.02% (w/w) MeOSSPO, less than about 0.05% (w/w) malaxon, less than about 0.2% (w/w) MeOOSPS, less than about 0.02% (w/w) diethyl fumarate, less than about 0.02% (w/w) dimethylmalathion, less than about 0.06% (w/w) methylmalathion and/or less than about 0.1% (w/w) isomalathion.

EXAMPLE 8

An example of a lotion formulation prepared using malathion prepared by the process of the present invention comprises the following components:

TABLE V

Malathion Lotion

| Ingredient | % (w/w) |
|---|---|
| Isopropyl Alcohol | 70* |
| Terpineol | 12.672 |
| Dipentene | 10.493 |
| Malathion | 0.654 |
| Pine Needle Oil | 0.284 |

*the amount of isopropyl alcohol may be increased so that the sum of all percentages of the various ingredients equals one hundred percent (100%).

The stability of the malathion prepared by the process of the invention in a malathion lotion formulation (Table V) was tested under a variety of different storage conditions. The percentages of impurities under each storage condition were assayed. The results are shown in Table VI. In one embodiment, the malathion in the lotion has the following purity/impurity profile after storage at 5° C. for 3 months, less than about 0.5% (w/w) diethyl fumarate, less than about 0.5% (w/w) methylmalathion, less than about 0.1% (w/w) isomalathion, less than about 0.1% (w/w) malaoxon, and/or less than about 0.5% (w/w) dimethylmalathion. In addition, in this embodiment, there is less than 0.5% (w/w) of any other detectable impurity present. In another embodiment, the malathion in the lotion has the following purity/impurity profile after storage at 5° C. for 3 months, less than about 0.02% (w/w) diethyl fumarate, less than about 0.2% (w/w) methylmalathion, less than about 0.05% (w/w) isomalathion, less than about 0.03% (w/w) malaxon, and/or less than about 0.03% (w/w) dimethylmalathion.

After storage for 3 months at 25° C., 60% relative humidity, the malathion in the lotion has the following purity/impurity profile, less than about 0.5% (w/w) diethyl fumarate, less than about 0.5% (w/w) methylmalathion, less than about 0.1% (w/w) isomalathion, less than about 0.03% (w/w) malaoxon, and/or less than about 0.03% (w/w) dimethylmalathion. In addition, in this embodiment, there is less than 0.5% (w/w) of any other detectable impurity present. In another embodiment, the malathion in the lotion has the following purity/impurity profile after storage at 5° C. for 3 months, less than about 0.01% (w/w) diethyl fumarate, less than about 0.1% (w/w) methylmalathion, less than about 0.05% (w/w) isomalathion, less than about 0.03% (w/w) malaxon, and/or less than about 0.03% (w/w) dimethylmalathion.

After storage for 3 months at 30° C. and 60% relative humidity, the malathion in the lotion has the following purity/impurity profile, less than about 0.5% (w/w) diethyl fumarate, less than about 0.5% (w/w) methylmalathion, less than about 0.1% (w/w) isomalathion, less than about 0.03% (w/w) malaoxon, and/or less than about 0.03% (w/w) dimethylmalathion. In this embodiment, there is less than 0.5% (w/w) of any other detectable impurity present. In a second embodiment under these storage conditions (30° C. and 60% relative humidity) the malathion in the lotion has the following purity/impurity profile, less than about 0.02% (w/w) diethyl fumarate, less than about 0.02% (w/w) methylmalathion, less than about 0.05% (w/w) isomalathion, less than about 0.03% (w/w) malaoxon, and/or less than about 0.03% (w/w) dimethylmalathion.

After storage for 3 months at 40° C. and 75% relative humidity, the malathion in the lotion has the following purity/impurity profile, less than about 0.5% (w/w) diethyl fumarate, less than about 0.5% (w/w) methylmalathion, less than about 0.1% (w/w) isomalathion, less than about 0.03% (w/w) malaoxon, and/or less than about 0.03% (w/w) dimethylmalathion. In this embodiment, there is less than 0.5% (w/w) of any other detectable impurity present. Under these storage conditions, in a second embodiment, the malathion in the lotion has the following profile, less than about 0.01% (w/w) diethyl fumarate, less than about 0.04% (w/w) methylmalathion, less than about 0.07% (w/w) isomalathion, less than about 0.03% (w/w) malaoxon, and/or less than about 0.22% (w/w) dimethylmalathion.

TABLE VI

Stability of Malathion in a Malathion Lotion after three (3) months after storage under different conditions

| Compound | Baseline Time 0 | Storage at 5° C. | Storage at 25° C., 60% relative humidity | Storage at 30° C. and 60% relative humidity | Storage at 40° C. and 75% relative humidity |
|---|---|---|---|---|---|
| Malaoxon | <0.1 | <0.03 | <0.03 | <0.03 | <0.03 |
| Diethyl fumarate | <0.5 | 0.02 | 0.01 | 0.02 | 0.01 |
| Dimethyl malathion | <0.5 | <0.03 | <0.03 | <0.03 | 0.22 |
| Methyl malathion | <0.05 | 0.2 | 0.1 | <0.02 | <0.04 |
| Isomalathion | <0.1 | <0.05 | <0.05 | <0.05 | 0.07 |

EXAMPLE 9

Analytical Methods

MeOOSPO, MeOSSPO, malaxon, MeOOSPS, diethyl fumarate, dimethyl malathion, methyl malathion, O,O-methyl, ethyl S-(1,2-dicarboethoxy)ethyl phosphorodithioate, tetraethyl dithiosuccinate, isomalathion, malathion carboxylic acids, mercaptosuccinate and the tetraethyl thiodisuccinate were assayed for by HPLC. The mobile phase was a mixture of water, acetonitrile and methanol (480:370:150) and one drop of 85% phosphoric acid for each 1000 ml of mobile phase. Method validation was performed and system reproducibility, linearity, repeatability, intermediate precision, recovery of related compounds and sensitivity were assessed according to standard methology (U.S. Pharmacopeia, 2004, U.S. Pharmacopeial Convention, Inc., 12601 Twinbrook Parkway, Rockville, Md. 20852). If necessary, the mobile phase composition and/or flow rate were adjusted to meet the chromatographic parameters. The analytical parameters for various impurities and for malathion is shown below in Table VII.

(a) Calculation of Malathion Assay $$\% \text{ Assay (as is) } (w/w) = \frac{Wst \times Ssm \times Ast}{Sst \times Wsm}$$

Wst=Weight of malathion standard in mg
Wsm=Weight of malathion sample in mg
Ssm=Peak area of malathion obtained from malathion sample solution
Sst=Average peak area of malathion obtained from malathion standard solution
Ast=Assay of malathion standard in percent (b) Calculation of Impurity Content
% known or unknown impurity (an unknown impurity is one that is detectable, but not chemically characterized)

$$(w/w) = (Wst \times Ssm \times Ast)/(Sst \times Wsm \times RRF \times 200)$$

Wst=Weight of malathion standard in mg
Wsm=Weight of malathion sample in mg
Ssm=Peak area of impurity obtained from sample solution
Sst=Average peak area of malathion obtained from known impurity standard solution
Ast=Assay of malathion standard in percent

TABLE VII

Analytical Parameters for Various Impurities and For Malathion

| Compound | Retention Time (min) | Relative Retention Time | Limit of Detection (LOD, %) | Limit of Quantitation (LOQ, %) | Relative Response Factor | Resolution |
|---|---|---|---|---|---|---|
| MeOOSPO | 1.7 | 0.08 | 0.04 | 0.05 | 0.06 | — |
| MeOSSPO | 2.1 | 0.10 | 0.02 | 0.03 | 0.2 | 3.3 |
| Malaoxon | 4.2 | 0.19 | 0.05 | 0.06 | 0.1 | 13.2 |
| MeOOSPS | 6.5 | 0.30 | 0.02 | 0.03 | 1.1 | 10.1 |
| Diethyl fumarate | 7.2 | 0.33 | 0.01 | 0.02 | 8.8 | 2.6 |
| Dimethyl malathion | 8.9 | 0.41 | 0.02 | 0.03 | 1.2 | 5.4 |
| Methyl malathion | 13.8 | 0.63 | 0.03 | 0.04 | 1.1 | 10.5 |
| Malathion | 21.8 | 1.00 | 0.03 | 0.04 | 1.0 | 11.0 |
| ethyl S-(1,2-dicarboethoxy)ethyl phosphorodithioate | 32.6 | 1.58 | 0.02 | 0.03 | 0.9 | — |
| Isomalathion | 5.3 | 0.3 | 0.02 | 0.03 | 0.3 | — |
| Malathion | 19.0 | 1.00 | 0.02 | 0.03 | 1.0 | — |

The limit of detection is the minimum concentration (% w/w) at which the analyte can reliably be detected. The limit of quantitation is the minimum concentration (% w/w) at which the analyte can reliably be quantified. Limits of detection and quantitation were determined by comparing measured signals from samples with known low concentrations of analyte to measured signals from blank samples. The relative response factor is the ratio of slopes provided by calibration curves for analyte and corresponding internal standard (or surrogate and corresponding internal standard). The resolution is the separation of two peaks in terms of their average peak width at base ($t_{R2} > t_{R1}$):

$$\text{Resolution} = \frac{(t_{R2} - t_{R1})}{(w_{b1} + w_{b2})/2} = \frac{2(t_{R2} - t_{R1})}{(w_{b1} + w_{b2})}$$

In the case of two adjacent peaks it may be assumed that $w_{b1} = w_{b2}$, and thus, the width of the second peak may be substituted for the average value: Resolution=$(t_{R2} - t_{R1})/w_{b2}$.

RRF=Relative Response Factor (1.0 for unknown impurities)

Note: For unknown impurities, values of Limit of Detection and Limit of Quantitation as for malathion were used, and relative response factor RRF=1

(c) Calculation of Malathion Purity

% Malathion Purity (w/w)=100−[% (w/w) known impurities+% (w/w) unknown impurities]

(d) Samples were analyzed for the presence of impurities by gas chromatography (GC) instrument with a FID detector. The chromatographic conditions used was: (i) Column—HP-5, 5% Phenyl Methyl Siloxane or equivalent; (ii) Sample introduction inlet—Split; (iii) Inlet temperature—230° C.; (iv) Split ratio—10:1; (v) Carrier Gas—He, constant flow of 3.5 mL/min; (vi) Injection volume—1 μL; (vii) Detection—FID; (viii) Detector temperature—250° C.; (ix) Constant Flow+Make-up Flow—30.0 mL/min; (x) Oven—Initial temperature, 100° C.; (xi) Initial time—8 min; (xii) Rate—25° C.; (xiii) Final temperature—220° C.; (xiv) Final time=7 min; (xv) Run time—19.8 min; and, (xv) Diluent—Acetonitrile.

EXAMPLE 10

Preparation of Impurities for Analytical Assays (a) O,O,S-Trimethyl Phosphorodithioate (McOOSPS)—

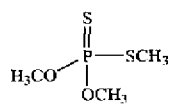

A solution of dimethyl dithiophosphoric acid in toluene was reacted with methyl iodide in the presence of sodium carbonate at ambient temperature and the toluene removed by filtration. The liquid residue was distilled at 130° C. to produce a colorless liquid.

(b) O,S,S-Trimethyl Phosphorodithioate (MeOSSPO)

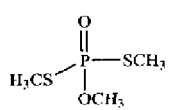

A solution of dimethyl dithiophosphoric acid in a mixture of toluene/acetonitrile was refluxed for 20 hours in the presence of KOH. The potassium salt of S,S-dimethyl phosphorodithioate was precipitated in an ice/water bath. The salt was collected by filtration. After filtration, the salt was suspended in acetonitrile and treated with dimethyl sulfate at the reflux temperature for 6 hours. Water was then added and the mixture refluxed for 1 hour to destroy excess of the methylating agent. The reaction mixture was filtered and the solvent evaporated. The residual residue was extracted into chloroform and the chloroform layer washed with water. The chloroform layer was dried over sodium sulfate and the residue vacuum distilled to yield MeOSSPO.

(c) Trimethyl Phosphorothioate (MeOOSPO)

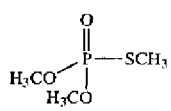

A pre-cooled solution of dimethyl dithiophosphoric acid in toluene was treated with $Cl_2$ while maintaining the reaction temperature between 5-10° C. The mixture was then heated to the reflux temperature for 1.5 hours. After cooling to room temperature, an aqueous solution of KOH was drop wise added to the reaction mixture until a basic (pH>7.0) was achieved. The organic and aqueous layers were separated and the aqueous layer evaporated to dryness. Acetonitrile was added to the solid residue, the mixture filtered and the acetonitrile evaporated. The residual residue was resuspended in acetonitrile and then treated with methyl iodide at ambient temperature for 10 hours. The solvent was evaporated and the residue extracted with ethyl acetate. After extraction, the ethyl acetate was evaporated to dryness. The residual liquid was vacuum distilled to yield MeOOSPO.

(d) Isomalathion

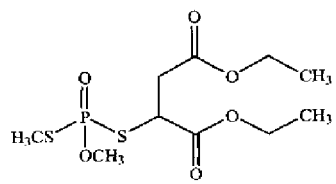

This product is commercially available from the United States Pharmacopeia, Reference Standard (B.No. F1B107) (www.usp.org).

(e) Malaoxon

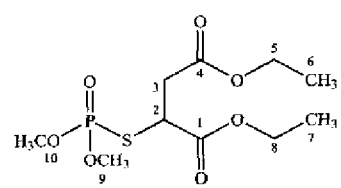

This product is commercially available European Pharmacopoeia Chemical Reference Substance (Ph. Eur. CRS) Malaoxon CRS (Malathion Impurity B), B.No. 2. (www.pheur.org).

(f) Dimethyl Malathion

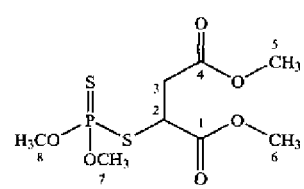

A mixture of malathion, methanol and a catalytic amount of concentrated sulfuric acid was refluxed for 7 hours. After cooling to ambient temperature, the solution was treated with aqueous solution of sodium bicarbonate. The solution was evaporated and extracted into chloroform. The chloroform layer was then filtered. The chloroform layer contained a mixture of malathion, mono-methyl malathion and dimethyl malathion. Dimethyl malathion was isolated by preparative HPLC.

(g) Methyl Malathion

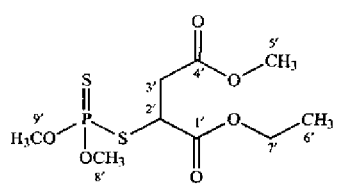

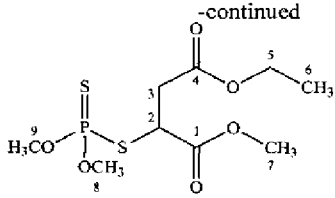

Mono-methyl malathion was isolated by preparative HPLC from the reaction mixture described in (f).

(h) Diethyl Fumarate

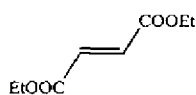

Diethyl Fumarate B.No. DEF M-354, purchased from SigmaAldrich (sigmaaldrich.com).

(i) O,O-dimethyl-S-(1-carboxy-2-carboethoxy) Ethyl Phosphorodithioate and the Corresponding Ethyl Analogue (Malathion Carboxylic Acids)

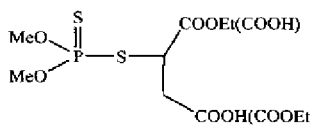

The malathion mono acids were prepared as described by N. Lee Wolfe et al. (*J. Agric. Food Chem.* 23(6):121-1215 (1976)).

(j) O,O-methyl ethyl S-(1,2-dicarboethoxy)ethyl Phosphorodithioate

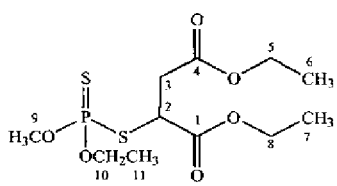

The chemical was prepared by two chemical steps and one purification step.

(i) Step I: Preparation of Dithiolo Acids

Twenty grams of $P_2S_5$ was suspended in toluene. A mixture of 1:1 (v/v) of methanol:ethanol was added drop-wise while maintaining the temperature below 70° C. After addition of the methanol:ethanol, air was bubbled through the reaction mass to remove any dissolved $H_2S$. The mixture was then cooled to ambient temperature and any un-reacted $P_2S_5$ removed by filtration. The toluene solution was extracted with water.

(ii) Step II: Preparation of Crude Malathion Derivatives

The aqueous layer containing the dithiolo acids was treated with diethyl maleate together with hydroquinone at 55° C. After 5 hours, the reaction mass was cooled to ambient temperature and the layers separated. The lower organic layer was washed twice with water and the reaction mixture analyzed by gas chromatography and HPLC. There were three main products: (i) malathion (19.3%); (ii) O,O-methyl ethyl S-(1,2-dicarboethoxy)ethyl phosphorodithioate (38.82%); and, (iii) O,O-diethyl S-(1,2-dicarboethoxy)ethyl phosphorodithioate (8.87%) (data is shown as the % area).

(iii) Step III: Purification of O,O-methyl Ethyl S-(1,2-dicarboethoxy)ethyl Phosphorodithioate The products were isolated by preparative HPLC.

(k) Diethyl 2-mercaptosuccinate

The corresponding mercapto diacid (10 grams) was esterified in 100 ml of absolute ethanol in the presence of 1 gram of sulfuric acid 98% at reflux for 3 hours. The reaction mixture was then cooled to ambient temperature and a major portion of the ethanol removed under reduced pressure. Water and ethylacetate were added to the residue. The layers were separated and the organic solvent removed to yield a colorless product with a purity by gas chromatography of 96% (w/w).

(l) Tetraethyl Dithiosuccinate

Diethyl 2-mercaptosuccinate was treated with 30% (v/v) hydrogen peroxide at ambient temperature for 16 hours in the presence of catalytic amount of HCl (32%). The reaction mixture was extracted with ethyl acetate and the organic layer washed with 2% sodium hydroxide solution in water to get rid of any un-reacted starting material. Removal of the solvent yielded a colorless product with purity of 95% (GC).

(m) Tetraethyl Thiosuccinate

The sodium salt of diethyl 2-mercaptosuccinate was reacted in two layer system (toluene/water) at ambient temperature with diethyl malaeate to yield the desired product.

EXAMPLE 11:

Additional Purification of the Malathion Prepared in Example 3

The malathion from Example 3 was further purified as follows. The malathion was stirred with water (approximately 1:3 parts by weight) and the mixture heated to about 65° C. under vacuum. Fresh water was added and the mixture distilled a second time. After distillation of about 35 liters of water, the purity of the malathion was checked by HPLC.

EXAMPLE 12:

Analysis of Malathion from Example 11

The purity of the malathion and the percentage of impurities present were determined by HPLC. The mobile phase composition and/or flow rate were adjusted to meet the chromatographic parameters. The results of the HPLC analysis for one batch of wet malathion is shown below in Table VIII. Malathion free of water may be obtained by heating the malathion after addition of water followed by azeotropic distillation at a temperature from about 35° C. to about 45° C., together with air bubbling through the wet mass. The water content may be monitored by the Karl Fisher procedure. United States Pharmacopeia <921>. When the water content is reduced to not more than 0.1% (w/w), the malathion is cooled and filtered to remove any foreign particles. Filtration may be through glass paper.

TABLE VIII

Assay of Malathion Before Drying

| Analyte | Wet Malathion (% (w/w)) |
|---|---|
| MeOOSPS | 0.1% |
| Malaoxon | <0.05% |
| Diethyl Fumarate | <0.01% |
| Dimethylmalathion | <0.02% |

TABLE VIII-continued

Assay of Malathion Before Drying

| Analyte | Wet Malathion (% (w/w)) |
|---|---|
| Methylmalathion | 0.06% |
| Isomalathion | 0.07% |
| Any other detectable impurity | 0.04% |
| Malathion purity | 99.5% |

EXAMPLE 13:

Preparation of Crude Malathion

The aqueous solution of dimethyldithiophosphoric acid prepared in Example 1 was combined with diethyl maleate (1.33 kg) and hydroquinone (3.3 g), and the resulting two-phase mixture was heated for 8 h at 53-57° C. under nitrogen atmosphere. The two-phase mixture was cooled to 22-30° C., and the phases were separated. The organic phase was washed with water (2 X 1 kg) to afford crude malathion (1.86 kg) containing at least about 30% (w/w) diethyl fumarate.

EXAMPLE 14:

Removal of Diethyl Fumarate from Crude Malathion Under Acidic Conditions

Sodium bisulfite (1 kg) was dissolved in water (4 kg), and the pH of the solution was adjusted to 6.1-6.3 by addition of 50% (w/w) sodium hydroxide (0.37 kg).

The pH-adjusted solution was combined with the crude malathion from Example 13, and the resulting two-phase mixture was heated at 60-65° C. for 2 hours. The final pH of the mixture was about 6.8-6.9. The mixture was cooled to 22-30° C. and the phases were separated. The organic phase was washed with water (1.5 kg), and the phases were separated. Next, the organic phase was washed with 2.5% (w/w) aqueous sodium hydroxide (1.5 kg), and the phases were separated. Finally, the organic phase was washed with water (2 X 1 kg) to afford malathion (0.94 kg).

The purity of the obtained malathion was determined using HPLC as set forth above (See Methodology and Protocols, In-Process Purity Determination by HPLC). The quantities of known and unknown impurities are listed in the following table:

| Compound | Quantity (% w/w) |
|---|---|
| Diethyl fumarate | 0.05 |
| Isomalathion | <0.04 (LOD) |
| MeOOSPS | 3.5 |
| Malaoxon | <0.05 (LOD) |
| Dimethyl malathion | <0.02 (LOD) |
| Methyl malathion | <0.03 (LOD) |
| O, O—Me, Et Malathion analog[1] | 0.06 |
| Tetraethyl dithiodisuccinate[1] | 0.04 |
| Unknown (RRT = 0.38) | 0.05 |

[1]Values of Limit of Detection and Limit of Quantitation as for malathion were used, and relative response factor RRF = 1

These data demonstrate that greater than 99% (w/w) of the diethyl fumarate was removed from the crude malathion. These data further demonstrate that the purified malathion contained only 0.04% (w/w) of tetraethyl dithiodisuccinate.

Example 15:

Removal of MeOOSPS from Crude Malathion

Water (2.8 kg) was added to the malathion from Example 14, and the resulting two-phase mixture was subjected to azeotropic distillation over the course of four days at a temperature of about 35-50° C. and a pressure of about 30-60 mbar. Water was added to the mixture at approximately one-hour intervals to replace the quantity removed by distillation during that period (about 0.2-0.7 L each time). A total of about 34.2 L of water was distilled during this process. The two-phase mixture was cooled to 22-30° C., and the phases were separated, providing wet pharmaceutical grade malathion (0.84 kg).

The purity of the obtained malathion was determined using HPLC as set forth above (See Methodology and Protocols, In-Process Purity Determination by HPLC). The quantities of known and unknown impurities are listed in the following table:

| Compound | Quantity (% w/w) |
|---|---|
| Diethyl fumarate | <0.01 (LOD) |
| Isomalathion | 0.07 |
| MeOOSPS | 0.1 |
| Malaoxon | <0.05 (LOD) |
| Dimethyl malathion | <0.02 (LOD) |
| Methyl malathion | 0.06 |
| Unknown (RRT = 0.38) | 0.05 |
| Malathion Purity | 99.5 |

These data demonstrate that at least 97% (w/w) of the MeOOSPS was removed from the malathion of Example 3. These data further demonstrate that the purified malathion contained only 0.07% (w/w) of isomalathion.

Example 16:

Preparation of Dry Pharmaceutical Grade Malathion

The wet pharmaceutical grade malathion from Example 15 was heated at 38-42° C., and air was bubbled through the wet mass for about 20 hours. Water content was then determined by a Karl Fisher procedure according to USP Method I <921>, and found to be 0.05% (w/w). The mixture was then cooled to room temperature and filtered through glass paper, to provide dry pharmaceutical grade malathion (0.8 kg).

The purity of the obtained malathion was determined using HPLC as set forth above (See Methodology and Protocols: End-of-Process Determination of Assay, Purity, and Impurities Other Than Isomalathion, End-of-Process Determination of Isomalathion). The quantities of known and unknown impurities are listed in the following table:

| Compound | Quantity (% w/w) |
|---|---|
| MeOOSPO | <0.04 (LOD) |
| MeOSSPO | <0.02 (LOD) |
| MeOOSPS | 0.1 |
| Malaoxon | <0.05 (LOD) |
| Diethyl fumarate | <0.01 (LOD) |
| Dimethyl malathion | <0.02 (LOD) |
| Methyl malathion | 0.06 |
| O, O—Me, Et Malathion analog[1] | 0.08 |
| Isomalathion | <0.02 (LOD) |

41

-continued

| Compound | Quantity (% w/w) |
|---|---|
| Tetraethyl dithiodisuccinate[1] | 0.06 |
| Unknown (RRT = 0.38) | 0.04 |
| Total | 0.3 |

[1]Values of Limit of Detection and Limit of Quantitation as for malathion were used, and relative response factor RRF = 1

The assay of the obtained malathion was determined using HPLC as set forth above (See Methodology and Protocols: End-of-Process Determination of Assay, Purity, and Impurities Other Than Isomalathion), and found to be 99.5% (w/w).

Example 17:

Preparation of Pharmaceutical Grade Malathion

Two additional batches of pharmaceutical grade malathion were prepared by procedures analogous to those in Examples 1 and 13-16. The purity of the obtained malathion was determined using HPLC as set forth above (See Methodology and Protocols: End-of-Process Determination of Assay, Purity, and Impurities Other Than Isomalathion, End-of-Process Determination of Isomalathion). The quantities of known and unknown impurities are listed in the following table:

| Compound | Quantity (% w/w) in Batch 1 | Quantity (% w/w) in Batch 2 |
|---|---|---|
| MeOOSPO | <0.04 (LOD) | <0.04 (LOD) |
| MeOSSPO | <0.02 (LOD) | <0.02 (LOD) |
| MeOOSPS | 0.09 | 0.09 |
| Malaoxon | <0.05 (LOD) | <0.05 (LOD) |
| Diethyl fumarate | 0.06 | <0.01 |
| Dimethyl malathion | <0.02 (LOD) | <0.02 (LOD) |
| Methyl malathion | 0.08 | 0.07 |
| O, O—Me, Et Malathion analog[1] | 0.11 | 0.09 |
| Isomalathion | <0.02 (LOD) | <0.02 (LOD) |
| Tetraethyl dithiodisuccinate[1] | 0.08 | 0.08 |
| Unknown (RRT = 0.38) | 0.06 | 0.05 |
| Total | 0.5 | 0.4 |

[1]Values of Limit of Detection and Limit of Quantitation as for malathion were used, and relative response factor RRF = 1

Example 18:

Storage Stability

Four (4) samples of Dry Pharmaceutical Grade Malathion from Example 16, each weighing about 3-3.5 grams, were placed in separate clear glass bottles closed by a cap coated with polytetrafluoroethylene (PTFE). Each bottle was then inserted into a separate black polyethylene (PE) bag, which was tightly closed with a strip fastener. Each bag was then placed in a separate carton box.

The four (4) samples were stored for three (3) months under the following conditions:
Sample One: 40° C.±2° C. and 75%±5% relative humidity,
Sample Two: 30° C.±2° C. and 60%±5% relative humidity,
Sample Three: 25° C.±2° C. and 60%±5% relative humidity, and
Sample Four: 5° C.±3° C. and ambient relative humidity.

The purity of each sample was determined after storage for one (1), two (2), and three (3) months using HPLC as set forth above (See Methodology and Protocols: End-of-Process

42

Determination of Assay, Purity, and Impurities Other Than Isomalathion, End-of-Process Determination of Isomalathion). The quantities of known and unknown impurities for each sample are listed in the following tables:

TABLE 1

Storage at 40° C. ± 2° C. and 75% ± 5% relative humidity

| Compound | Quantity (% w/w) After 1 Month | Quantity (% w/w) After 2 Months | Quantity (% w/w) After 3 Months |
|---|---|---|---|
| MeOOSPO | <0.04 (LOD) | <0.04 (LOD) | 0.05 |
| MeOSSPO | <0.02 (LOD) | <0.02 (LOD) | <0.02 (LOD) |
| MeOOSPS | 0.1 | 0.2 | 0.2 |
| Malaoxon | <0.05 (LOD) | <0.05 (LOD) | <0.05 (LOD) |
| Diethyl fumarate | <0.01 (LOD) | <0.01 (LOD) | <0.02 (LOQ) |
| Dimethyl malathion | <0.02 (LOD) | <0.02 (LOD) | <0.02 (LOD) |
| Methyl malathion | 0.06 | 0.06 | 0.06 |
| O, O—Me, Et Malathion analog[1] | 0.08 | 0.07 | 0.07 |
| Isomalathion | 0.06 | 0.1 | 0.1 |
| Tetraethyl dithiodisuccinate[1] | 0.06 | 0.05 | 0.07 |
| Unknown (RRT = 0.06) | <0.02 (LOD) | <0.02 (LOD) | 0.04 |
| Unknown (RRT = 0.25) | <0.02 (LOD) | 0.06 | 0.12 |
| Unknown (RRT = 0.27) | 0.10 | 0.38 | 0.76 |
| Unknown (RRT = 0.38) | 0.04 | 0.04 | 0.04 |

[1]Values of Limit of Detection and Limit of Quantitation as for malathion were used, and relative response factor RRF = 1

TABLE 2

Storage at 30° C. ± 2° C. and 60% ± 5% relative humidity

| Compound | Quantity (% w/w) After 1 Month | Quantity (% w/w) After 2 Months | Quantity (% w/w) After 3 Months |
|---|---|---|---|
| MeOOSPO | <0.04 (LOD) | <0.04 (LOD) | <0.04 (LOD) |
| MeOSSPO | <0.02 (LOD) | <0.02 (LOD) | <0.02 (LOD) |
| MeOOSPS | 0.1 | 0.1 | 0.1 |
| Malaoxon | <0.05 (LOD) | <0.05 (LOD) | <0.05 (LOD) |
| Diethyl fumarate | <0.01 (LOD) | <0.01 (LOD) | <0.01 (LOD) |
| Dimethyl malathion | <0.02 (LOD) | <0.02 (LOD) | <0.02 (LOD) |
| Methyl malathion | 0.05 | 0.06 | 0.06 |
| O, O—Me, Et Malathion analog[1] | 0.08 | 0.08 | 0.07 |
| Isomalathion | 0.03 | 0.04 | 0.06 |
| Tetraethyl dithiodisuccinate[1] | 0.06 | 0.05 | 0.06 |
| Unknown (RRT = 0.06) | <0.02 (LOD) | <0.02 (LOD) | 0.04 |
| Unknown (RRT = 0.27) | <0.02 (LOD) | 0.07 | 0.15 |
| Unknown (RRT = 0.38) | 0.04 | 0.04 | 0.04 |

[1]Values of Limit of Detection and Limit of Quantitation as for malathion were used, and relative response factor RRF = 1

TABLE 3

Storage at 25° C. ± 2° C. and 60% ± 5% relative humidity

| Compound | Quantity (% w/w) After 1 Month | Quantity (% w/w) After 2 Months | Quantity (% w/w) After 3 Months |
|---|---|---|---|
| MeOOSPO | <0.04 (LOD) | <0.04 (LOD) | <0.04 (LOD) |
| MeOSSPO | <0.02 (LOD) | <0.02 (LOD) | <0.02 (LOD) |
| MeOOSPS | 0.1 | 0.1 | 0.1 |
| Malaoxon | <0.05 (LOD) | <0.05 (LOD) | <0.05 (LOD) |

TABLE 3-continued

Storage at 25° C. ± 2° C. and 60% ± 5% relative humidity

| Compound | Quantity (% w/w) After 1 Month | Quantity (% w/w) After 2 Months | Quantity (% w/w) After 3 Months |
|---|---|---|---|
| Diethyl fumarate | <0.01 (LOD) | <0.01 (LOD) | <0.01 (LOD) |
| Dimethyl malathion | <0.02 (LOD) | <0.02 (LOD) | <0.02 (LOD) |
| Methyl malathion | 0.05 | 0.05 | 0.06 |
| O, O—Me, Et Malathion analog[1] | 0.08 | 0.07 | 0.07 |
| Isomalathion | <0.03 (LOQ) | <0.02 (LOD) | 0.04 |
| Tetraethyl dithiodisuccinate[1] | 0.06 | 0.06 | 0.06 |
| Unknown (RRT = 0.27) | <0.02 (LOD) | <0.02 (LOD) | 0.06 |
| Unknown (RRT = 0.38) | 0.04 | 0.04 | 0.04 |

[1]Values of Limit of Detection and Limit of Quantitation as for malathion were used, and relative response factor RRF = 1

TABLE 4

Storage at 5° C. ± 3° C. and ambient relative humidity

| Compound | Quantity (% w/w) After 1 Month | Quantity (% w/w) After 2 Months | Quantity (% w/w) After 3 Months |
|---|---|---|---|
| MeOOSPO | <0.04 (LOD) | <0.04 (LOD) | <0.04 (LOD) |
| MeOSSPO | <0.02 (LOD) | <0.02 (LOD) | <0.02 (LOD) |
| MeOOSPS | 0.1 | 0.1 | 0.1 |
| Malaoxon | <0.05 (LOD) | <0.05 (LOD) | <0.05 (LOD) |
| Diethyl fumarate | <0.01 (LOD) | <0.01 (LOD) | <0.01 (LOD) |
| Dimethyl malathion | <0.02 (LOD) | <0.02 (LOD) | <0.02 (LOD) |
| Methyl malathion | 0.05 | 0.06 | 0.06 |
| O, O—Me, Et Malathion analog[1] | 0.07 | 0.07 | 0.07 |
| Isomalathion | <0.02 (LOD) | <0.03 (LOQ) | <0.03 (LOQ) |
| Tetraethyl dithiodisuccinate[1] | 0.06 | 0.06 | 0.06 |
| Unknown (RRT = 0.38) | 0.04 | 0.04 | 0.04 |

[1]Values of Limit of Detection and Limit of Quantitation as for malathion were used, and relative response factor RRF = 1

This Example demonstrates that the pharmaceutical grade malathion prepared in accordance with the present invention is storage stable.

Comparative Example 1
Purification of Malathion Contaminated with Diethyl Fumarate at Alkaline pH Crude malathion was prepared as in Examples 1 and 13, and then treated with sodium bisulfite as in Example 14. However, the final pH of the two-phase mixture was about 7.2.

The purity of the obtained malathion was determined using HPLC as set forth above (See Methodology and Protocols, In-Process Purity Determination by HPLC). The quantity of tetraethyl dithiodisuccinate was 0.24% (w/w).

This Example demonstrates that when the pH of the mixture rose above 7, the tetraethyl dithiodisuccinate level was greater than 0.2% (w/w).

Comparative Example 2
Dimerization of Diethyl 2-Mercaptosuccinate at Alkaline pH Sodium bisulfite (20 g, 0.192 mol) was dissolved in water (80 mL), and the pH of the solution was adjusted to 7.46 by addition of 50% (w/w) sodium hydroxide (15.37 g, 0.192 mol).

The pH-adjusted solution (4 g) was combined with diethyl 2-mercaptosuccinate (0.5 g), and the resulting mixture was stirred at ambient temperature. The quantity of tetraethyl dithiodisuccinate was determined at various time points by gas chromatography as set forth above (See Methodology and Protocols, Malathion Analysis by GC).

| Time | Quantity (% w/w) |
|---|---|
| 0 | 0 |
| 2 hours | 3.8 |
| 4 hours | 10.75 |
| 24 hours | 75 |

This Example demonstrates that diethyl 2-mercaptosuccinate dimerizes to tetraethyl dithiodisuccinate at alkaline pH.

Comparative Example 3 Analysis of Commercial Malathion

Three (3) commercial batches of pharmaceutical grade malathion were obtained. The three (3) batches of pharmaceutical grade malathion were prepared and purified by a process different from the process of the present invention. The purity of each commercial batch of malathion was determined using HPLC as set forth above (See Methodology and Protocols: End-of-Process Determination of Assay, Purity, and Impurities Other Than Isomalathion, End-of-Process Determination of Isomalathion). The quantities of known and unknown impurities are listed in the following table:

| Compound | Quantity (% w/w) in Batch 1 | Quantity (% w/w) in Batch 2 | Quantity (% w/w) in Batch 3 |
|---|---|---|---|
| MeOOSPO | 0.05 | 0.05 | 0.06 |
| MeOSSPO | <0.02 (LOD) | <0.02 (LOD) | <0.02 (LOD) |
| MeOOSPS | 0.04 | 0.06 | 0.05 |
| Malaoxon | <0.05 (LOD) | 0.07 | <0.05 (LOD) |
| Diethyl fumarate | 0.02 | <0.02 (LOQ) | 0.02 |
| Dimethyl malathion | <0.02 (LOD) | <0.02 (LOD) | <0.02 (LOD) |
| Methyl malathion | 0.2 | 0.1 | 0.2 |
| O, O—Me, Et Malathion analog[1] | 0.13 | 0.09 | 0.11 |
| Isomalathion | 0.2 | 0.2 | 0.2 |
| Tetraethyl dithiodisuccinate[1] | <0.03 (LOD) | <0.03 (LOD) | <0.03 (LOD) |
| Unknown (RRT = 0.25) | <0.03 (LOD) | 0.13 | 0.10 |
| Unknown (RRT = 0.27) | 0.13 | 1.05 | 0.78 |
| Total Impurities | 0.8 | 1.8 | 1.5 |

[1]Values of Limit of Detection and Limit of Quantitation as for malathion were used, and relative response factor RRF = 1

Numerous references, including patents and various publications, are cited and discussed in the description of this invention. The citation and discussion of such references is provided merely to clarify the description of the present invention and is not an admission that any reference is prior art to the invention described herein. All references cited and discussed in this specification are incorporated herein by reference in their entirety. The embodiments illustrated and discussed in this specification are intended only to teach those skilled in the art the best way known to the inventors to make and use the invention. Nothing in this specification should be considered as limiting the scope of the present invention. Modifications and variation of the above-described embodiments of the invention are possible without departing from the invention, as appreciated by those skilled in the art in light of the above teachings. It is therefore understood that, within the scope of the claims and their equivalents, the invention may be practiced otherwise than as specifically described.

What is claimed is:
1. A pharmaceutical formulation comprising pharmaceutical grade malathion, said pharmaceutical grade malathion containing 0.1% or less (w/w) MeOOSPO, 0.1% or less (w/w) MeOSSPO, 0.2% or less (w/w) MeOOSPS, less than 0.1% (w/w) methyl malathion, 0.1% or less (w/w) malaoxon and 0.1% or less (w/w) isomalathion.

2. The pharmaceutical formulation of claim 1, comprising pharmaceutical grade malathion having a purity of greater than 99% (w/w).

3. The pharmaceutical formulation of claim 1 wherein the malathion in the formulation contains 0.05% or less (w/w) MeOOSPO.

4. The pharmaceutical formulation of claim 1 wherein the malathion in the formulation contains 0.04% or less (w/w) MeOOSPO.

5. The pharmaceutical formulation of claim 1 wherein the malathion in the formulation contains 0.02% or less (w/w) MeOSSPO.

6. The pharmaceutical formulation of claim 1, comprising pharmaceutical grade malathion containing not more than about 0.1% (w/w) of any other detectable impurity.

7. The pharmaceutical formulation of claim 1, wherein the malathion in the formulation contains 0.08% or less (w/w) methyl malathion.

8. The pharmaceutical formulation of claim 1, wherein the malathion in the formulation contains 0.06% or less (w/w) methyl malathion.

9. The pharmaceutical formulation of claim 1, wherein the malathion in the formulation contains 0.05% or less (w/w) isomalathion.

10. The pharmaceutical formulation of claim 1, wherein the malathion in the formulation contains 0.02% or less (w/w) isomalathion.

11. The pharmaceutical formulation of claim 1, wherein the malathion in the formulation contains 0.2% or less (w/w) diethyl fumarate and 0.2% or less (w/w) dimethylmalathion.

12. The formulation of claim 1, wherein the malathion in the formulation contains less than 0.05% (w/w) malaoxon.

13. The pharmaceutical formulation of claim 1 wherein the malathion in the formulation contains 0.1% or less (w/w) MeOOSPS.

14. The pharmaceutical formulation of claim 1, wherein the amount of isomalathion is not more than 0.1% (w/w), after storage for 3 months at 25° C. and 60% relative humidity.

15. The pharmaceutical formulation of claim 1, wherein the amount of isomalathion is not more than 0.1% (w/w), after storage for 3 months at 30° C. and 60% relative humidity.

16. The pharmaceutical formulation of claim 1, wherein the amount of isomalathion is not more than 0.1% (w/w), after storage for 3 months at 40° C. and 75% relative humidity.

17. A pharmaceutical formulation comprising at least 0.5% (w/w) malathion wherein the malathion contains less than 0.1% (w/w) isomalathion, less than 0.2% (w/w) MeOOSPS, less than 0.1% (w/w) malaoxon, and less than 0.07% methyl malathion.

18. The pharmaceutical formulation of claim 17, wherein the malathion has a purity greater than 98.5% (w/w).

19. The pharmaceutical formulation of claim 18, wherein the malathion has a purity greater than 99.0% (w/w).

20. The pharmaceutical formulation of claim 17, wherein the malathion contains less than 0.1% (w/w) MeOOSPO, less than 0.1% (w/w) MeOSSPO, and less than 0.1% malathion carboxylic acids.

21. The pharmaceutical formulation of claim 17, comprising 0.65% (w/w) of the pharmaceutical grade malathion.

22. The pharmaceutical formulation of claim 17, further comprising terpineol, dipentene, pine needle oil, and isopropyl alcohol.

23. The pharmaceutical formulation of claim 22, wherein the pharmaceutical formulation comprises at least 70% (w/w) isopropyl alcohol.

24. The pharmaceutical formulation of claim 22, comprising at least 12% (w/w) terpineol, at least 10% (w/w) dipentene, and at least 0.28% (w/w) pine needle oil.

25. The pharmaceutical formulation of claim 17 wherein the formulation is a lotion, gel, cream or solution.

26. The pharmaceutical formulation of claim 17, wherein the amount of isomalathion is less than 0.05% (w/w), after storage for 3 months at 5° C.

27. The pharmaceutical formulation of claim 17, wherein the amount of isomalathion is not more than 0.05% (w/w), after storage for 3 months at 25° C. and 60% relative humidity.

28. The pharmaceutical formulation of claim 17, wherein the amount of isomalathion is not more than 0.05% (w/w), after storage for 3 months at 30° C. and 60% relative humidity.

29. The pharmaceutical formulation of claim 17, wherein the amount of isomalathion is not more than 0.07% (w/w), after storage for 3 months at 40° C. and 75% relative humidity.

30. A pharmaceutical formulation comprising pharmaceutical grade malathion, said pharmaceutical grade malathion having a purity greater than 98.5% and containing 0.1% or less (w/w) MeOOSPO, 0.1% or less (w/w) MeOSSPO, 0.2% or less (w/w) MeOOSPS, less than 0.1% (w/w) methyl malathion, 0.1% or less (w/w) malaoxon and 0.1% or less (w/w) isomalathion.

31. The pharmaceutical formulation of claim 30, wherein the malathion further contains less than 0.1% (w/w) malathion carboxylic acids.

32. The pharmaceutical formulation of claim 30, containing not more than about 0.1% (w/w) of any other detectable impurity.

33. The pharmaceutical formulation of claim 1, wherein the pharmaceutical formulation is a lotion.

34. The pharmaceutical formulation of claim 33, comprising pharmaceutical grade malathion having a purity of greater than 99% (w/w).

35. The pharmaceutical formulation of claim 33 wherein the malathion in the formulation contains 0.05% or less (w/w) MeOOSPO.

36. The pharmaceutical formulation of claim 33, comprising pharmaceutical grade malathion containing 0.1% or less (w/w) of any detectable impurity other than MeOOSPO, MeOSSPO, MeOOSPS, methyl malathion, malaoxon or isomalathion.

37. The pharmaceutical formulation of claim 33, wherein the malathion in the formulation contains 0.08% or less (w/w) methyl malathion.

38. The pharmaceutical formulation of claim 33, wherein the malathion in the formulation contains 0.05% or less (w/w) isomalathion.

39. The pharmaceutical formulation of claim 33, wherein the malathion in the formulation contains 0.2% or less (w/w) diethyl fumarate and 0.2% or less (w/w) dimethylmalathion.

40. The formulation of claim 33, wherein the malathion in the formulation contains less than 0.05% (w/w) malaoxon.

41. The pharmaceutical formulation of claim 33 wherein the malathion in the formulation contains 0.1% or less (w/w) MeOOSPS.

42. The pharmaceutical formulation of claim 33, wherein the amount of isomalathion is not more than 0.1% (w/w), after storage for 3 months at 25° C. and 60% relative humidity.

43. The pharmaceutical formulation of claim 33, comprising 0.65% (w/w) of the pharmaceutical grade malathion.

44. The pharmaceutical formulation of claim 33, further comprising terpineol, dipentene, pine needle oil, and isopropyl alcohol.

45. The pharmaceutical formulation of claim 33, wherein the pharmaceutical formulation comprises at least 70% (w/w) isopropyl alcohol.

46. The pharmaceutical formulation of claim 33, comprising at least 12% (w/w) terpineol, at least 10% (w/w) dipentene, and at least 0.28% (w/w) pine needle oil.

47. The pharmaceutical formulation of claim 17, wherein the pharmaceutical formulation is a gel.

48. The pharmaceutical formulation of claim 47, wherein the malathion has a purity greater than 99.0% (w/w).

49. The pharmaceutical formulation of claim 47, wherein the malathion contains less than 0.1% (w/w) MeOOSPO, less than 0.1% (w/w) MeOSSPO, and less than 0.1% malathion carboxylic acids.

50. The pharmaceutical formulation of claim 47, comprising 0.65% (w/w) of the pharmaceutical grade malathion.

51. The pharmaceutical formulation of claim 47, further comprising terpineol, dipentene, pine needle oil, and isopropyl alcohol.

52. The pharmaceutical formulation of claim 47, wherein the pharmaceutical formulation comprises at least 70% (w/w) isopropyl alcohol.

53. The pharmaceutical formulation of claim 47, wherein the amount of isomalathion is not more than 0.05% (w/w), after storage for 3 months at 25° C. and 60% relative humidity.

54. The pharmaceutical formulation of claim 30, wherein the pharmaceutical formulation is a lotion.

55. The pharmaceutical formulation of claim 30, wherein the pharmaceutical formulation is a gel.

* * * * *